United States Patent [19]
Newgard et al.

[11] Patent Number: 5,891,717
[45] Date of Patent: Apr. 6, 1999

[54] METHODS AND COMPOSITIONS FOR INHIBITING HEXOKINASE

[75] Inventors: Christopher B. Newgard; He-Ping Han, both of Dallas; Thomas C. Becker, Carrollton, all of Tex.; John E. Wilson, East Lansing, Mich.

[73] Assignees: Betagene, Inc., Dallas; Board of Regents, The University of Texas System, Austin, both of Tex.

[21] Appl. No.: 588,976

[22] Filed: Jan. 19, 1996

[51] Int. Cl.$^6$ .............................. C12N 5/10; C12N 15/85; C12N 15/56; C12N 15/62

[52] U.S. Cl. ...................... 435/325; 435/69.1; 435/64.7; 435/194; 435/320.1; 435/455; 435/456; 435/458; 435/463; 536/23.2; 536/23.4; 935/13; 935/14; 935/32; 935/57; 935/60; 935/70; 935/71

[58] Field of Search ................................. 435/69.1, 69.7, 435/194, 172.3, 252.3, 320.1, 325, 455, 456, 458, 463; 536/23.2, 23.4

[56] References Cited

U.S. PATENT DOCUMENTS

| | | | |
|---|---|---|---|
| 5,175,085 | 12/1992 | Johnson et al. | 435/7.21 |
| 5,427,940 | 6/1995 | Newgard | 435/366 |
| 5,585,479 | 12/1996 | Hoke et al. | 536/24.5 |
| 5,744,327 | 4/1998 | Newgard | 435/69.4 |
| 5,747,325 | 5/1998 | Newgard | 435/240.2 |

FOREIGN PATENT DOCUMENTS

| | | |
|---|---|---|
| 0 247 494 A2 | 12/1987 | European Pat. Off. . |
| WO9500644 | 5/1995 | WIPO . |
| WO 97/42326 | 11/1997 | WIPO . |

OTHER PUBLICATIONS

Arora, K. K., et al., The Journal of Biological Chemistry, vol. 266, "Glucose Phosphorylation: site–directed mutations which impair the catalytic function of hexokinase", pp. 5359–5362, 1991.

Stoffel, M., et al., Proceedings of the National Academy of Sciences, U.S.A., vol. 89, "Human glucokinase gene: Isolation, characterization and identification of two missense mutations linked to early–onset non–insulin–dependent (type 2) diabetes mellitu, 1992.

Adams et al., "Porin interaction with hexokinase and glycerol kinase: Metabolic microcompartmentation at the outer mitochondrial membrane," *Bioch. Med. Met. Biol.*, 45:271–291, 1991.

Arora et al., "Structure/Function Relationships in Hexokinase, Site–Directed Mutational Analyses and Characterization of Overexpressed Fragments Implicate Different Functions for the N– and C–Terminal Halves of the Enzyme," *J. Biological Chemistry*, 268(24):18259–18266, 1993.

Baijal, et al., "Functional Consequences of Mutation of Highly Conserved Serine Residues, Found at Equivalent Positions in the N– and C–Terminal Domains of Mammalian Hexokinases," *Arch. Bioch. Biophys.*, 298(1):271–278, 1992.

(List continued on next page.)

*Primary Examiner*—Robert A. Wax
*Assistant Examiner*—William W. Moore
*Attorney, Agent, or Firm*—Arnold, White & Durkee

[57] ABSTRACT

Disclosed are compositions and methods for inhibiting hexokinase enzymes in mammalian cells. Specifically provided are proteins that stimulate the production of trehalose-6-phosphate and their respective genes; hexokinase-specific ribozymes and genes encoding such constructs; and agents that competitively reduce hexokinase activity, e.g., by displacing hexokinase from mitochondria, and their respective genes. The latter group of agents includes inactive hexokinases and fragments thereof that retain mitochondrial binding functions and hexokinase-glucokinase chimeras that further substitute glucokinase activity for hexokinase activity. Mammalian cells including such hexokinase inhibitors, methods of making such cells and various in vitro and in vivo methods of using cells with reduced hexokinase activity are also described herein.

79 Claims, 6 Drawing Sheets

OTHER PUBLICATIONS

Becker et al., "Overexpression of Hexokinase I in Isolated Islets of Langerhans via Recombinant Adenovirus," *J. Biol. Chem.,* 269(33):21234–21238, 1994.

Bell et al., "Characterization of the 56–kDa Subunit of Yeast Trehalose–6–Phosphate Synthase and Cloning of its Gene Reveal its Identity with the Product of CIF1, a Regulator of Carbon Catabolite Inactivation," *Eur. J. Biochem.,* 209:951–959, 1992.

BeltrandelRio et al., "Genetic Engineering of Insulin Secreting Cell Lines," In: *Pancreatic Islet Transplantation vol. 1: Procurement of Pancreatic Islets,* Lanza, R.P. and Chick, W.L. (Eds.), R.G. Landes Co., 15:169–183, 1994.

BeltrandelRio et al., "Molecular or Chemical Reduction in Hexokinase Expression Alters Glucose Dose–Response in Engineered Insulinoma Cells," *Diabetes* 43, Suppl. 1:91A, Abstract No. 288, 1994.

Blásquez et al., "Trehalose–6–Phosphate, a New Regulator of Yeast Glycolysis that Inhibits Hexokinases," *FEBS Lett.,* 329(1,2):51–54, Aug., 1993.

Burch et al., "Adaption of Glycolytic Enzymes. Glucose Use and Insulin Release in Rat Pancreatic Islets During Fasting and Refeeding," *Diabetes* 30:923–928, 1981..

Cassidy and Newgard, "Glucose–Stimulated Insulin Secretion in Cell Lines," *Diab. Nutr. Metab.,* 7:189–195, 1994.

Clark et al., "Modulation of Glucose–Induced Insulin Secretion from a Rat Clonal β–Cell Line," *Endocrinology,* 127(6):2779–2788, 1990.

Efrat et al., "Beta–Cell Lines Derived from Transgenic Mice Expressing a Hybrid Insulin Gene–Oncogene," *Proc. Natl. Acad. Sci. USA,* 85:9037–9041, 1988.

Efrat et al., "Murine Insulinoma Cell Line with Normal Glucose–Regulated Insulin Secretion," *Diabetes,* 42:901–907, 1993.

Efrat et al., "Ribozyme–Mediated Attenuation of Pancreatic β–Cell Glucokinase Expression in Transgenic Mice Results in Impaired Glucose–Induced Insulin Secretion," *P.N.A.S.,* 91:2051–2055, 1994.

Epstein et al., "Expression of yeast hexokinase in pancreatic β cells of transgenic mice reduces blood glucose, enhances insulin secretion, and decresaes diabetes," *Proc. Natl. Acad. Sci. USA,* 89:12038–12042, 1992.

Fanciulli et al., "Glycolysis and Growth Rate in Normal and in Hexokinase–Transfected NIH–3T3 Cells," *Oncology Res.,* 6(9):405–409, 1994.

Felgner and Wilson, "Effect of Neutral Salts on the Interaction of Rat Brain Hexokinase with the Outer Mitochondrial Membrane," *Arch. Bioch. Biophy.,* 182:282–294, 1977.

Ferber et al., "GLUT–2 Gene Transfer into Insulinoma Cells Confers Both Low and High Affinity Glucose–Stimulated Insulin Release," *J. Biol. Chem.,* 269(15):11523–11529, Apr., 1994.

Ferber et al., "Molecular Strategies for the Treatment of Diabetes," *Transplant. Proc.,* 26(2):363–365, Apr., 1994.

Fiedorek et al., "Selective Expression of the Insulin I Gene in Rat Insulinoma–Derived Cell Lines," *Mol. Endocrinol.,* 4(7):990–999, 1990.

Fiek et al., "Evidence for identity between hexokinase–binding protein and the mitochondrial porin in the outer membrane of rat liver mitochondria," *Biochem. Biophys. Acta,* 688:429–440, 1982.

Gazdar et al., "Continuos, Clonal, Insulin– and Somatostatin–Secreting Cell Lines Established from a Transplantable Rat Islet Cell Tumor," *Proc. Natl. Acad. Sci. USA,* 77(6):3519–3523, 1980.

Gelb et al., "Targeting of Hexokinase 1 to Liver and Hepatoma Mitochondria," *Proc. Natl. Acad. Sci. USA,* 89:202–206, 1992.

Gonzalez et al., "Molecular Cloning of CIF1, a Yeast Gene Necessary for Growth on Glucose," *Yeast,* 8:183–192, 1992.

Hosokawa et al., "Upregulated hexokinase activity in isolated islets from diabetic 90 % pancreatectomized rats," *Diabetes* 44:1328–1333, 1995.

Hughes et al., "Engineering of Glucose–Stimulated Insulin Secretion and Biosynthesis in Non–Islet Cells," *Proc. Natl. Acad. Sci. USA,* 89:688–692, Jan., 1992.

Hughes et al., "Expression of Normal and Novel Glucokinase mRNAs in Anterior Pituitary and Islet Cells," *J. Biol. Chem.,* 266(7):4521–4530, Mar., 1991.

Hughes et al., "Transfection of AtT–20$_{ins}$ Cells with GLUT–2 but not GLUT–1 Confers Glucose–Stimulated Insulin Secretions," *J. Biol. Chem.,* 268(20):15205–15212, 1993.

Iynedjian et al., "Differential Expression and Regulation of the Glucokinase Gene in Liver and Islets of Langerhans," *Proc. Natl. Acad. Sci.,* 86:7838–7842, 1989.

Kabir and Wilson, "Mitochondrial Hexokinase in Brain of Various Species: Differences in Sensitivity to Solubilization by Glucose–6–Phosphate," *Arch. Biochem. Biophys.,* 300(2):641–650, 1993.

Kabir and Wilson, "Mitochondrial Hexokinase in Brain: Coexistence of Forms Differing in Sensitivity to Solubilization by Glucose–6–Phosphate on the Same Mitochondria," *Arch. Biochem. Biophys.,* 310(2):410–416, 1994.

Knaack et al., "Clonal Insulinoma Cell Line that Stably Maintains Correct Glucose Responsiveness," *Diabetes,* 43:1413–1417, Dec., 1994.

Kuwajima et al., "The Glucose–Phosphorylating Capacity of Liver as Measured by Three Independent Assays," *J. Biol. Chem.,* 261(19):8849–8853, 1986.

Lacy et al., "Maintenance of Normoglycemia in Diabetic Mice by Subcutaneous Xenografts of Encapsulated Islets," *Science,* 254:1782–1784, Dec., 1991.

Liang, et al., "Glucose regulates glucokinase activity in cultured islets from rat pancreas." *J. Biol. Chem.* 265(28):16863–16866, 1990.

Lindén et al., "Pore Protein and the Hexokinase–Binding Protein from the Outer Membrane Rat Liver Mitochondria are Identical," *FEBS Lett.,* 141(2):189–192, 1982.

Mathupala et al., "Glucose catabolism in cancer cells," *J. Biol. Chem.,* 270(28):16918–16925, 1995.

Miyazaki et al., "Establishment of a Pancreatic β Cell Line that Retains Glucose–Inducible Insulin Secretion: Special Reference to Expression of Glucose Transporter Isoforms," *Endocrinology,* 127(1):126–132, 1990.

Newgard, "Cellular Engineering for the Treatment of Metabolic Disorders: Prospects for Therapy in Diabetes," *Biotechnology,* 10:1112–1120, Oct., 1992.

Newgard, "Perspectives in Diabetes: Cellular Engineering and Gene Therapy Strategies for Insulin Replacement in Diabetes," *Diabetes,* 43:341–350, Mar., 1994.

Newgard and McGarry, "Metabolic Coupling Factors in Pancreatic β–Cell Signal Transduction," *Ann. Rev. Biochem.,* 64:689–719, 1995.

Newgard et al., "Analysis of Glucokinase and Glucose Transporter Gene Products in Islet, Liver, and Anterior Pituitary Cells and Their Role in Glucose Sensing," *Amer. Soc. Biochem. Mol. Biol, Amer. Assoc. Immuno*, New Orleans, Jun. 4–7, p. A2008, Abstract #1827, 1990.

Newgard et al., "Engineering of Glucose–Stimulated Insulin Release in Clonal Cells. Therapeutic Implications," *Diab. Nutr. Metab.*, 5(Suppl. 1):15–20, 1992.

Newgard et al., "Glucokinase and Glucose Transporter Expression in Liver and Islets: Implications for Control of Glucose Homeostasis," *Biochem. Soc. Trans.*, 18:851–853, 1990.

Newgard et al., "Molecular Engineering of Glucose–Regulated Insulin Secretion," In: *Molecular Biology of Diabetes*, Draznin, B. and LeRoith, D.(Eds.), Humana Press Inc., Totowa, N.J., Part 1, Chap. 6:1191–54, 1994.

Newgard et al., "Molecular Engineering of the Pancreatic β–Cell," *J. Labor. Clin. Med.*, 122(4):356–363, 1993.

Polakis and Wilson, "An Intact Hydrophobic N–Terminal Sequence is Critical for Binding of Rat Brain Hexokinase to Mitochondria," *Arch. Biochem. Biophys.*, 236(1):328–337, 1985.

Scharp et al., "Protection of Encapsulated Human Islets Implanted Without Immunosuppression in Patients with Type I or Type II Diabetes and in Nondiabetic Control Subjects," *Diabetes*, 43:1167–1170, Sep., 1994.

Schwab and Wilson, "Complete Amino Acid Sequence of Rat Brain Hexokinase, Deduced from the Cloned cDNA, and Proposed Structure of a Mammalian Hexokinase," *Proc. Natl. Acad. Sci. USA*, 86:2563–2567, 1989.

Schwab and Wilson, "Complete Amino Acid Sequence of the Type III Isozyme of Rat Hexokinase, Deduced from the Cloned cDNA," *Arch. Biochem. Biophys.*, 285(2):365–370, 1991.

Sullivan et al., "Biohybrid Artificial Pancreas: Long–Term Implantation Studies in Diabetic, Pancreatectomized Dogs," *Science*, 252:718–721, May, 1991.

Symons, "Small Catalytic RNAs," *Annu. Rev. Biochem.*, 61:641–671, 1992.

Thelan and Wilson, "Complete Amino Acid Sequence of the Type II Isozyme of Rat Hexokinase, Deduced for the Cloned cDNA: Comparison with a Hexokinase from Novikoff Ascites Tumor," *Arch. Biochem. Biophys.*, 286(2):645–651, 1991.

Tsai and Wilson, "Functional Organization of Mammalian Hexokinases: Characterization of Chimeric Hexokinases Constructed from the N– and C–Terminal Domains of the Rat Type I and Type II Isozymes," Copyright by Academic Press, Inc., 316(1):206–214, 1995.

Weinhouse et al., "Regulation of Glucokinase in Liver," In: *Current Topics in Cellular Regulation*, 11:1–50, 1976.

White and Wilson, "Rat Brain Hexokinase: Location of the Allosteric Regulatory Site in a Structural Domain at the N–Terminus of the Enzyme," *Arch. Bioch. Biophys.*, 259(2):402–411, 1987.

White and Wilson, "Binding of Nucleoside Triphosphates, Inorganic Phosphate, and Other Polyanionic Ligands to the N–Terminal Region of Hexokinase Activity by Antagonistic Interactions Between Glucose 6–Phosphate and Inorganic Phosphate," *Arch. Bioch. Biophys.*, 277(1):26–34, 1990.

Whitesell et al., "Transport and Metabolism of Glucose in an Insulin–Secreting Cell Line, βTC–1," *Biochemistry*, 30(49):11560–11566, 1991.

Wilson, "Brain hexokinase: A proposed relation between soluble–particulate distribution and activity in vivo," *J. Biol. Chem.*, 243(13):3640–3647, 1968.

Wilson, "Hexokinases," In: *Reviews of Physiology, Biochemistry and Pharmacology*, Pette, D. (Ed.), 126:65–174, 1994.

Wilson, "Ligand–induced confirmations of rat brain hexokinase: Effects of glucose–6–phosphate and inorganic phosphate," *Arch. Biochem. Biophys.*, 159:543–549, 1973.

Wilson, "Regulation of mammalian hexokinase activity," In: *Regulation of Carbohydrate Metabolism*, Beitner, R.(Ed.) vol. 1, CRC, Boca Raton, 45–81, 1985.

Xie and Wilson, "Rat brain hexokinase: the hydrophobic N–terminus of the mitochondrially bound enzyme is inserted in the lipid bilayer," *Arch Biochem. Biophys.*, 267(2):803–810,1988.

Cullen and Mains, "Posttranslational Processing of Transfected Mouse Pro–Adenocorticotropin/Endorphin in Rat Growth Hormone–Secreting Tumor Cells," *Endocrinology*, 125(4):1774–1782, 1989.

Moore et al., "Expressing a Human Proinsulin cDNA in a Mouse ACTH–Secreting Cell. Intracellular Storage, Proteolytic Processing, and Secretion on Stimulation," *Cell*, 35:531–538, Dec., 1983.

Santerre et al., "Insulin synthesis in a clonal cell line of simian virus 40–transformed hamster pancreatic beta cells," *Proc. Natl. Acad. Sci. USA*, 78(7):4339–4343, Jul., 1981.

Thorens et al., "Cloning and Functional Expression in Bacteria of a Novel Glucose Transporter Present in Liver, Intestine, Kidney, and β–Pancreatic Islet Cells," *Cell*, 55:281–290, 1988.

Iynedjian et al., "Molecular Cloning of Glucokinase cDNA," *J. Biol. Chem.*, 252:6032–6038, 1987.

Magnuson and Shelton, "An Alternate Promoter in the Glucokinase Gene Is Active in the Pancreatic β Cell," *J. Biol. Chem.*, 264:15936–15942, 1989.

Shimizu et al., "Control of Glucose Metabolism in Pancreatic β–Cells by Glucokinase, Hexokinase, and Phosphofructokinase," *Diabetes*, 37:1524–1530, 1988.

Altman et al., "Long–term plasma glucose normalization in experimental diabetic rats with macroencapsulated implants of benign human insulinomas," *Diabetes*, 35:625–633, Jun., 1986.

O'Shea and Sun, "Encapsulation of rat islets of langerhans prolongs xenograft survival in diabetic mice," *Diabetes*, 35:943–946, Aug., 1986.

Burke, "Clearing the Way for Ribozoymes", *Nature Biotechnology*, 15:414–15, 1997.

Gewirtz et al., "Facilitating Oligonucleotide Delivery: Helping Antisense Deliver on Its Promise," *Proc. Natl. Acad. Sci. USA*, 93:3151–53, 1996.

Rojanasakul, "Antisense Oligonucleotide Therapeutics: Drug Delivery and Targeting," *Advanced Drug Delivery Reviews* 18:115–31, 1996.

Ribozyme IRES Neo
↓

● EP113/1A
● EP113/1B
　 RIN 1046-38

FIG. 4

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
        ( A ) LENGTH: 1534 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

```
CCCGGATCCC  ACATACAGAC  TTATTAAGAC  ATAGAACTAT  GACTACGGAT  AACGCTAAGG      60

CGCAACTGAC  CTCGTCTTCA  GGGGGTAACA  TTATTGTGGT  GTCCAACAGG  CTTCCCGTGA     120

CAATCACTAA  AAACAGCAGT  ACGGGACAGT  ACGAGTACGC  AATGTCGTCC  GGAGGGCTGG     180

TCACGGCGTT  GGAAGGGTTG  AAGAAGACGT  ACACTTTCAA  GTGGTTCGGA  TGGCCTGGGC     240

TAGAGATTCC  TGACGATGAG  AAGGATCAGG  TGAGGAAGGA  CTTGCTGGAA  AAGTTTAATG     300

CCGTACCCAT  CTTCCTGAGC  GATGAAATCG  CAGACTTACA  CTACAACGGG  TTCAGTAATT     360

CTATTCTATG  GCCGTTATTC  CATTACCATC  CTGGTGAGAT  CAATTTCGAC  GAGAATGCGT     420

GGTTCGGATA  CAACGAGGCA  AACCAGACGT  TCACCAACGA  GATTGCTAAG  ACTATGAACC     480

ATAACGATTT  AATCTGGGTG  CATGATTACC  ATTTGATGTT  GGTTCCGGAA  ATGTTGAGAG     540

TCAAGATTCA  CGAGAAGCAA  CTGCAAAACG  TTAAGGTCGG  GTGGTTCCTG  CACACACCAT     600
```

-continued

```
TCCCTTCGAG TGAAATTTAC AGAATTTTAC CTGTCAGACA AGAGATTTTG AAAGGTGTTT      660
TGAGTTGTGA TTTAGTCGGG TTCCACACAT ACGATTATGC AAGACATTTC TTGTCTTCCG      720
TGCAAAGGGT GCTTAACGTG AATACATTGC CTAATGGGGT GGAATACCAG GGCAGATTCG      780
TTAACGTAGG GGCCTTCCCT ATCGGTATCG ACGTGGACAA GTTCACCGAT GGGTTGAAAA      840
AGGAATCCGT ACAAAAGAGA ATCCAGCAAT TGAAGGAAAC TTTCAAGGGC TGCAAGATCA      900
TAGTTGGTGT CGACAGGCTG GATTACATCA AAGGTGTGCC TCAGAAGTTG CACGCCATGG      960
AAGTGTTTCT GAACGAGCAT CCAGAATGGA GGGGCAAGGT TGTTCTGGTA CAGGTTGCAG     1020
TGCCAAGTCG TGGAGATGTG GAAGAGTACC AATATTTAAG ATCTGTGGTC AATGAGTTGG     1080
TCGGTAGAAT CAACGGTCAG TTCGGTACTG TGGAATTCGT CCCCATCCAT TTCATGCACA     1140
AGTCTATACC ATTTGAAGAG CTGATTTCGT TATATGCTGT GAGCGATGTC TGCTTGGTCT     1200
CGTCCACTCG TGATGGTATG AACTTGGTTT CCTACGAATA TATTGCTTGC AAGAAGAAA     1260
AGAAAGGTTC CTTAATCCTG AGTGAGTTCA CAGGTGCCGC ACAATCCCTG AATGGTGCTA     1320
TTATTGTAAA TCCTTGGAAC ACCGATGATC TTTCTGATGC CATCAACGAG GCCTTGACTT     1380
TGCCCGATGT AAAGAAAGAA GTTAACTGGG AAAAACTTTA CAAATACATC TCTAAATACA     1440
CTTCTGCCTT CTGGGGTGAA AATTTCGTCC ATGAATTATA CAGTACATCA TCAAGCTCAA     1500
CAAGCTCCTC TGCCACCAAA AACTGAGGAT CCCG                                 1534
```

( 2 ) INFORMATION FOR SEQ ID NO:2:

( i ) SEQUENCE CHARACTERISTICS:
      ( A ) LENGTH: 495 amino acids
      ( B ) TYPE: amino acid
      ( C ) STRANDEDNESS: single
      ( D ) TOPOLOGY: linear ( x i ) SEQUENCE DESCRIPTION: SEQ ID NO:2:

```
Met Thr Thr Asp Asn Ala Lys Ala Gln Leu Thr Ser Ser Ser Gly Gly
1               5                   10                  15

Asn Ile Ile Val Val Ser Asn Arg Leu Pro Val Thr Ile Thr Lys Asn
            20                  25                  30

Ser Ser Thr Gly Gln Tyr Glu Tyr Ala Met Ser Ser Gly Gly Leu Val
        35                  40                  45

Thr Ala Leu Glu Gly Leu Lys Lys Thr Tyr Thr Phe Lys Trp Phe Gly
    50                  55                  60

Trp Pro Gly Leu Glu Ile Pro Asp Asp Glu Lys Asp Gln Val Arg Lys
65                  70                  75                  80

Asp Leu Leu Glu Lys Phe Asn Ala Val Pro Ile Phe Leu Ser Asp Glu
                85                  90                  95

Ile Ala Asp Leu His Tyr Asn Gly Phe Ser Asn Ser Ile Leu Trp Pro
            100                 105                 110

Leu Phe His Tyr His Pro Gly Glu Ile Asn Phe Asp Glu Asn Ala Trp
        115                 120                 125

Phe Gly Tyr Asn Glu Ala Asn Gln Thr Phe Thr Asn Glu Ile Ala Lys
    130                 135                 140

Thr Met Asn His Asn Asp Leu Ile Trp Val His Asp Tyr His Leu Met
145                 150                 155                 160

Leu Val Pro Glu Met Leu Arg Val Lys Ile His Glu Lys Gln Leu Gln
                165                 170                 175

Asn Val Lys Val Gly Trp Phe Leu His Thr Pro Phe Pro Ser Ser Glu
            180                 185                 190

Ile Tyr Arg Ile Leu Pro Val Arg Gln Glu Ile Leu Lys Gly Val Leu
```

|     |     |     |     | 195 |     |     |     |     | 200 |     |     |     |     | 205 |     |
|-----|-----|-----|-----|-----|-----|-----|-----|-----|-----|-----|-----|-----|-----|-----|-----|
| Ser | Cys 210 | Asp | Leu | Val | Gly | Phe 215 | His | Thr | Tyr | Asp | Tyr 220 | Ala | Arg | His | Phe |
| Leu 225 | Ser | Ser | Val | Gln | Arg 230 | Val | Leu | Asn | Val | Asn 235 | Thr | Leu | Pro | Asn | Gly 240 |
| Val | Glu | Tyr | Gln | Gly 245 | Arg | Phe | Val | Asn | Val 250 | Gly | Ala | Phe | Pro | Ile 255 | Gly |
| Ile | Asp | Val | Asp 260 | Lys | Phe | Thr | Asp | Gly 265 | Leu | Lys | Lys | Glu | Ser 270 | Val | Gln |
| Lys | Arg | Ile 275 | Gln | Gln | Leu | Lys | Glu 280 | Thr | Phe | Lys | Gly | Cys 285 | Lys | Ile | Ile |
| Val | Gly 290 | Val | Asp | Arg | Leu | Asp 295 | Tyr | Ile | Lys | Gly | Val 300 | Pro | Gln | Lys | Leu |
| His 305 | Ala | Met | Glu | Val | Phe 310 | Leu | Asn | Glu | His | Pro 315 | Glu | Trp | Arg | Gly | Lys 320 |
| Val | Val | Leu | Val | Gln 325 | Val | Ala | Val | Pro | Ser 330 | Arg | Gly | Asp | Val | Glu 335 | Glu |
| Tyr | Gln | Tyr | Leu 340 | Arg | Ser | Val | Val | Asn 345 | Glu | Leu | Val | Gly | Arg 350 | Ile | Asn |
| Gly | Gln | Phe 355 | Gly | Thr | Val | Glu | Phe 360 | Val | Pro | Ile | His | Phe 365 | Met | His | Lys |
| Ser | Ile 370 | Pro | Phe | Glu | Glu | Leu 375 | Ile | Ser | Leu | Tyr | Ala 380 | Val | Ser | Asp | Val |
| Cys 385 | Leu | Val | Ser | Ser | Thr 390 | Arg | Asp | Gly | Met | Asn 395 | Leu | Val | Ser | Tyr | Glu 400 |
| Tyr | Ile | Ala | Cys | Gln 405 | Glu | Glu | Lys | Lys | Gly 410 | Ser | Leu | Ile | Leu | Ser 415 | Glu |
| Phe | Thr | Gly | Ala 420 | Ala | Gln | Ser | Leu | Asn 425 | Gly | Ala | Ile | Ile | Val 430 | Asn | Pro |
| Trp | Asn | Thr 435 | Asp | Asp | Leu | Ser | Asp 440 | Ala | Ile | Asn | Glu | Ala 445 | Leu | Thr | Leu |
| Pro | Asp 450 | Val | Lys | Lys | Glu | Val 455 | Asn | Trp | Glu | Lys | Leu 460 | Tyr | Lys | Tyr | Ile |
| Ser 465 | Lys | Tyr | Thr | Ser | Ala 470 | Phe | Trp | Gly | Glu | Asn 475 | Phe | Val | His | Glu | Leu 480 |
| Tyr | Ser | Thr | Ser | Ser 485 | Ser | Ser | Thr | Ser | Ser 490 | Ser | Ala | Thr | Lys | Asn 495 |     |

( 2 ) INFORMATION FOR SEQ ID NO:3:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CTAGACTCCA TGCTCTGATG AGTCCGTGAG GACGAAACGT TCTGGTTCG                    49
```

( 2 ) INFORMATION FOR SEQ ID NO:4:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CTAGATCATG GTCCCCTGAT GAGTCCGTGA GGACGAAACT GTGTCATG                          48
```

(2) INFORMATION FOR SEQ ID NO:5:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:5:

```
CTAGAGTTCC TCCAACTGAT GAGTCCGTGA GGACGAAATC CAAGGCCAG                         49
```

(2) INFORMATION FOR SEQ ID NO:6:

(i) SEQUENCE CHARACTERISTICS:
        (A) LENGTH: 1463 base pairs
        (B) TYPE: nucleic acid
        (C) STRANDEDNESS: single
        (D) TOPOLOGY: linear (xi) SEQUENCE DESCRIPTION: SEQ ID NO:6:

```
GAATTCCGCC GATCTGCCGC TGGAGGACCA CTGCTCACCA GGGCTACTGA GGAGCCACTG              60
GCCCCACACC TGCTTTTCCG CATCCCCCAC CGTCAGCATG ATCGCCGCGC AACTACTGGC             120
CTATTACTTC ACCGAGCTGA AGGATGACCA AGTCAAAAAG ATTGACAAGT ATCTGTACGC             180
CATGCGGCTC TCTGATGAGA TTCTGATAGA TATCCTGACA CGATTCAAGA AAGAGATGAA             240
GAATGGCCTC TCCCGGGATT ATAATCCAAC AGCCTCCGTC AAGATGCTGC CCACCTTGCT             300
CCGGTCCATT CCGGACGGCT CAGAAAGGG GGATTTCATT GCCCTGGATC TCGGCGGGTC              360
TTCCTTTCGA ATCCTGCGGG TGCAGGTGAA CCACGAGAAG AACCAGAACG TCAGCATGGA             420
GTCTGAGATC TACGACACCC CAGAGAACAT CGTGCATGGC AGTGGAACCC AGCTTTTCGA             480
TCATGTCGCT GACTGCCTGG GAGACTTCAT GGAGAAAAAG AAGATCAAGG ACAAGAAGTT             540
ACCCGTGGGA TTCACATTTT CCTTCCCCTG CCGACAATCC AAGATAGATG AGGCTGTACT             600
GATCACGTGG ACAAAGCGGT TCAAAGCCAG TGGCGTGGAA GGAGCGGATG TGGTCAAGTT             660
GCTGAATAAA GCCATTAAGA AGCGAGGGGA CTATGATGCT AACATTGTCG CCGTGGTGAA             720
TGACACAGTA GGGACCATGA TGACCTGCGG TTATGATGAC CAACAGTGTG AAGTCGGCCT             780
GATCATTGGC ACAGGCACCA ATGCTTGCTA CATGGAGGAA CTGCGACACA TCGACCTGGT             840
GGAAGGCGAC GAGGGGAGGA TGTGTATTAA CACGGAATGG GGAGCCTTTG GGGATGATGG             900
GTCCCTGGAA GACATCCGAA CCGAGTTTGA CAGAGAGTTA GACCGTGGAT CTCTCAACCC             960
TGGGAAGCAG CTGTTCGAGA AGATGGTGAG CGGCATGTAC ATGGGGGAGC TGGTCCGGCT            1020
AATCCTGGTG AAGATGGCCA AGGAAGGCCT CTTATTCGAA GGGCGCATCA CTCCAGAGCT            1080
GCTCACGAGG GGAAAGTTCA ACACTAGTGA CGTGTCCGCC ATTGAAAAGG ATAAGGAAGG            1140
CATTCAAAAT GCCAAGGAAA TCTTAACCCG CTTGGGAGTG GAGCCGTCTG ATGTTGACTG            1200
TGTGTCGGTC CAGCACATCT GCACGATCGT CTCCTTCCGA TCAGCCAACC TGGTGGCCGC            1260
CACGCTCGGT GCCATCTTGA ACCGCCTGCG GGACAACAAG GGCACACCCA GCCTGCGGAC            1320
CACGGTTGGC GTGGACGGTT CTCTCTACAA GATGCACCCA CAGTACTCCC GGCGGTTCCA            1380
CAAGACCCTG AGGCGGGTGG TGCCTGACTC CGACGTCCGT TTCCTCCTCT CAGAGAGTGG            1440
CACGGGCAAG GGGGCCGCCA TGG                                                    1463
```

(2) INFORMATION FOR SEQ ID NO:7:

(i) SEQUENCE CHARACTERISTICS:

(A) LENGTH: 455 amino acids
(B) TYPE: amino acid
(C) STRANDEDNESS: single
(D) TOPOLOGY: linear (xi) SEQUENCE DESCRIPTION: SEQ ID NO:7:

```
Met Ile Ala Ala Gln Leu Leu Ala Tyr Tyr Phe Thr Glu Leu Lys Asp
 1               5                  10                  15
Asp Gln Val Lys Lys Ile Asp Lys Tyr Leu Tyr Ala Met Arg Leu Ser
            20                  25                  30
Asp Glu Ile Leu Ile Asp Ile Leu Thr Arg Phe Lys Lys Glu Met Lys
        35                  40                  45
Asn Gly Leu Ser Arg Asp Tyr Asn Pro Thr Ala Ser Val Lys Met Leu
    50                  55                  60
Pro Thr Leu Leu Arg Ser Ile Pro Asp Gly Ser Gly Lys Gly Asp Phe
65                  70                  75                  80
Ile Ala Leu Asp Leu Gly Gly Ser Ser Phe Arg Ile Leu Arg Val Gln
                85                  90                  95
Val Asn His Glu Lys Asn Gln Asn Val Ser Met Glu Ser Glu Ile Tyr
            100                 105                 110
Asp Thr Pro Glu Asn Ile Val His Gly Ser Gly Thr Gln Leu Phe Asp
        115                 120                 125
His Val Ala Asp Cys Leu Gly Asp Phe Met Glu Lys Lys Lys Ile Lys
    130                 135                 140
Asp Lys Lys Leu Pro Val Gly Phe Thr Phe Ser Phe Pro Cys Arg Gln
145                 150                 155                 160
Ser Lys Ile Asp Glu Ala Val Leu Ile Thr Trp Thr Lys Arg Phe Lys
                165                 170                 175
Ala Ser Gly Val Glu Gly Ala Asp Val Val Lys Leu Leu Asn Lys Ala
            180                 185                 190
Ile Lys Lys Arg Gly Asp Tyr Asp Ala Asn Ile Val Ala Val Val Asn
        195                 200                 205
Asp Thr Val Gly Thr Met Met Thr Cys Gly Tyr Asp Asp Gln Gln Cys
    210                 215                 220
Glu Val Gly Leu Ile Ile Gly Thr Gly Thr Asn Ala Cys Tyr Met Glu
225                 230                 235                 240
Glu Leu Arg His Ile Asp Leu Val Glu Gly Asp Glu Gly Arg Met Cys
                245                 250                 255
Ile Asn Thr Glu Trp Gly Ala Phe Gly Asp Asp Gly Ser Leu Glu Asp
            260                 265                 270
Ile Arg Thr Glu Phe Asp Arg Glu Leu Asp Arg Gly Ser Leu Asn Pro
        275                 280                 285
Gly Lys Gln Leu Phe Glu Lys Met Val Ser Gly Met Tyr Met Gly Glu
    290                 295                 300
Leu Val Arg Leu Ile Leu Val Lys Met Ala Lys Glu Gly Leu Leu Phe
305                 310                 315                 320
Glu Gly Arg Ile Thr Pro Glu Leu Leu Thr Arg Gly Lys Phe Asn Thr
                325                 330                 335
Ser Asp Val Ser Ala Ile Glu Lys Asp Lys Glu Gly Ile Gln Asn Ala
            340                 345                 350
Lys Glu Ile Leu Thr Arg Leu Gly Val Glu Pro Ser Asp Val Asp Cys
        355                 360                 365
Val Ser Val Gln His Ile Cys Thr Ile Val Ser Phe Arg Ser Ala Asn
    370                 375                 380
Leu Val Ala Ala Thr Leu Gly Ala Ile Leu Asn Arg Leu Arg Asp Asn
```

|     |     |     |     | 385 |     |     |     |     | 390 |     |     |     |     | 395 |     |     |     |     | 400 |
| --- | --- | --- | --- | --- | --- | --- | --- | --- | --- | --- | --- | --- | --- | --- | --- | --- | --- | --- | --- |
| Lys | Gly | Thr | Pro | Ser | Leu | Arg | Thr | Thr | Val | Gly | Val | Asp | Gly | Ser | Leu |
|     |     |     |     | 405 |     |     |     |     | 410 |     |     |     |     | 415 |     |
| Tyr | Lys | Met | His | Pro | Gln | Tyr | Ser | Arg | Arg | Phe | His | Lys | Thr | Leu | Arg |
|     |     |     | 420 |     |     |     |     | 425 |     |     |     |     | 430 |     |     |
| Arg | Val | Val | Pro | Asp | Ser | Asp | Val | Arg | Phe | Leu | Leu | Ser | Glu | Ser | Gly |
|     |     | 435 |     |     |     |     | 440 |     |     |     |     | 445 |     |     |     |
| Thr | Gly | Lys | Gly | Ala | Ala | Met |
|     | 450 |     |     |     |     | 455 |

( 2 ) INFORMATION FOR SEQ ID NO:8:

( i ) SEQUENCE CHARACTERISTICS:
        ( A ) LENGTH: 2911 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

| | | | | | |
|---|---|---|---|---|---|
| GAATTCCGCC | GATCTGCCGC | TGGAGGACCA | CTGCTCACCA | GGGCTACTGA | GGAGCCACTG | 60 |
| GCCCCACACC | TGCTTTTCCG | CATCCCCCAC | CGTCAGCATG | ATCGCCGCGC | AACTACTGGC | 120 |
| CTATTACTTC | ACCGAGCTGA | AGGATGACCA | AGTCAAAAAG | ATTGACAAGT | ATCTGTACGC | 180 |
| CATGCGGCTC | TCTGATGAGA | TTCTGATAGA | TATCCTGACA | CGATTCAAGA | AAGAGATGAA | 240 |
| GAATGGCCTC | TCCCGGGATT | ATAATCCAAC | AGCCTCCGTC | AAGATGCTGC | CCACCTTGCT | 300 |
| CCGGTCCATT | CCGGACGGCT | CAGAAAAGGG | GGATTTCATT | GCCCTGGATC | TCGGCGGGTC | 360 |
| TTCCTTTCGA | ATCCTGCGGG | TGCAGGTGAA | CCACGAGAAG | AACCAGAACG | TCAGCATGGA | 420 |
| GTCTGAGATC | TACGACACCC | AGAGAACAT | CGTGCATGGC | AGTGGAACCC | AGCTTTTCGA | 480 |
| TCATGTCGCT | GACTGCCTGG | GAGACTTCAT | GGAGAAAAAG | AAGATCAAGG | ACAAGAAGTT | 540 |
| ACCCGTGGGA | TTCACATTTT | CCTTCCCCTG | CCGACAATCC | AAGATAGATG | AGGCTGTACT | 600 |
| GATCACGTGG | ACAAAGCGGT | TCAAAGCCAG | TGGCGTGGAA | GGAGCGGATG | TGGTCAAGTT | 660 |
| GCTGAATAAA | GCCATTAAGA | AGCGAGGGGA | CTATGATGCT | AACATTGTCG | CCGTGGTGAA | 720 |
| TGACACAGTA | GGGACCATGA | TGACCTGCGG | TTATGATGAC | CAACAGTGTG | AAGTCGGCCT | 780 |
| GATCATTGGC | ACAGGCACCA | ATGCTTGCTA | CATGGAGGAA | CTGCGACACA | TCGACCTGGT | 840 |
| GGAAGGCGAC | GAGGGGAGGA | TGTGTATTAA | CACGGAATGG | GGAGCCTTTG | GGGATGATGG | 900 |
| GTCCCTGGAA | GACATCCGAA | CCGAGTTTGA | CAGAGAGTTA | GACCGTGGAT | CTCTCAACCC | 960 |
| TGGGAAGCAG | CTGTTCGAGA | AGATGGTGAG | CGGCATGTAC | ATGGGGAGC | TGGTCCGGCT | 1020 |
| AATCCTGGTG | AAGATGGCCA | AGGAAGGCCT | CTTATTCGAA | GGGCGCATCA | CTCCAGAGCT | 1080 |
| GCTCACGAGG | GGAAAGTTCA | ACACTAGTGA | CGTGTCCGCC | ATTGAAAAGG | ATAAGGAAGG | 1140 |
| CATTCAAAAT | GCCAAGGAAA | TCTTAACCCG | CTTGGGAGTG | GAGCCGTCTG | ATGTTGACTG | 1200 |
| TGTGTCGGTC | CAGCACATCT | GCACGATCGT | CTCCTTCCGA | TCAGCCAACC | TGGTGGCCGC | 1260 |
| CACGCTCGGT | GCCATCTTGA | ACCGCCTGCG | GGACAACAAG | GGCACACCCA | GCCTGCGGAC | 1320 |
| CACGGTTGGC | GTGGACGGTT | CTCTCTACAA | GATGCACCCA | CAGTACTCCC | GGCGGTTCCA | 1380 |
| CAAGACCCTG | AGGCGGGTGG | TGCCTGACTC | CGACGTCCGT | TTCCTCCTCT | CAGAGAGTGG | 1440 |
| CACGGGCAAG | GGGGCCGCCA | TGGCTATGGA | TACTACAAGG | TGTGGAGCCC | AGTTGTTGAC | 1500 |
| TCTGGTCGAG | CAGATCCTGG | CAGAGTTCCA | GCTGCAGGAG | GAAGACCTGA | AGAAGGTGAT | 1560 |
| GAGCCGGATG | CAGAAGGAGA | TGGACCGTGG | CCTGAGGCTG | GAGACCCACG | AGGAGGCCAG | 1620 |
| TGTAAAGATG | TTACCCACCT | ACGTGCGTTC | CACCCCAGAA | GGCTCAGAAG | TCGGAGACTT | 1680 |

```
TCTCTCCTTA GACCTGGGAG GAACCAACTT CAGAGTGATG CTGGTCAAAG TGGGAGAGGG      1740

GGAGGCAGGG CAGTGGAGCG TGAAGACAAA ACACCAGATG TACTCCATCC CCGAGGACGC      1800

CATGACGGGC ACTGCCGAGA TGCTCTTTGA CTACATCTCT GAATGCATCT CTGACTTCCT      1860

TGACAAGCAT CAGATGAAGC ACAAGAAACT GCCCCTGGGC TTCACCTTCT CCTTCCCTGT      1920

GAGGCACGAA GACCTAGACA AGGGCATCCT CCTCAATTGG ACCAAGGGCT TCAAGGCCTC      1980

TGGAGCAGAA GGGAACAACA TCGTAGGACT TCTCCGAGAT GCTATCAAGA GGAGAGGGA      2040

CTTTGAGATG GATGTGGTGG CAATGGTGAA CGACACAGTG GCCACAATGA TCTCCTGCTA      2100

CTATGAAGAC CGCCAATGTG AGGTCGGCAT GATTGTGGGC ACTGGCTGCA ATGCCTGCTA      2160

CATGGAGGAA ATGCAGAATG TGGAGCTGGT GGAAGGGGAT GAGGGACGCA TGTGCGTCAA      2220

CACGGAGTGG GGCGCCTTCG GGGACTCGGG CGAGCTGGAT GAGTTCCTAC TGGAGTATGA      2280

CCGGATGGTG GATGAAAGCT CAGCGAACCC CGGTCAGCAG CTGTACGAGA AGATCATCGG      2340

TGGGAAGTAT ATGGGCGAGC TGGTACGACT TGTGCTGCTT AAGCTGGTGG ACGAGAACCT      2400

TCTGTTCCAC GGAGAGGCCT CGGAGCAGCT GCGCACGCGT GGTGCTTTTG AGACCCGTTT      2460

CGTGTCACAA GTGGAGAGCG ACTCCGGGGA CCGAAAGCAG ATCCACAACA TCCTAAGCAC      2520

TCTGGGGCTT CGACCCTCTG TCACCGACTG CGACATTGTG CGCCGTGCCT GTGAAAGCGT      2580

GTCCACTCGC GCCGCCCATA TGTGCTCCGC AGGACTAGCT GGGGTCATAA ATCGCATGCG      2640

CGAAAGCCGC AGTGAGGACG TGATGCGCAT CACTGTGGGC GTGGATGGCT CCGTGTACAA      2700

GCTGCACCCG AGCTTCAAGG AGCGGTTTCA CGCCAGTGTG CGCAGGCTGA CACCCAACTG      2760

CGAAATCACC TTCATCGAAT CAGAGGAGGG CAGCGGCAGG GGAGCCGCAC TGGTCTCTGC      2820

GGTGGCCTGC AAGAAGGCTT GCATGCTGGC CCAGTGAAAT CCAGGTCATA TGGACCGGGA      2880

CCTGGGTTCC ACGGGGGTTC CACGGGGATC C                                    2911
```

( 2 ) INFORMATION FOR SEQ ID NO:9:

( i ) SEQUENCE CHARACTERISTICS:
    ( A ) LENGTH: 919 amino acids
    ( B ) TYPE: amino acid
    ( C ) STRANDEDNESS: single
    ( D ) TOPOLOGY: linear ( x i ) SEQUENCE DESCRIPTION: SEQ ID NO:9:

```
Met Ile Ala Ala Gln Leu Leu Ala Tyr Tyr Phe Thr Glu Leu Lys Asp
1               5                   10                  15

Asp Gln Val Lys Lys Ile Asp Lys Tyr Leu Tyr Ala Met Arg Leu Ser
            20                  25                  30

Asp Glu Ile Leu Ile Asp Ile Leu Thr Arg Phe Lys Lys Glu Met Lys
        35                  40                  45

Asn Gly Leu Ser Arg Asp Tyr Asn Pro Thr Ala Ser Val Lys Met Leu
    50                  55                  60

Pro Thr Leu Leu Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95

Val Asn His Glu Lys Asn Gln Asn Val Ser Met Glu Ser Glu Ile Tyr
            100                 105                 110

Asp Thr Pro Glu Asn Ile Val His Gly Ser Gly Thr Gln Leu Phe Asp
        115                 120                 125

His Val Ala Asp Cys Leu Gly Asp Phe Met Glu Lys Lys Lys Ile Lys
    130                 135                 140
```

-continued

| Asp | Lys | Lys | Leu | Pro | Val | Gly | Phe | Thr | Phe | Ser | Phe | Pro | Cys | Arg | Gln |
| 145 | | | | 150 | | | | | 155 | | | | | | 160 |

| Ser | Lys | Ile | Asp | Glu | Ala | Val | Leu | Ile | Thr | Trp | Thr | Lys | Arg | Phe | Lys |
| | | | | 165 | | | | | 170 | | | | | 175 | |

| Ala | Ser | Gly | Val | Glu | Gly | Ala | Asp | Val | Lys | Leu | Leu | Asn | Lys | Ala |
| | | | 180 | | | | | 185 | | | | 190 | | |

| Ile | Lys | Lys | Arg | Gly | Asp | Tyr | Asp | Ala | Asn | Ile | Val | Ala | Val | Val | Asn |
| | | 195 | | | | | 200 | | | | | 205 | | | |

| Asp | Thr | Val | Gly | Thr | Met | Met | Thr | Cys | Gly | Tyr | Asp | Asp | Gln | Gln | Cys |
| | 210 | | | | | 215 | | | | | 220 | | | | |

| Glu | Val | Gly | Leu | Ile | Ile | Gly | Thr | Gly | Thr | Asn | Ala | Cys | Tyr | Met | Glu |
| 225 | | | | | 230 | | | | | 235 | | | | | 240 |

| Glu | Leu | Arg | His | Ile | Asp | Leu | Val | Glu | Gly | Asp | Glu | Gly | Arg | Met | Cys |
| | | | | 245 | | | | | 250 | | | | | 255 | |

| Ile | Asn | Thr | Glu | Trp | Gly | Ala | Phe | Gly | Asp | Asp | Gly | Ser | Leu | Glu | Asp |
| | | | 260 | | | | | 265 | | | | 270 | | | |

| Ile | Arg | Thr | Glu | Phe | Asp | Arg | Glu | Leu | Asp | Arg | Gly | Ser | Leu | Asn | Pro |
| | | 275 | | | | | 280 | | | | | 285 | | | |

| Gly | Lys | Gln | Leu | Phe | Glu | Lys | Met | Val | Ser | Gly | Met | Tyr | Met | Gly | Glu |
| | 290 | | | | | 295 | | | | | 300 | | | | |

| Leu | Val | Arg | Leu | Ile | Leu | Val | Lys | Met | Ala | Lys | Glu | Gly | Leu | Leu | Phe |
| 305 | | | | | 310 | | | | | 315 | | | | | 320 |

| Glu | Gly | Arg | Ile | Thr | Pro | Glu | Leu | Leu | Thr | Arg | Gly | Lys | Phe | Asn | Thr |
| | | | | 325 | | | | | 330 | | | | | 335 | |

| Ser | Asp | Val | Ser | Ala | Ile | Glu | Lys | Asp | Lys | Glu | Gly | Ile | Gln | Asn | Ala |
| | | | 340 | | | | | 345 | | | | 350 | | | |

| Lys | Glu | Ile | Leu | Thr | Arg | Leu | Gly | Val | Glu | Pro | Ser | Asp | Val | Asp | Cys |
| | | 355 | | | | | 360 | | | | | 365 | | | |

| Val | Ser | Val | Gln | His | Ile | Cys | Thr | Ile | Val | Ser | Phe | Arg | Ser | Ala | Asn |
| | 370 | | | | | 375 | | | | | 380 | | | | |

| Leu | Val | Ala | Ala | Thr | Leu | Gly | Ala | Ile | Leu | Asn | Arg | Leu | Arg | Asp | Asn |
| 385 | | | | | 390 | | | | | 395 | | | | | 400 |

| Lys | Gly | Thr | Pro | Ser | Leu | Arg | Thr | Thr | Val | Gly | Val | Asp | Gly | Ser | Leu |
| | | | | 405 | | | | | 410 | | | | | 415 | |

| Tyr | Lys | Met | His | Pro | Gln | Tyr | Ser | Arg | Arg | Phe | His | Lys | Thr | Leu | Arg |
| | | | 420 | | | | | 425 | | | | 430 | | | |

| Arg | Val | Val | Pro | Asp | Ser | Asp | Val | Arg | Phe | Leu | Leu | Ser | Glu | Ser | Gly |
| | | 435 | | | | | 440 | | | | | 445 | | | |

| Thr | Gly | Lys | Gly | Ala | Ala | Met | Ala | Met | Asp | Thr | Thr | Arg | Cys | Gly | Ala |
| | 450 | | | | | 455 | | | | | 460 | | | | |

| Gln | Leu | Leu | Thr | Leu | Val | Glu | Gln | Ile | Leu | Ala | Glu | Phe | Gln | Leu | Gln |
| 465 | | | | | 470 | | | | | 475 | | | | | 480 |

| Glu | Glu | Asp | Leu | Lys | Lys | Val | Met | Ser | Arg | Met | Gln | Lys | Glu | Met | Asp |
| | | | | 485 | | | | | 490 | | | | | 495 | |

| Arg | Gly | Leu | Arg | Leu | Glu | Thr | His | Glu | Glu | Ala | Ser | Val | Lys | Met | Leu |
| | | | 500 | | | | | 505 | | | | 510 | | | |

| Pro | Thr | Tyr | Val | Arg | Ser | Thr | Pro | Glu | Gly | Ser | Glu | Val | Gly | Asp | Phe |
| | | 515 | | | | | 520 | | | | | 525 | | | |

| Leu | Ser | Leu | Asp | Leu | Gly | Gly | Thr | Asn | Phe | Arg | Val | Met | Leu | Val | Lys |
| | 530 | | | | | 535 | | | | | 540 | | | | |

| Val | Gly | Glu | Gly | Glu | Ala | Gly | Gln | Trp | Ser | Val | Lys | Thr | Lys | His | Gln |
| 545 | | | | | 550 | | | | | 555 | | | | | 560 |

| Met | Tyr | Ser | Ile | Pro | Glu | Asp | Ala | Met | Thr | Gly | Thr | Ala | Glu | Met | Leu |

|     |     |     |     | 565 |     |     |     | 570 |     |     |     | 575 |     |
| --- | --- | --- | --- | --- | --- | --- | --- | --- | --- | --- | --- | --- | --- |
| Phe | Asp | Tyr | Ile<br>580 | Ser | Glu | Cys | Ile | Ser<br>585 | Asp | Phe | Leu | Asp | His<br>590 | Gln |
| Met | Lys | His<br>595 | Lys | Lys | Leu | Pro | Leu<br>600 | Gly | Phe | Thr | Phe | Ser<br>605 | Phe | Pro | Val |
| Arg | His<br>610 | Glu | Asp | Leu | Asp | Lys<br>615 | Gly | Ile | Leu | Leu | Asn<br>620 | Trp | Thr | Lys | Gly |
| Phe<br>625 | Lys | Ala | Ser | Gly<br>630 | Ala | Glu | Gly | Asn | Asn | Ile<br>635 | Val | Gly | Leu | Leu | Arg<br>640 |
| Asp | Ala | Ile | Lys | Arg<br>645 | Arg | Gly | Asp | Phe | Glu<br>650 | Met | Asp | Val | Val | Ala<br>655 | Met |
| Val | Asn | Asp | Thr<br>660 | Val | Ala | Thr | Met | Ile<br>665 | Ser | Cys | Tyr | Tyr | Glu<br>670 | Asp | Arg |
| Gln | Cys | Glu<br>675 | Val | Gly | Met | Ile | Val<br>680 | Gly | Thr | Gly | Cys | Asn<br>685 | Ala | Cys | Tyr |
| Met | Glu<br>690 | Glu | Met | Gln | Asn | Val<br>695 | Glu | Leu | Val | Glu | Gly<br>700 | Asp | Glu | Gly | Arg |
| Met<br>705 | Cys | Val | Asn | Thr | Glu<br>710 | Trp | Gly | Ala | Phe | Gly<br>715 | Asp | Ser | Gly | Glu | Leu<br>720 |
| Asp | Glu | Phe | Leu | Leu<br>725 | Glu | Tyr | Asp | Arg | Met<br>730 | Val | Asp | Glu | Ser | Ser<br>735 | Ala |
| Asn | Pro | Gly | Gln<br>740 | Gln | Leu | Tyr | Glu | Lys<br>745 | Ile | Ile | Gly | Gly | Lys<br>750 | Tyr | Met |
| Gly | Glu | Leu<br>755 | Val | Arg | Leu | Val | Leu<br>760 | Leu | Lys | Leu | Val | Asp<br>765 | Glu | Asn | Leu |
| Leu | Phe<br>770 | His | Gly | Glu | Ala | Ser<br>775 | Glu | Gln | Leu | Arg | Thr<br>780 | Arg | Gly | Ala | Phe |
| Glu<br>785 | Thr | Arg | Phe | Val | Ser<br>790 | Gln | Val | Glu | Ser | Asp<br>795 | Ser | Gly | Asp | Arg | Lys<br>800 |
| Gln | Ile | His | Asn | Ile<br>805 | Leu | Ser | Thr | Leu | Gly<br>810 | Leu | Arg | Pro | Ser | Val<br>815 | Thr |
| Asp | Cys | Asp | Ile<br>820 | Val | Arg | Arg | Ala | Cys<br>825 | Glu | Ser | Val | Ser | Thr<br>830 | Arg | Ala |
| Ala | His | Met<br>835 | Cys | Ser | Ala | Gly | Leu<br>840 | Ala | Gly | Val | Ile | Asn<br>845 | Arg | Met | Arg |
| Glu | Ser<br>850 | Arg | Ser | Glu | Asp | Val<br>855 | Met | Arg | Ile | Thr | Val<br>860 | Gly | Val | Asp | Gly |
| Ser<br>865 | Val | Tyr | Lys | Leu | His<br>870 | Pro | Ser | Phe | Lys | Glu<br>875 | Arg | Phe | His | Ala | Ser<br>880 |
| Val | Arg | Arg | Leu | Thr<br>885 | Pro | Asn | Cys | Glu | Ile<br>890 | Thr | Phe | Ile | Glu | Ser<br>895 | Glu |
| Glu | Gly | Ser | Gly<br>900 | Arg | Gly | Ala | Ala | Leu<br>905 | Val | Ser | Ala | Val | Ala<br>910 | Cys | Lys |
| Lys | Ala | Cys<br>915 | Met | Leu | Ala | Gln |

( 2 ) INFORMATION FOR SEQ ID NO:10:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CCGGATCCAG  GTCGACGCCG  GCCAAGACAG  CACAGACAGA  TTGACCTATT  GGGGTGTTTC    60

```
GCGAGTGTGA GAGGGAAGCG CCGCGGCCTG TATTTCTAGA CCTGCCCTTC GCCTGGTTCG      120

TGGCGCCTTG TGACCCCGGG CCCCTGCCGC CTGCAAGTCG AAATTGCGCT GTGCTCCTGT      180

GCTACGGCCT GTGGCTGGAC TGCCTGCTGC TGCCCAACTG GCTGGCAAGA TCTCG           235
```

(2) INFORMATION FOR SEQ ID NO:11:

(i) SEQUENCE CHARACTERISTICS:
        (A) LENGTH: 2911 base pairs
        (B) TYPE: nucleic acid
        (C) STRANDEDNESS: single
        (D) TOPOLOGY: linear (xi) SEQUENCE DESCRIPTION: SEQ ID NO:11:

```
GAATTCCGCC GATCTGCCGC TGGAGGACCA CTGCTCACCA GGGCTACTGA GGAGCCACTG       60

GCCCCACACC TGCTTTTCCG CATCCCCCAC CGTCAGCATG ATCGCCGCGC AACTACTGGC      120

CTATTACTTC ACCGAGCTGA AGGATGACCA AGTCAAAAAG ATTGACAAGT ATCTGTACGC      180

CATGCGGCTC TCTGATGAGA TTCTGATAGA TATCCTGACA CGATTCAAGA AAGAGATGAA      240

GAATGGCCTC TCCCGGGATT ATAATCCAAC AGCCTCCGTC AAGATGCTGC CCACCTTGCT      300

CCGGTCCATT CCGGACGGCT CAGAAAAGGG GGATTTCATT GCCCTGGATC TCGGCGGGTC      360

TTCCTTTCGA ATCCTGCGGG TGCAGGTGAA CCACGAGAAG AACCAGAACG TCAGCATGGA      420

GTCTGAGATC TACGACACCC CAGAGAACAT CGTGCATGGC AGTGGAACCC AGCTTTTCGA      480

TCATGTCGCT GACTGCCTGG GAGACTTCAT GGAGAAAAAG AAGATCAAGG ACAAGAAGTT      540

ACCCGTGGGA TTCACATTTT CCTTCCCCTG CCGACAATCC AAGATAGATG AGGCTGTACT      600

GATCACGTGG ACAAAGCGGT TCAAAGCCAG TGGCGTGGAA GGAGCGGATG TGGTCAAGTT      660

GCTGAATAAA GCCATTAAGA AGCGAGGGGA CTATGATGCT AACATTGTCG CCGTGGTGAA      720

TGACACAGTA GGGACCATGA TGACCTGCGG TTATGATGAC CAACAGTGTG AAGTCGGCCT      780

GATCATTGGC ACAGGCACCA ATGCTTGCTA CATGGAGGAA CTGCGACACA TCGACCTGGT      840

GGAAGGCGAC GAGGGGAGGA TGTGTATTAA CACGGAATGG GGAGCCTTTG GGATGATGG       900

GTCCCTGGAA GACATCCGAA CCGAGTTTGA CAGAGAGTTA GACCGTGGAT CTCTCAACCC      960

TGGGAAGCAG CTGTTCGAGA AGATGGTGAG CGGCATGTAC ATGGGGGAGC TGGTCCGGCT     1020

AATCCTGGTG AAGATGGCCA AGGAAGGCCT CTTATTCGAA GGGCGCATCA CTCCAGAGCT     1080

GCTCACGAGG GGAAAGTTCA ACACTAGTGA CGTGTCCGCC ATTGAAAAGG ATAAGGAAGG     1140

CATTCAAAAT GCCAAGGAAA TCTTAACCCG CTTGGGAGTG GAGCCGTCTG ATGTTGACTG     1200

TGTGTCGGTC CAGCACATCT GCACGATCGT CTCCTTCCGA TCAGCCAACC TGGTGGCCGC     1260

CACGCTCGGT GCCATCTTGA ACCGCCTGCG GGACAACAAG GCACACCCA GCCTGCGGAC      1320

CACGGTTGGC GTGGACGGTT CTCTCTACAA GATGCACCCA CAGTACTCCC GGCGGTTCCA     1380

CAAGACCCTG AGGCGGGTGG TGCCTGACTC CGACGTCCGT TTCCTCCTCT CAGAGAGTGG     1440

CACGGGCAAG GGGGCCGCCA TGGTGGATGA CAGAGCCAGG ATGGAGGCCA CCAAGAAGGA     1500

AAAGGTCGAG CAGATCCTGG CAGAGTTCCA GCTGCAGGAG GAAGACCTGA AGAAGGTGAT     1560

GAGCCGGATG CAGAAGGAGA TGGACCGTGG CCTGAGGCTG GAGACCCACG AGGAGGCCAG     1620

TGTAAAGATG TTACCCACCT ACGTGCGTTC CACCCCAGAA GGCTCAGAAG TCGGAGACTT     1680

TCTCTCCTTA GACCTGGGAG GAACCAACTT CAGAGTGATG CTGGTCAAAG TGGGAGAGGG     1740

GGAGGCAGGG CAGTGGAGCG TGAAGACAAA ACACCAGATG TACTCCATCC CCGAGGACGC     1800

CATGACGGGC ACTGCCGAGA TGCTCTTTGA CTACATCTCT GAATGCATCT CTGACTTCCT     1860
```

| | | | | | |
|---|---|---|---|---|---|
| TGACAAGCAT | CAGATGAAGC | ACAAGAAACT | GCCCCTGGGC | TTCACCTTCT | CCTTCCCTGT | 1920 |
| GAGGCACGAA | GACCTAGACA | AGGGCATCCT | CCTCAATTGG | ACCAAGGGCT | TCAAGGCCTC | 1980 |
| TGGAGCAGAA | GGGAACAACA | TCGTAGGACT | TCTCCGAGAT | GCTATCAAGA | GGAGAGGGGA | 2040 |
| CTTTGAGATG | GATGTGGTGG | CAATGGTGAA | CGACACAGTG | GCCACAATGA | TCTCCTGCTA | 2100 |
| CTATGAAGAC | CGCCAATGTG | AGGTCGGCAT | GATTGTGGGC | ACTGGCTGCA | ATGCCTGCTA | 2160 |
| CATGGAGGAA | ATGCAGAATG | TGGAGCTGGT | GGAAGGGGAT | GAGGGACGCA | TGTGCGTCAA | 2220 |
| CACGGAGTGG | GGCGCCTTCG | GGGACTCGGG | CGAGCTGGAT | GAGTTCCTAC | TGGAGTATGA | 2280 |
| CCGGATGGTG | GATGAAAGCT | CAGCGAACCC | CGGTCAGCAG | CTGTACGAGA | AGATCATCGG | 2340 |
| TGGAAGTAT | ATGGGCGAGC | TGGTACGACT | TGTGCTGCTT | AAGCTGGTGG | ACGAGAACCT | 2400 |
| TCTGTTCCAC | GGAGAGGCCT | CGGAGCAGCT | GCGCACGCGT | GGTGCTTTTG | AGACCCGTTT | 2460 |
| CGTGTCACAA | GTGGAGAGCG | ACTCCGGGGA | CCGAAAGCAG | ATCCACAACA | TCCTAAGCAC | 2520 |
| TCTGGGGCTT | CGACCCTCTG | TCACCGACTG | CGACATTGTG | CGCCGTGCCT | GTGAAAGCGT | 2580 |
| GTCCACTCGC | GCCGCCCATA | TGTGCTCCGC | AGGACTAGCT | GGGGTCATAA | ATCGCATGCG | 2640 |
| CGAAAGCCGC | AGTGAGGACG | TGATGCGCAT | CACTGTGGGC | GTGGATGGCT | CCGTGTACAA | 2700 |
| GCTGCACCCG | AGCTTCAAGG | AGCGGTTTCA | CGCCAGTGTG | CGCAGGCTGA | CACCCAACTG | 2760 |
| CGAAATCACC | TTCATCGAAT | CAGAGGAGGG | CAGCGGCAGG | GGAGCCGCAC | TGGTCTCTGC | 2820 |
| GGTGGCCTGC | AAGAAGGCTT | GCATGCTGGC | CCAGTGAAAT | CCAGGTCATA | TGGACCGGGA | 2880 |
| CCTGGGTTCC | ACGGGGGTTC | CACGGGGATC | C | | | 2911 |

(2) INFORMATION FOR SEQ ID NO:12:

(i) SEQUENCE CHARACTERISTICS:
        (A) LENGTH: 919 amino acids
        (B) TYPE: amino acid
        (C) STRANDEDNESS: single
        (D) TOPOLOGY: linear (xi) SEQUENCE DESCRIPTION: SEQ ID NO:12:

```
Met Ile Ala Ala Gln Leu Leu Ala Tyr Tyr Phe Thr Glu Leu Lys Asp
  1               5                  10                  15

Asp Gln Val Lys Lys Ile Asp Lys Tyr Leu Tyr Ala Met Arg Leu Ser
              20                  25                  30

Asp Glu Ile Leu Ile Asp Ile Leu Thr Arg Phe Lys Lys Glu Met Lys
          35                  40                  45

Asn Gly Leu Ser Arg Asp Tyr Asn Pro Thr Ala Ser Val Lys Met Leu
      50                  55                  60

Pro Thr Leu Leu Arg Ser Ile Pro Asp Gly Ser Glu Lys Gly Asp Phe
 65                  70                  75                  80

Ile Ala Leu Asp Leu Gly Gly Ser Ser Phe Arg Ile Leu Arg Val Gln
                  85                  90                  95

Val Asn His Glu Lys Asn Gln Asn Val Ser Met Glu Ser Glu Ile Tyr
             100                 105                 110

Asp Thr Pro Glu Asn Ile Val His Gly Ser Gly Thr Gln Leu Phe Asp
         115                 120                 125

His Val Ala Asp Cys Leu Gly Asp Phe Met Glu Lys Lys Lys Ile Lys
     130                 135                 140

Asp Lys Lys Leu Pro Val Gly Phe Thr Phe Ser Phe Pro Cys Arg Gln
145                 150                 155                 160

Ser Lys Ile Asp Glu Ala Val Leu Ile Thr Trp Thr Lys Arg Phe Lys
                 165                 170                 175
```

```
Ala  Ser  Gly  Val  Glu  Gly  Ala  Asp  Val  Val  Lys  Leu  Leu  Asn  Lys  Ala
               180                 185                      190

Ile  Lys  Lys  Arg  Gly  Asp  Tyr  Asp  Ala  Asn  Ile  Val  Ala  Val  Val  Asn
          195                      200                 205

Asp  Thr  Val  Gly  Thr  Met  Met  Thr  Cys  Gly  Tyr  Asp  Asp  Gln  Gln  Cys
     210                      215                      220

Glu  Val  Gly  Leu  Ile  Ile  Gly  Thr  Gly  Thr  Asn  Ala  Cys  Tyr  Met  Glu
225                      230                 235                           240

Glu  Leu  Arg  His  Ile  Asp  Leu  Val  Glu  Gly  Asp  Glu  Gly  Arg  Met  Cys
               245                      250                      255

Ile  Asn  Thr  Glu  Trp  Gly  Ala  Phe  Gly  Asp  Asp  Gly  Ser  Leu  Glu  Asp
               260                 265                      270

Ile  Arg  Thr  Glu  Phe  Asp  Arg  Glu  Leu  Asp  Arg  Gly  Ser  Leu  Asn  Pro
          275                      280                 285

Gly  Lys  Gln  Leu  Phe  Glu  Lys  Met  Val  Ser  Gly  Met  Tyr  Met  Gly  Glu
     290                      295                 300

Leu  Val  Arg  Leu  Ile  Leu  Val  Lys  Met  Ala  Lys  Glu  Gly  Leu  Leu  Phe
305                      310                 315                           320

Glu  Gly  Arg  Ile  Thr  Pro  Glu  Leu  Leu  Thr  Arg  Gly  Lys  Phe  Asn  Thr
               325                      330                      335

Ser  Asp  Val  Ser  Ala  Ile  Glu  Lys  Asp  Lys  Glu  Gly  Ile  Gln  Asn  Ala
               340                      345                 350

Lys  Glu  Ile  Leu  Thr  Arg  Leu  Gly  Val  Glu  Pro  Ser  Asp  Val  Asp  Cys
          355                      360                 365

Val  Ser  Val  Gln  His  Ile  Cys  Thr  Ile  Val  Ser  Phe  Arg  Ser  Ala  Asn
     370                      375                 380

Leu  Val  Ala  Ala  Thr  Leu  Gly  Ala  Ile  Leu  Asn  Arg  Leu  Arg  Asp  Asn
385                      390                 395                           400

Lys  Gly  Thr  Pro  Ser  Leu  Arg  Thr  Thr  Val  Gly  Val  Asp  Gly  Ser  Leu
               405                      410                      415

Tyr  Lys  Met  His  Pro  Gln  Tyr  Ser  Arg  Arg  Phe  His  Lys  Thr  Leu  Arg
               420                      425                      430

Arg  Val  Val  Pro  Asp  Ser  Asp  Val  Arg  Phe  Leu  Leu  Ser  Glu  Ser  Gly
          435                      440                      445

Thr  Gly  Lys  Gly  Ala  Ala  Met  Val  Asp  Asp  Arg  Ala  Arg  Met  Glu  Ala
     450                      455                      460

Thr  Lys  Lys  Glu  Lys  Val  Glu  Gln  Ile  Leu  Ala  Glu  Phe  Gln  Leu  Gln
465                      470                      475                      480

Glu  Glu  Asp  Leu  Lys  Lys  Val  Met  Ser  Arg  Met  Gln  Lys  Glu  Met  Asp
               485                      490                      495

Arg  Gly  Leu  Arg  Leu  Glu  Thr  His  Glu  Glu  Ala  Ser  Val  Lys  Met  Leu
               500                      505                      510

Pro  Thr  Tyr  Val  Arg  Ser  Thr  Pro  Glu  Gly  Ser  Glu  Val  Gly  Asp  Phe
          515                      520                      525

Leu  Ser  Leu  Asp  Leu  Gly  Gly  Thr  Asn  Phe  Arg  Val  Met  Leu  Val  Lys
     530                      535                      540

Val  Gly  Glu  Gly  Glu  Ala  Gly  Gln  Trp  Ser  Val  Lys  Thr  Lys  His  Gln
545                      550                      555                      560

Met  Tyr  Ser  Ile  Pro  Glu  Asp  Ala  Met  Thr  Gly  Thr  Ala  Glu  Met  Leu
               565                      570                      575

Phe  Asp  Tyr  Ile  Ser  Glu  Cys  Ile  Ser  Asp  Phe  Leu  Asp  Lys  His  Gln
               580                      585                      590

Met  Lys  His  Lys  Lys  Leu  Pro  Leu  Gly  Phe  Thr  Phe  Ser  Phe  Pro  Val
          595                      600                      605
```

| | | | | | | | | | | | | | | |
|---|---|---|---|---|---|---|---|---|---|---|---|---|---|---|
| Arg | His | Glu | Asp | Leu | Asp | Lys | Gly | Ile | Leu | Leu | Asn | Trp | Thr | Lys | Gly |
| | 610 | | | | 615 | | | | | 620 | | | | | |
| Phe | Lys | Ala | Ser | Gly | Ala | Glu | Gly | Asn | Asn | Ile | Val | Gly | Leu | Leu | Arg |
| 625 | | | | | 630 | | | | 635 | | | | | | 640 |
| Asp | Ala | Ile | Lys | Arg | Arg | Gly | Asp | Phe | Glu | Met | Asp | Val | Val | Ala | Met |
| | | | | 645 | | | | | 650 | | | | | 655 | |
| Val | Asn | Asp | Thr | Val | Ala | Thr | Met | Ile | Ser | Cys | Tyr | Tyr | Glu | Asp | Arg |
| | | | 660 | | | | | 665 | | | | | 670 | | |
| Gln | Cys | Glu | Val | Gly | Met | Ile | Val | Gly | Thr | Gly | Cys | Asn | Ala | Cys | Tyr |
| | | 675 | | | | | 680 | | | | | 685 | | | |
| Met | Glu | Glu | Met | Gln | Asn | Val | Glu | Leu | Val | Glu | Gly | Asp | Glu | Gly | Arg |
| | 690 | | | | 695 | | | | | 700 | | | | | |
| Met | Cys | Val | Asn | Thr | Glu | Trp | Gly | Ala | Phe | Gly | Asp | Ser | Gly | Glu | Leu |
| 705 | | | | | 710 | | | | 715 | | | | | | 720 |
| Asp | Glu | Phe | Leu | Leu | Glu | Tyr | Asp | Arg | Met | Val | Asp | Glu | Ser | Ser | Ala |
| | | | | 725 | | | | | 730 | | | | | 735 | |
| Asn | Pro | Gly | Gln | Gln | Leu | Tyr | Glu | Lys | Ile | Ile | Gly | Gly | Lys | Tyr | Met |
| | | | 740 | | | | | 745 | | | | | 750 | | |
| Gly | Glu | Leu | Val | Arg | Leu | Val | Leu | Leu | Lys | Leu | Val | Asp | Glu | Asn | Leu |
| | | 755 | | | | | 760 | | | | | 765 | | | |
| Leu | Phe | His | Gly | Glu | Ala | Ser | Glu | Gln | Leu | Arg | Thr | Arg | Gly | Ala | Phe |
| | 770 | | | | | 775 | | | | | 780 | | | | |
| Glu | Thr | Arg | Phe | Val | Ser | Gln | Val | Glu | Ser | Asp | Ser | Gly | Asp | Arg | Lys |
| 785 | | | | | 790 | | | | 795 | | | | | | 800 |
| Gln | Ile | His | Asn | Ile | Leu | Ser | Thr | Leu | Gly | Leu | Arg | Pro | Ser | Val | Thr |
| | | | | 805 | | | | | 810 | | | | | 815 | |
| Asp | Cys | Asp | Ile | Val | Arg | Arg | Ala | Cys | Glu | Ser | Val | Ser | Thr | Arg | Ala |
| | | | 820 | | | | | 825 | | | | | 830 | | |
| Ala | His | Met | Cys | Ser | Ala | Gly | Leu | Ala | Gly | Val | Ile | Asn | Arg | Met | Arg |
| | | 835 | | | | | 840 | | | | | 845 | | | |
| Glu | Ser | Arg | Ser | Glu | Asp | Val | Met | Arg | Ile | Thr | Val | Gly | Val | Asp | Gly |
| | 850 | | | | | 855 | | | | | 860 | | | | |
| Ser | Val | Tyr | Lys | Leu | His | Pro | Ser | Phe | Lys | Glu | Arg | Phe | His | Ala | Ser |
| 865 | | | | | 870 | | | | 875 | | | | | | 880 |
| Val | Arg | Arg | Leu | Thr | Pro | Asn | Cys | Glu | Ile | Thr | Phe | Ile | Glu | Ser | Glu |
| | | | | 885 | | | | | 890 | | | | | 895 | |
| Glu | Gly | Ser | Gly | Arg | Gly | Ala | Ala | Leu | Val | Ser | Ala | Val | Ala | Cys | Lys |
| | | | 900 | | | | | 905 | | | | | 910 | | |
| Lys | Ala | Cys | Met | Leu | Ala | Gln | | | | | | | | | |
| | | 915 | | | | | | | | | | | | | |

(2) INFORMATION FOR SEQ ID NO:13:

(i) SEQUENCE CHARACTERISTICS:
  (A) LENGTH: 3647 base pairs
  (B) TYPE: nucleic acid
  (C) STRANDEDNESS: single
  (D) TOPOLOGY: linear (xi) SEQUENCE DESCRIPTION: SEQ ID NO:13:

| | | | | | | |
|---|---|---|---|---|---|---|
| CGCCGATCTG | CCGCTGGAGG | ACCACTGCTC | ACCAGGGCTA | CTGAGGAGCC | ACTGGCCCCA | 60 |
| CACCTGCTTT | TCCGCATCCC | CCACCGTCAG | CATGATCGCC | GCGCAACTAC | TGGCCTATTA | 120 |
| CTTCACCGAG | CTGAAGGATG | ACCAAGTCAA | AAAGATTGAC | AAGTATCTGT | ACGCCATGCG | 180 |
| GCTCTCTGAT | GAGATTCTGA | TAGATATCCT | GACACGATTC | AAGAAAGAGA | TGAAGAATGG | 240 |

-continued

| | | | | | | |
|---|---|---|---|---|---|---|
|CCTCTCCCGG|GATTATAATC|CAACAGCCTC|CGTCAAGATG|CTGCCCACCT|TGCTCCGGTC|300|
|CATTCCGGAC|GGCTCAGAAA|AGGGGGATTT|CATTGCCCTG|GATCTCGGCG|GGTCTTCCTT|360|
|TCGAATCCTG|CGGGTGCAGG|TGAACCACGA|GAAGAACCAG|AACGTCAGCA|TGGAGTCTGA|420|
|GATCTACGAC|ACCCCAGAGA|ACATCGTGCA|TGGCAGTGGA|ACCCAGCTTT|TCGATCATGT|480|
|CGCTGACTGC|CTGGGAGACT|TCATGGAGAA|AAAGAAGATC|AAGGACAAGA|AGTTACCCGT|540|
|GGGATTCACA|TTTTCCTTCC|CCTGCCGACA|ATCCAAGATA|GATGAGGCTG|TACTGATCAC|600|
|GTGGACAAAG|CGGTTCAAAG|CCAGTGGCGT|GGAAGGAGCG|GATGTGGTCA|AGTTGCTGAA|660|
|TAAAGCCATT|AAGAAGCGAG|GGACTATGA|TGCTAACATT|GTCGCCGTGG|TGAATGACAC|720|
|AGTAGGGACC|ATGATGACCT|GCGGTTATGA|TGACCAACAG|TGTGAAGTCG|GCCTGATCAT|780|
|TGGCACAGGC|ACCAATGCTT|GCTACATGGA|GGAACTGCGA|CACATCGACC|TGGTGGAAGG|840|
|CGACGAGGGG|AGGATGTGTA|TTAACACGGA|ATGGGGAGCC|TTTGGGGATG|ATGGGTCCCT|900|
|GGAAGACATC|CGAACCGAGT|TTGACAGAGA|GTTAGACGT|GGATCTCTCA|ACCCTGGGAA|960|
|GCAGCTGTTC|GAGAAGATGG|TGAGCGGCAT|GTACATGGGG|GAGCTGGTCC|GGCTAATCCT|1020|
|GGTGAAGATG|GCCAAGGAAG|GCCTCTTATT|CGAAGGGCGC|ATCACTCCAG|AGCTGCTCAC|1080|
|GAGGGGAAAG|TTCAACACTA|GTGACGTGTC|CGCCATTGAA|AAGGATAAGG|AAGGCATTCA|1140|
|AAATGCCAAG|GAAATCTTAA|CCCGCTTGGG|AGTGGAGCCG|TCTGATGTTG|ACTGTGTGTC|1200|
|GGTCCAGCAC|ATCTGCACGA|TCGTCTCCTT|CCGATCAGCC|AACCTGGTGG|CCGCCACGCT|1260|
|CGGTGCCATC|TTGAACCGCC|TGCGGGACAA|CAAGGGCACA|CCCAGCCTGC|GGACCACGGT|1320|
|TGGCGTGGAC|GGTTCTCTCT|ACAAGATGCA|CCCACAGTAC|TCCCGGCGGT|TCCACAAGAC|1380|
|CCTGAGGCGG|GTGGTGCCTG|ACTCCGACGT|CCGTTTCCTC|CTCTCAGAGA|GTGGCACGGG|1440|
|CAAGGGGGCC|GCCATGGTGA|CGGCAGTAGC|CTACCGCCTG|GCTGAGCAGC|ACCGGCAGAT|1500|
|TGAGGAAACC|CTGGCCCACT|TCCGCCTCAG|CAAGCAGACG|CTGATGGAGG|TGAAGAAGAG|1560|
|GCTACGGACA|GAGATGGAAA|TGGGGCTGAG|GAAGGAGACC|AACAGCAAAG|CTACTGTCAA|1620|
|AATGCTGCCT|TCTTTTGTCC|GGAGCATCCC|GGATGGGACT|GAACACGGTG|ACTTCCTGGC|1680|
|CTTGGATCTT|GGAGGAACGA|ATTTCCGGGT|TCTGCTGGTA|AAGATCCGCA|GTGGGAAAAA|1740|
|GAGAACAGTG|GAAATGCACA|ACAAGATCTA|CTCCATTCCC|CTGGAAATCA|TGCAGGGCAC|1800|
|CGGGGATGAG|CTGTTTGACC|ACATCGTCTC|CTGCATCTCT|GACTTCCTGG|ACTACATGGG|1860|
|GATCAAAGGC|CCCCGGATGC|CTCTGGGCTT|CACCTTCTCA|TTTCCCTGCC|ATCAGACGAA|1920|
|CCTGGACTGT|GGAATCTTGA|TCTCATGGAC|AAAGGGTTTC|AAAGCCACTG|ACTGTGAGGG|1980|
|CCATGATGTA|GCCTCCTTAC|TGAGGGATGC|GGTGAAGAGG|AGAGAGGAAT|TTGACTTGGA|2040|
|TGTGGTGGCT|GTGGTCAACG|ACACCGTGGG|CACCATGATG|ACCTGTGCGT|ATGAAGAACC|2100|
|CACTTGCGAA|ATTGGACTCA|TCGTGGGGAC|GGGCACCAAT|GCCTGCTACA|TGGAGGAGAT|2160|
|GAAGAATGTG|GAGATGGTGG|AGGGAACCA|GGGCCAGATG|TGCATCAACA|TGGAGTGGGG|2220|
|CGCCTTCGGT|GACAATGGGT|GTCTGGATGA|CATCAGAACA|GACTTTGACA|AAGTGGTGGA|2280|
|CGAATATTCT|CTAAACTCTG|GGAAACAAAG|GTTTGAGAAA|ATGATCAGTG|GGATGTACCT|2340|
|GGGTGAGATC|GTCCGTAACA|TCCTGATTGA|CTTCACCAAG|AAAGGCTTCC|TCTTCCGGGG|2400|
|ACAGATCTCC|GAACCACTCA|AGACCCGAGG|CATCTTTGAG|ACCAAGTTTC|TCTCTCAGAT|2460|
|TGAGAGTGAC|CGGTTAGCGC|TGCTCCAGGT|GCGGGCCATC|CTTCAGCAGC|TGGGTTTGAA|2520|
|CAGCACGTGT|GACGACAGTA|TCCTGGTCAA|GACCGTGTGT|GGGGTGGTGT|CCAAGAGGGC|2580|
|GGCTCAGCTG|TGTGGTGCCG|GCATGGCCGC|CGTGGTGGAA|AAGATCAGAG|AGAACAGAGG|2640|

-continued

```
CCTAGACCAT CTGAATGTAA CTGTGGGAGT GGATGGGACG CTCTACAAAC TTCATCCACA      2700

CTTCTCCAGA ATCATGCACC AAACTGTGAA GGAACTGTCA CCAAAGTGTA CCGTGTCCTT      2760

CCTCCTGTCT GAAGACGGCA GCGGCAAGGG GGCCGCCCTT ATCACAGCTG TGGGCGTGCG      2820

GCTCAGAGGA GACCCTTCGA TCGCCTAAAA GCCAGGATCC TCCCAGCCCC CAGCCCGCCA      2880

CCCTTCCAGC ACTCCTCTCT AGAACCGACG ACCACACCCC CGTGTTCCAC CCAGCAAGCC      2940

CTGGGAGACC CAGCCAGCGC CCACTCCGCC GCAGCAGAGG GAGGAAGGGG ACCGCAGTAA      3000

CGGAGCACCA CGTAGAATAC CACCCAGAGC GCGTGTGCTG TTGATCTGAT CTCTCGCCTG      3060

GACCCCTAAT CCCTGCCCTG CCACTCTGCA TGATTCAAGT TCGACCTGGC CATGCATTGC      3120

CCATGAGTGA ACGTAGCGGC ACCCCGGTGC GTCTACTGCA GATGTCCAGC TAGGAAAGAG      3180

TCCCCTCTCT TGGACAGTCT TCTGGGCCCT TCCAAGCCCA TCCGTGGAGT CGGCCTCTCC      3240

TCCCCTCTCC CCCGTGTGAA GTGTGTTATC ACCAGCAGAC ACTGCCGGAC TCCTGCCCAC      3300

AGGGGCGTGG CCTGAAGGCG GAGTGTGGAC ATGGCACTGC TGTTCCGTTC CCTTCCCCTC      3360

CCAGCACCCG CCGCAGCCTG CCATCCCGTC TGGATGTATC GATGCCACAG AATTGTGAAT      3420

TGTGTGTCCG TCCGTGGAGC CAGTCCTAGC CACATTATTG ACAGTCTTGC ATTTGTTTT      3480

GTCTCCTGGT GGTGGGGGTG GAGGTGGTAG GGGTGCGCTA AGGTGGGCAG TCCTGTGGGA      3540

GAACATCTTG CTAGAAGGAA CCAACCCACG AAACAACACC ATCACTGGAA TTTCCCATCG      3600

CTTTAGTGAG CCATTGTTGT ACGTCTAGTA AACTTTGTAC TGATTCA                    3647
```

(2) INFORMATION FOR SEQ ID NO:14:

(i) SEQUENCE CHARACTERISTICS:
        (A) LENGTH: 918 amino acids
        (B) TYPE: amino acid
        (C) STRANDEDNESS: single
        (D) TOPOLOGY: linear (xi) SEQUENCE DESCRIPTION: SEQ ID NO:14:

```
Met Ile Ala Ala Gln Leu Leu Ala Tyr Tyr Phe Thr Glu Leu Lys Asp
 1               5                  10                  15

Asp Gln Val Lys Ile Asp Lys Tyr Leu Tyr Ala Met Arg Leu Ser
            20                  25                  30

Asp Glu Ile Leu Ile Asp Ile Leu Thr Arg Phe Lys Lys Glu Met Lys
        35                  40                  45

Asn Gly Leu Ser Arg Asp Tyr Asn Pro Thr Ala Ser Val Lys Met Leu
    50                  55                  60

Pro Thr Leu Leu Arg Ser Ile Pro Asp Gly Ser Glu Lys Gly Asp Phe
65                  70                  75                  80

Ile Ala Leu Asp Leu Gly Gly Ser Ser Phe Arg Ile Leu Arg Val Gln
                85                  90                  95

Val Asn His Glu Lys Asn Gln Asn Val Ser Met Glu Ser Glu Ile Tyr
            100                 105                 110

Asp Thr Pro Glu Asn Ile Val His Gly Ser Gly Thr Gln Leu Phe Asp
        115                 120                 125

His Val Ala Asp Cys Leu Gly Asp Phe Met Glu Lys Lys Ile Lys
    130                 135                 140

Asp Lys Lys Leu Pro Val Gly Phe Thr Phe Ser Phe Pro Cys Arg Gln
145                 150                 155                 160

Ser Lys Ile Asp Glu Ala Val Leu Ile Thr Trp Thr Lys Arg Phe Lys
                165                 170                 175

Ala Ser Gly Val Glu Gly Ala Asp Val Val Lys Leu Leu Asn Lys Ala
            180                 185                 190
```

| | | | | | | | | | | | | | | |
|---|---|---|---|---|---|---|---|---|---|---|---|---|---|---|
| Ile | Lys | Lys 195 | Arg | Gly | Asp | Tyr | Asp 200 | Ala | Asn | Ile | Val | Ala 205 | Val | Val | Asn |
| Asp | Thr 210 | Val | Gly | Thr | Met | Met 215 | Thr | Cys | Gly | Tyr | Asp 220 | Asp | Gln | Gln | Cys |
| Glu 225 | Val | Gly | Leu | Ile | Ile 230 | Gly | Thr | Gly | Thr | Asn 235 | Ala | Cys | Tyr | Met | Glu 240 |
| Glu | Leu | Arg | His | Ile 245 | Asp | Leu | Val | Glu | Gly 250 | Asp | Glu | Gly | Arg | Met 255 | Cys |
| Ile | Asn | Thr | Glu 260 | Trp | Gly | Ala | Phe | Gly 265 | Asp | Asp | Gly | Ser | Leu 270 | Glu | Asp |
| Ile | Arg | Thr 275 | Glu | Phe | Asp | Arg | Glu 280 | Leu | Asp | Arg | Gly | Ser 285 | Leu | Asn | Pro |
| Gly | Lys 290 | Gln | Leu | Phe | Glu | Lys 295 | Met | Val | Ser | Gly | Met 300 | Tyr | Met | Gly | Glu |
| Leu 305 | Val | Arg | Leu | Ile | Leu 310 | Val | Lys | Met | Ala | Lys 315 | Glu | Gly | Leu | Leu | Phe 320 |
| Glu | Gly | Arg | Ile | Thr 325 | Pro | Glu | Leu | Leu | Thr 330 | Arg | Gly | Lys | Phe | Asn 335 | Thr |
| Ser | Asp | Val | Ser 340 | Ala | Ile | Glu | Lys | Asp 345 | Lys | Glu | Gly | Ile | Gln 350 | Asn | Ala |
| Lys | Glu | Ile 355 | Leu | Thr | Arg | Leu | Gly 360 | Val | Glu | Pro | Ser | Asp 365 | Val | Asp | Cys |
| Val | Ser 370 | Val | Gln | His | Ile | Cys 375 | Thr | Ile | Val | Ser | Phe 380 | Arg | Ser | Ala | Asn |
| Leu 385 | Val | Ala | Ala | Thr | Leu 390 | Gly | Ala | Ile | Leu | Asn 395 | Arg | Leu | Arg | Asp | Asn 400 |
| Lys | Gly | Thr | Pro | Ser 405 | Leu | Arg | Thr | Thr | Val 410 | Gly | Val | Asp | Gly | Ser 415 | Leu |
| Tyr | Lys | Met | His 420 | Pro | Gln | Tyr | Ser | Arg 425 | Arg | Phe | His | Lys | Thr 430 | Leu | Arg |
| Arg | Val | Val 435 | Pro | Asp | Ser | Asp | Val 440 | Arg | Phe | Leu | Leu | Ser 445 | Glu | Ser | Gly |
| Thr | Gly 450 | Lys | Gly | Ala | Ala | Met 455 | Val | Thr | Ala | Val | Ala 460 | Tyr | Arg | Leu | Ala |
| Glu 465 | Gln | His | Arg | Gln | Ile 470 | Glu | Glu | Thr | Leu | Ala 475 | His | Phe | Arg | Leu | Ser 480 |
| Lys | Gln | Thr | Leu | Met 485 | Glu | Val | Lys | Lys | Arg 490 | Leu | Arg | Thr | Glu | Met 495 | Glu |
| Met | Gly | Leu | Arg 500 | Lys | Glu | Thr | Asn | Ser 505 | Lys | Ala | Thr | Val | Lys 510 | Met | Leu |
| Pro | Ser | Phe 515 | Val | Arg | Ser | Ile | Pro 520 | Asp | Gly | Thr | Glu | His 525 | Gly | Asp | Phe |
| Leu | Ala 530 | Leu | Asp | Leu | Gly | Gly 535 | Thr | Asn | Phe | Arg | Val 540 | Leu | Leu | Val | Lys |
| Ile | Arg | Ser 545 | Gly | Lys | Lys | Arg | Thr 550 | Val | Glu | Met | His | Asn 555 | Lys | Ile | Tyr 560 |
| Ser | Ile | Pro | Leu | Glu 565 | Ile | Met | Gln | Gly | Thr 570 | Gly | Asp | Glu | Leu | Phe 575 | Asp |
| His | Ile | Val | Ser 580 | Cys | Ile | Ser | Asp | Phe 585 | Leu | Asp | Tyr | Met | Gly 590 | Ile | Lys |
| Gly | Pro | Arg 595 | Met | Pro | Leu | Gly | Phe 600 | Thr | Phe | Ser | Phe | Pro 605 | Cys | His | Gln |
| Thr | Asn | Leu | Asp | Cys | Gly | Ile | Leu | Ile | Ser | Trp | Thr | Lys | Gly | Phe | Lys |

|   | 610 |   |   |   |   | 615 |   |   |   |   | 620 |   |   |   |
|---|---|---|---|---|---|---|---|---|---|---|---|---|---|---|
| Ala 625 | Thr | Asp | Cys | Glu | Gly 630 | His | Asp | Val | Ala | Ser 635 | Leu | Leu | Arg | Asp | Ala 640 |

Val Lys Arg Arg Glu Glu Phe Asp Leu Asp Val Val Ala Val Asn
                    645              650                    655

Asp Thr Val Gly Thr Met Met Thr Cys Ala Tyr Glu Glu Pro Thr Cys
                660              665                 670

Glu Ile Gly Leu Ile Val Gly Thr Gly Thr Asn Ala Cys Tyr Met Glu
            675              680                685

Glu Met Lys Asn Val Glu Met Val Glu Gly Asn Gln Gly Gln Met Cys
        690                  695              700

Ile Asn Met Glu Trp Gly Ala Phe Gly Asp Asn Gly Cys Leu Asp Asp
705                 710                 715                    720

Ile Arg Thr Asp Phe Asp Lys Val Val Asp Glu Tyr Ser Leu Asn Ser
                725              730                    735

Gly Lys Gln Arg Phe Glu Lys Met Ile Ser Gly Met Tyr Leu Gly Glu
            740                 745              750

Ile Val Arg Asn Ile Leu Ile Asp Phe Thr Lys Lys Gly Phe Leu Phe
        755                 760                 765

Arg Gly Gln Ile Ser Glu Pro Leu Lys Thr Arg Gly Ile Phe Glu Thr
770                 775                 780

Lys Phe Leu Ser Gln Ile Glu Ser Asp Arg Leu Ala Leu Leu Gln Val
785             790                 795                    800

Arg Ala Ile Leu Gln Gln Leu Gly Leu Asn Ser Thr Cys Asp Asp Ser
                805                 810                 815

Ile Leu Val Lys Thr Val Cys Gly Val Val Ser Lys Arg Ala Ala Gln
            820                 825                 830

Leu Cys Gly Ala Gly Met Ala Ala Val Val Glu Lys Ile Arg Glu Asn
        835                 840                 845

Arg Gly Leu Asp His Leu Asn Val Thr Val Gly Val Asp Gly Thr Leu
    850                 855                 860

Tyr Lys Leu His Pro His Phe Ser Arg Ile Met His Gln Thr Val Lys
865             870                 875                    880

Glu Leu Ser Pro Lys Cys Thr Val Ser Phe Leu Leu Ser Glu Asp Gly
                885                 890                 895

Ser Gly Lys Gly Ala Ala Leu Ile Thr Ala Val Gly Val Arg Leu Arg
            900                 905                 910

Gly Asp Pro Ser Ile Ala
            915

( 2 ) INFORMATION FOR SEQ ID NO:15:

( i ) SEQUENCE CHARACTERISTICS:
        ( A ) LENGTH: 3635 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
CGGAAAACCT  GTTTCTGGAA  ACGCGAGGCC  CTCAGCTGGT  GAGCCATCGT  GGTTAAGCTT      60

CTTTGTGTGG  CTCCTGGAGT  CTCCGATCCC  AGCCGGACAC  CCGGGCCTGG  TTTCAAAGCG     120

GTCGAACTGC  TCTGCCCGCT  CCACCGGTAG  CGCTCGAGCC  TCGGTTTCTC  TACTCGACCC     180

CGACTCGCCG  CAGCAGGATG  ATCGCCTCGC  ATATGATCGC  CTGCTTATTC  ACGGAGCTCA     240

ACCAAAACCA  AGTGCAGAAG  GTTGACCAAT  TTCTCTACCA  CATGCGTCTC  TCAGATGAGA     300
```

-continued

| | | | | | | |
|---|---|---|---|---|---|---|
| CCCTTCTGGA | GATTTCTAGG | CGGTTCCGGA | AGGAGATGGA | GAAAGGGCTA | GGAGCTACCA | 360 |
| CGCACCCTAC | AGCAGCTGTG | AAAATGTTGC | CTACCTTTGT | GAGGTCAACT | CCGGATGGGA | 420 |
| CAGAACATGG | GGAGTTCCTG | GCTCTGGATC | TTGGAGGAAC | CAACTTCCGT | GTGCTCCGAG | 480 |
| TAAGGGTGAC | GGACAATGGC | CTCCAGAGAG | TGGAGATGGA | GAACCAGATC | TACGCCATCC | 540 |
| CTGAGGACAT | CATGCGGGGC | AGTGGAACCC | AGCTGTTTGA | CCACATCGCC | GAATGCCTGG | 600 |
| CCAACTTCAT | GGACAAGCTA | CAAATCAAAG | AGAAGAAGCT | CCCTCTGGGT | TTCACCTTCT | 660 |
| CGTTCCCCTG | CCACCAGACA | AAACTGGATG | AGAGTTTTTT | GGTCTCGTGG | ACTAAGGGGT | 720 |
| TCAAGTCCAG | TGGCGTGGAA | GGCAGAGATG | TGGTGGACCT | GATCCGGAAG | GCTATCCAGC | 780 |
| GCAGAGGGGA | CTTTGACATT | GACATTGTGG | CCGTGGTGAA | TGACACAGTT | GGGACCATGA | 840 |
| TGACTTGTGG | CTATGATGAT | CAGAACTGCG | AGATTGGTCT | CATTGTGGGC | ACTGGCAGCA | 900 |
| ACGCCTGCTA | CATGGAGGAA | ATGCGTCATA | TTGACATGGT | GGAGGGAGAT | GAGGGGCGCA | 960 |
| TGTGCATCAA | CATGGAGTGG | GGAGCCTTTG | GGACGACGG | TACACTCAAT | GACATCCGAA | 1020 |
| CCGAGTTTGA | CCGAGAGATC | GACATGGGCT | CGCTGAACCC | TGGGAAGCAG | CTGTTTGAGA | 1080 |
| AGATGATTAG | CGGGATGTAC | ATGGGGGAGC | TGGTCAGGCT | CATCCTGGTG | AAGATGGCCA | 1140 |
| AGGCAGAGCT | GTTGTTCCAA | GGGAAACTCA | GCCCAGAACT | CCTTACCACT | GGCTCCTTCG | 1200 |
| AGACCAAAGA | TGTCTCGGAT | ATTGAAGAGG | ATAAGGATGG | AATCGAGAAG | GCCTACCAAA | 1260 |
| TCCTGATGCG | CCTGGGTCTG | AATCCATTGC | AGGAGGATTG | TGTGGCCACG | CACCGAATCT | 1320 |
| GCCAGATTGT | GTCCACGCGC | TCGGCCAGTC | TGTGCGCAGC | CACCCTGGCC | GCGGTGCTGT | 1380 |
| GGCGAATCAA | AGAGAACAAG | GGCGAGGAGC | GACTTCGCTC | CACCATCGGT | GTCGATGGCT | 1440 |
| CCGTCTACAA | GAAACATCCC | CATTTGCCA | AGCGTCTCCA | TAAGGCAGTG | AGGAGGCTGG | 1500 |
| TGCCCGACTG | TGATGTCCGC | TTCCTCCGCT | CTGAGGATGG | CAGCGGCAAG | GGGGCTGCTA | 1560 |
| TGGTGACGGC | GGTGGCTTAC | CGTCTGGCTG | ACCAACACCG | GGCCCGCCAG | AAGACCCTGG | 1620 |
| AGTCTCTGAA | GCTGAGCCAC | GAGCAGCTTC | TGGAGGTTAA | GAGAAGAATG | AAGGTGGAAA | 1680 |
| TGGAGCAGGG | TCTGAGCAAG | GAGACGCATG | CGGTCGCCCC | TGTGAAGATG | CTGCCCACTT | 1740 |
| ACGTGTGTGC | CACTCCAGAT | GGCACAGAGA | AAGGAGACTT | CTTGGCCTTG | GATCTTGGAG | 1800 |
| GAACAAACTT | CCGGGTCCTG | CTGGTGCGTG | TGCGTAATGG | CAAGCGGAGG | GGCGTGGAGA | 1860 |
| TGCATAACAA | GATCTACTCC | ATCCCACAGG | AGGTTATGCA | TGGCACTGGG | GAAGAGCTCT | 1920 |
| TCGACCACAT | TGTCCAGTGC | ATTGCGGACT | TCCTGGAGTA | CATGGGCATG | AAGGGCGTGT | 1980 |
| CCCTGCCTTT | GGGTTTCACA | TTCTCCTTCC | CTTGCCAGCA | GAACAGCCTA | GACCAGAGCA | 2040 |
| TCCTCCTCAA | GTGGACAAAG | GGATTCAAGG | CATCTGGCTG | CGAGGGTGAG | GATGTGGTCA | 2100 |
| CCTTGCTGAA | GGAAGCGATT | CACCGGCGAG | AGGAGTTTGA | CCTGGATGTG | GTTGCCGTGG | 2160 |
| TGAATGACAC | AGTTGGGACT | ATGATGACTT | GTGGCTACGA | AGACCCTCAC | TGTGAAGTTG | 2220 |
| GCCTCATTGT | TGGCACCGGA | AGCAACGCCT | GCTACATGGA | AGAGATGCGT | AATGTGGAGC | 2280 |
| TGGTGGACGG | AGAGGAGGGA | CGGATGTGTG | TCAACATGGA | GTGGGGAGCA | TTTGGGGACA | 2340 |
| ATGGCTGCCT | GGATGACTTG | CGGACCGTGT | TTGATGTTGC | TGTGGATGAG | CTTTCTCTCA | 2400 |
| ACCCTGGCAA | ACAGAGGTTC | GAGAAGATGA | TCAGCGGCAT | GTACTTGGGA | GAGATTGTGC | 2460 |
| GCAACATTCT | CATCGATTTC | ACGAAGCGGG | GGCTGCTCTT | CCGAGGCCGC | ATCTCAGAGC | 2520 |
| GCCTCAAGAC | AAGGGGAATC | TTTGAAACTA | AGTTCCTGTC | TCAGATAGAG | AGCGACTGCC | 2580 |
| TAGCCCTGCT | ACAGGTTCGT | GCCATCCTGC | GCCACCTAGG | GCTGGAGAGC | ACGTGCGATG | 2640 |
| ACAGCATCAT | CGTGAAGGAG | GTGTGCACTG | TGGTTGCCCG | GCGCGCTGCA | CAGCTCTGTG | 2700 |

|      |      |      |      |      |      |
|------|------|------|------|------|------|
| GCGCAGGCAT | GGCCGCCGTA | GTGGACAAGA | TAAGAGAGAA | CCGTGGGCTG | GACAACCTCA | 2760 |
| AAGTGACAGT | GGGCGTGGAC | GGGACTCTGT | ATAAGCTTCA | TCCTCACTTT | GCCAAGGTCA | 2820 |
| TGCATGAGAC | GGTGAGAGAT | CTGGCTCCGA | AATGTGACGT | GTCCTTCCTG | GAATCCGAGG | 2880 |
| ACGGCAGTGG | GAAGGGAGCA | GCTCTCATCA | CTGCCGTGGC | CTGCCGCATC | CGGGAGGCTG | 2940 |
| GGCAGAGATA | GAAGCTTGGG | GACCAGACGG | GGCTTCTCTG | CTTCCTCACT | TCCCCGTTTT | 3000 |
| AAATTATGAG | AAGATGGACC | CCTTGGCAGA | GAGGACCCTG | TGAGACTGGG | ACTTTTGTCT | 3060 |
| CTGTATATTC | ACTGTAGAGT | TTGGTACCCA | ATCCTTGGCC | TTCCTGAGAA | TCTGAAGTAA | 3120 |
| GGAGTTGTTC | GCAGTTCCTG | CTGGTCACCT | CCTGGGATGG | TCCTCCCCCA | CTCTACTTCC | 3180 |
| TGTACAATCC | TATGGGATGG | GGACAGTCTT | GAGAAAATGG | TTGCCTCAGC | TTGGAGCTGA | 3240 |
| ACCTGACATT | TGTAGGTGGA | GAACATCTTG | AAATGTCGAT | GCTTCTCTCA | TCAGAGGTAG | 3300 |
| ATGTTGGGTG | GGAGGGAGGA | GGAGAGATAG | GACGTCCCCT | GCCCTACGTG | GCTGTCCCTC | 3360 |
| TTCAACTCAA | CCCATAAGCA | TCACCCTGCC | GGTTCTAAAA | CATTTGCTGT | CCTGGGATAG | 3420 |
| AGGAATCTGA | ACCAAAGCTA | GAGTGGACGT | CTTCTTCAAG | TGTTTGTGGC | TTTACCTCAC | 3480 |
| ATGGCTGAAT | GTGTCATCCA | CGAGCTACAG | ACCTTGGGGA | CAGGAGTGGC | TTTGGTCGCT | 3540 |
| TTTTAGTTTT | TTGTTTTGTT | TTGTTTTTTT | CTTTTTTAAT | TTATGTTTGA | AATTTACTTA | 3600 |
| GTTTAAAGCA | GGTCCTCTCC | ATTGTGTAAT | GGTTG | | | 3635 |

(2) INFORMATION FOR SEQ ID NO:16:

(i) SEQUENCE CHARACTERISTICS:
        (A) LENGTH: 917 amino acids
        (B) TYPE: amino acid
        (C) STRANDEDNESS: single
        (D) TOPOLOGY: linear (xi) SEQUENCE DESCRIPTION: SEQ ID NO:16:

```
Met Ile Ala Ser His Met Ile Ala Cys Leu Phe Thr Glu Leu Asn Gln
  1               5                  10                  15

Asn Gln Val Gln Lys Val Asp Gln Phe Leu Tyr His Met Arg Leu Ser
             20                  25                  30

Asp Glu Thr Leu Leu Glu Ile Ser Arg Arg Phe Arg Lys Glu Met Glu
         35                  40                  45

Lys Gly Leu Gly Ala Thr Thr His Pro Thr Ala Ala Val Lys Met Leu
 50                  55                  60

Pro Thr Phe Val Arg Ser Thr Pro Asp Gly Thr Glu His Gly Glu Phe
 65                  70                  75                  80

Leu Ala Leu Asp Leu Gly Gly Thr Asn Phe Arg Val Leu Arg Val Arg
                 85                  90                  95

Val Thr Asp Asn Gly Leu Gln Arg Val Glu Met Glu Asn Gln Ile Tyr
             100                 105                 110

Ala Ile Pro Glu Asp Ile Met Arg Gly Ser Gly Thr Gln Leu Phe Asp
         115                 120                 125

His Ile Ala Glu Cys Leu Ala Asn Phe Met Asp Lys Leu Gln Ile Lys
 130                 135                 140

Glu Lys Lys Leu Pro Leu Gly Phe Thr Phe Ser Phe Pro Cys His Gln
145                 150                 155                 160

Thr Lys Leu Asp Glu Ser Phe Leu Val Ser Trp Thr Lys Gly Phe Lys
                 165                 170                 175

Ser Ser Gly Val Glu Gly Arg Asp Val Val Asp Leu Ile Arg Lys Ala
             180                 185                 190

Ile Gln Arg Arg Gly Asp Phe Asp Ile Asp Ile Val Ala Val Val Asn
```

-continued

|     |     |     | 195 |     |     |     | 200 |     |     |     | 205 |     |     |
|-----|-----|-----|-----|-----|-----|-----|-----|-----|-----|-----|-----|-----|-----|

Asp Thr Val Gly Thr Met Met Thr Cys Gly Tyr Asp Gln Asn Cys
        210                 215                 220

Glu Ile Gly Leu Ile Val Gly Thr Gly Ser Asn Ala Cys Tyr Met Glu
225                 230                 235                     240

Glu Met Arg His Ile Asp Met Val Glu Gly Asp Glu Gly Arg Met Cys
                245                 250                     255

Ile Asn Met Glu Trp Gly Ala Phe Gly Asp Asp Gly Thr Leu Asn Asp
            260                 265                 270

Ile Arg Thr Glu Phe Asp Arg Glu Ile Asp Met Gly Ser Leu Asn Pro
        275                 280                 285

Gly Lys Gln Leu Phe Glu Lys Met Ile Ser Gly Met Tyr Met Gly Glu
        290                 295                 300

Leu Val Arg Leu Ile Leu Val Lys Met Ala Lys Ala Glu Leu Leu Phe
305                 310                 315                     320

Gln Gly Lys Leu Ser Pro Glu Leu Leu Thr Thr Gly Ser Phe Glu Thr
                325                 330                 335

Lys Asp Val Ser Asp Ile Glu Glu Asp Lys Asp Gly Ile Glu Lys Ala
            340                 345                 350

Tyr Gln Ile Leu Met Arg Leu Gly Leu Asn Pro Leu Gln Glu Asp Cys
        355                 360                 365

Val Ala Thr His Arg Ile Cys Gln Ile Val Ser Thr Arg Ser Ala Ser
    370                 375                 380

Leu Cys Ala Ala Thr Leu Ala Ala Val Leu Trp Arg Ile Lys Glu Asn
385                 390                 395                     400

Lys Gly Glu Glu Arg Leu Arg Ser Thr Ile Gly Val Asp Gly Ser Val
                405                 410                 415

Tyr Lys Lys His Pro His Phe Ala Lys Arg Leu His Lys Ala Val Arg
            420                 425                 430

Arg Leu Val Pro Asp Cys Asp Val Arg Phe Leu Arg Ser Glu Asp Gly
        435                 440                 445

Ser Gly Lys Gly Ala Ala Met Val Thr Ala Val Ala Tyr Arg Leu Ala
        450                 455                 460

Asp Gln His Arg Ala Arg Gln Lys Thr Leu Glu Ser Leu Lys Leu Ser
465                 470                 475                     480

His Glu Gln Leu Leu Glu Val Lys Arg Arg Met Lys Val Glu Met Glu
                485                 490                 495

Gln Gly Leu Ser Lys Glu Thr His Ala Val Ala Pro Val Lys Met Leu
            500                 505                 510

Pro Thr Tyr Val Cys Ala Thr Pro Asp Gly Thr Glu Lys Gly Asp Phe
        515                 520                 525

Leu Ala Leu Asp Leu Gly Gly Thr Asn Phe Arg Val Leu Leu Val Arg
    530                 535                 540

Val Arg Asn Gly Lys Arg Arg Gly Val Glu Met His Asn Lys Ile Tyr
545                 550                 555                     560

Ser Ile Pro Gln Glu Val Met His Gly Thr Gly Glu Glu Leu Phe Asp
                565                 570                 575

His Ile Val Gln Cys Ile Ala Asp Phe Leu Glu Tyr Met Gly Met Lys
            580                 585                 590

Gly Val Ser Leu Pro Leu Gly Phe Thr Phe Ser Phe Pro Cys Gln Gln
        595                 600                 605

Asn Ser Leu Asp Gln Ser Ile Leu Leu Lys Trp Thr Lys Gly Phe Lys
610                 615                 620

| | | | | | | | | | | | | | | |
|---|---|---|---|---|---|---|---|---|---|---|---|---|---|---|
| Ala | Ser | Gly | Cys | Glu | Gly | Glu | Asp | Val | Val | Thr | Leu | Leu | Lys | Glu | Ala |
| 625 | | | | 630 | | | | | 635 | | | | | 640 |
| Ile | His | Arg | Arg | Glu | Glu | Phe | Asp | Leu | Asp | Val | Val | Ala | Val | Val | Asn |
| | | | | 645 | | | | | 650 | | | | | 655 | |
| Asp | Thr | Val | Gly | Thr | Met | Met | Thr | Cys | Gly | Tyr | Glu | Asp | Pro | His | Cys |
| | | | 660 | | | | | 665 | | | | | 670 | | |
| Glu | Val | Gly | Leu | Ile | Val | Gly | Thr | Gly | Ser | Asn | Ala | Cys | Tyr | Met | Glu |
| | | 675 | | | | | 680 | | | | | 685 | | | |
| Glu | Met | Arg | Asn | Val | Glu | Leu | Val | Asp | Gly | Glu | Gly | Arg | Met | Cys |
| | 690 | | | | | 695 | | | | | 700 | | | | |
| Val | Asn | Met | Glu | Trp | Gly | Ala | Phe | Gly | Asp | Asn | Gly | Cys | Leu | Asp | Asp |
| 705 | | | | | 710 | | | | | 715 | | | | | 720 |
| Leu | Arg | Thr | Val | Phe | Asp | Val | Ala | Val | Asp | Glu | Leu | Ser | Leu | Asn | Pro |
| | | | | 725 | | | | | 730 | | | | | 735 | |
| Gly | Lys | Gln | Arg | Phe | Glu | Lys | Met | Ile | Ser | Gly | Met | Tyr | Leu | Gly | Glu |
| | | | 740 | | | | | 745 | | | | | 750 | | |
| Ile | Val | Arg | Asn | Ile | Leu | Ile | Asp | Phe | Thr | Lys | Arg | Gly | Leu | Leu | Phe |
| | | 755 | | | | | 760 | | | | | 765 | | | |
| Arg | Gly | Arg | Ile | Ser | Glu | Arg | Leu | Lys | Thr | Arg | Gly | Ile | Phe | Glu | Thr |
| | 770 | | | | | 775 | | | | | 780 | | | | |
| Lys | Phe | Leu | Ser | Gln | Ile | Glu | Ser | Asp | Cys | Leu | Ala | Leu | Leu | Gln | Val |
| 785 | | | | | 790 | | | | | 795 | | | | | 800 |
| Arg | Ala | Ile | Leu | Arg | His | Leu | Gly | Leu | Glu | Ser | Thr | Cys | Asp | Asp | Ser |
| | | | | 805 | | | | | 810 | | | | | 815 | |
| Ile | Ile | Val | Lys | Glu | Val | Cys | Thr | Val | Val | Ala | Arg | Arg | Ala | Ala | Gln |
| | | | 820 | | | | | 825 | | | | | 830 | | |
| Leu | Cys | Gly | Ala | Gly | Met | Ala | Ala | Val | Val | Asp | Lys | Ile | Arg | Glu | Asn |
| | | 835 | | | | | 840 | | | | | 845 | | | |
| Arg | Gly | Leu | Asp | Asn | Leu | Lys | Val | Thr | Val | Gly | Val | Asp | Gly | Thr | Leu |
| | 850 | | | | | 855 | | | | | 860 | | | | |
| Tyr | Lys | Leu | His | Pro | His | Phe | Ala | Lys | Val | Met | His | Glu | Thr | Val | Arg |
| 865 | | | | | 870 | | | | | 875 | | | | | 880 |
| Asp | Leu | Ala | Pro | Lys | Cys | Asp | Val | Ser | Phe | Leu | Glu | Ser | Glu | Asp | Gly |
| | | | | 885 | | | | | 890 | | | | | 895 | |
| Ser | Gly | Lys | Gly | Ala | Ala | Leu | Ile | Thr | Ala | Val | Ala | Cys | Arg | Ile | Arg |
| | | | 900 | | | | | 905 | | | | | 910 | | |
| Glu | Ala | Gly | Gln | Arg |
| | | | 915 | |

(2) INFORMATION FOR SEQ ID NO:17:

(i) SEQUENCE CHARACTERISTICS:
        (A) LENGTH: 3692 base pairs
        (B) TYPE: nucleic acid
        (C) STRANDEDNESS: single
        (D) TOPOLOGY: linear (xi) SEQUENCE DESCRIPTION: SEQ ID NO:17:

```
GTCGTCTTAT TTGGGAGCTG AGACTTGAGG AAGGTGATAA CTTCTGAATC CCCCCAGGTA      60
GTCAATACCA TTGTGGAAAC ATGGCCGCCA TTGAGCCTTC TGGTCTGCAC CCGGGAGAAA     120
GAGACTCAAG CTGCCCCCAG GAGGGCATTC CAAGGCCCTC AGGTAGCTTA GAACTGGCAC     180
AGGAATACTT GCAACAATTC AAGGTGACCA TGACACAGCT GCAGCAGATC CAAGCCAGTC     240
TTCTGTGTTC CATGGAGCAG GCGCTGAAGG GACAGGACAG TCCCGCTCCT TCTGTCCGGA     300
TGTTGCCCAC ATACGTGAGG TCCACACCAC ATGGCACCGA GCAAGGAGAC TTCCTGGTGC     360
```

-continued

| | | | | | | |
|---|---|---|---|---|---|---|
| TGGAGCTGGG | GGCCACAGGA | GCCTCACTAC | GTGTGTTGTG | GGTAACACTG | ACGGGCACCA | 420 |
| AGGAACACAG | CGTGGAGACC | AGGAGCCAGG | AGTTTGTGAT | CCCTCAAGAG | GTGATCCTAG | 480 |
| GTGCTGGCCA | GCAGCTCTTT | GACTTTGCTG | CCCGCTGCCT | CTCTGAATTC | CTGGATGCAT | 540 |
| ACCCCGTGGA | GAATCAGGGT | CTGAAGCTTG | GGTTTAATTT | CTCTTTTCCT | TGTCACCAGA | 600 |
| CAGGCTTGGA | CAAGAGCACC | CTCATTTCCT | GGACAAAAGG | TTTTAGGTGC | AGTGGTGTGG | 660 |
| AAGGCCAGGA | TGTGGTCCAG | TTGCTAAGGG | ATGCCATTCA | GAGGCAGGGG | ACCTACAATA | 720 |
| TTGATGTGGT | AGCCATGGTG | AATGACACAG | TGGGTACCAT | GATGGGCTGT | GAGCTGGGCA | 780 |
| CCAGGCCATG | TGAAGTCGGG | CTTATTGTAG | ACACTGGTAC | CAATGCCTGT | TATATGGAGG | 840 |
| AAGCGAGGCA | CGTGGCAGCT | CTGGATGAGG | ACCGCGGCCG | TACCTGTGTC | AGCATCGAGT | 900 |
| GGGGCTCCTT | CTATGACGAA | GAGGCCCTAG | GGCCAGTACT | GACCACCTTC | GACGATGCCC | 960 |
| TGGACCACGA | GTCCCTGGTT | CCTGGTGCTC | AGAGGTTTGA | GAAGATGATT | GGTGGCCTTT | 1020 |
| ACTTGGGTGA | GCTGGTAAGG | CTGGTGCTGG | TCCACTTGTC | CCAGCATGGG | GTCCTCTTTG | 1080 |
| GTGGCTGCGC | CTCTCCTGCG | TTGCTGAGTC | AAAACAGCAT | CCTCCTGGAA | CATGTGGCCA | 1140 |
| AAATGGAGGA | CCCTGCCACT | GGGATAGCCC | ACGTCCACAC | AGTCCTGCAG | GCTTGGGTC | 1200 |
| TGAGCCCTCA | GGCCTCAGAT | GCTGAGCTCG | TGCAGCGCGT | GTGCATGGCT | GTGTGCACGC | 1260 |
| GAGCTGCCCA | GCTCTGTGCC | TCTGCCCTGG | CTGCAGTCCT | ATCCCGCCTC | CAGCACAGCA | 1320 |
| GGGAGCAGCA | GACACTGCAC | GTGGCCGTGG | CCACTGGAGG | GCGAGTGTTC | GAATGGCACC | 1380 |
| CCAGGTTCCT | CTGCATCCTA | AAGGAGACGG | TAATGCTCTT | GGCCCCAGAG | TGTGATGTCT | 1440 |
| CCTTCATCCC | CTCTGTGGAT | GGTGGTGGCC | GGGGTGTGGC | AATGGTGACT | GCTGTGGCAG | 1500 |
| CCCGCCTGGC | TACCCACAGG | CGCATCCTGG | AAGAGACCCT | GGCACCATTT | CAGCTGAGCT | 1560 |
| TGGAGCAGCT | GACAGCGGTG | CAGGCACAAA | TGCGGGAAGC | CATGATCAGG | GGGCTTCAAG | 1620 |
| GAGAGAGCTC | CTCCCTCCGC | ATGCTGCCCA | CTTACGTCCG | AGCAACGCCC | GATGGCAGCG | 1680 |
| AACGAGGTGA | CTTCCTGGCT | TTGGACCTAG | GGGGCACCAA | CTTCCGTGTC | CTGTTGGTAC | 1740 |
| GCGTGGCCGA | GGGCAGTGTT | CAGATCACCA | ACCAGGTCTA | CTCTATTCCT | GAGTATGTAG | 1800 |
| CCCAGGGCTC | TGGACAGAAG | CTCTTTGATC | ATATTGTGGA | CTGCATCGTG | GACTTCCAGA | 1860 |
| AGAGGCAAGG | CCTTAGCGGA | CAGAGCCTAC | CCCTGGGTTT | CACCTTCTCT | TTTCCTTGCA | 1920 |
| AGCAGCTTGG | CCTGGACCAG | GGCATCCTCC | TCAACTGGAC | TAAGGGGTTC | AATGCATCAG | 1980 |
| GCTGCGAGGG | CCAAGATGTT | GTGTATTTAT | TACGGGAAGC | CATTAGGCGC | AGACAGGCAG | 2040 |
| TGGAGCTGAA | TGTGGTTGCC | ATTGTCAATG | ACACGGTGGG | GACCATGATG | TCCTGTGGCT | 2100 |
| ATGATGATCC | CTGTTGTGAG | ATGGGCCTCA | TTGTCGGAAC | CGGTACCAAC | GCCTGCTATA | 2160 |
| TGGAAGAACT | CCGGAATGTG | GCGAGTGTGC | CCGGGGACTC | AGGCCACATG | TGTATCAACA | 2220 |
| TGGAGTGGGG | TGCCTTTGGG | GATGACGGCT | CACTGAGCAT | GCTCGGCACC | TGCTTTGATG | 2280 |
| CTAGCGTGGA | CCAGGCATCC | ATCAACCCAG | GCAAACAGAG | GTTTGAGAAA | ATGATCAGCG | 2340 |
| GAATGTACCT | GGGGGAGATC | GTCCGCCATA | TCCTCCTGCA | CTTAACCAGT | CTTGGAGTTC | 2400 |
| TCTTCCGGGG | CCAGAAGACG | CAATGCCTTC | AGACCAGGGA | CATCTTTAAG | ACCAAGTTTC | 2460 |
| TCTCCGAGAT | TGAGAGCGAC | AGCCTGGCCC | TGCGTCAGGT | CCGAGCCATC | CTGGAGGACC | 2520 |
| TGGGGCTGAC | TCTGACGTCT | GATGATGCCT | TGATGGTCCT | AGAGGTGTGC | CAGGCTGTGT | 2580 |
| CCCGCAGGGC | CGCCCAACTC | TGCGGGGCAG | GTGTGGCTGC | AGTGGTGGAA | AAGATACGGG | 2640 |
| AGAACCGGGG | CCTGCAGGAG | CTGACAGTGT | CTGTGGGAGT | GGATGGGACG | CTCTACAAGC | 2700 |
| TACATCCCCA | CTTCTCCAGG | CTGGTGTCAG | TGACAGTTCG | GAAGCTAGCC | CCTCAGTGCA | 2760 |

-continued

```
CAGTCACCTT TTTGCAATCG GAGGATGGGT CTGGGAAAGG GGCAGCGTTG GTCACTCGTG      2820
TCGCTTGCCG CCTGACCCAG ATGGCCTGCG TTTGAGGAAA ATCTCCAAAG AGCAATTGGG      2880
ATCTCCCTGG ACTAAGGATT CAGCCCACAC GGACCCTCTG GCGGGCCCAG CCACCCACAA      2940
CTCCCAAAGA AACCCACGGG TGGTGCCCTC ATAACTGTCC GCCCACACCC AATGGCTTTC      3000
TGAGAGAAGC ACCACTCTGG TTAGCAAGGA ATTCCCCGAA GATGGCGGAG GGGCAGGTTC      3060
TAGTATTGGA TGGCCGGGGC CATCTTCTGG GCCGCCTGGC CGATTGTGGC CAACTGCTGG      3120
GCAGGTAGCC GAAAGGTGGT GGTTGTACGC TGTGAGGGCA TCAACATTTC TGGAAATTTC      3180
TACAGAAACA AGTTAAAGTA TCTGGCCTTC TCCGAAAGCG GATGAACACC AACCCGTCTC      3240
GAGGCCCCTA CCACTTCCGA GCCCCAAGCC GCATTTTTTG GCGCACTGTG CGAGGCATGC      3300
TGCCGCACAA GACCAAAAGA GGCCAGGCTG CCCTGGAACG CCTCAAGGTG TTGGATGGGA      3360
TCCCTCCACC CTATGACAAG AAAAAGCGGA TGGTGGTCCC TGCTGCCCTC AAGGTTGTGC      3420
GGCTGAAGCT ACCAGAAAGT TTGCTTACCT GGGGCGTCTG GCTCATGAGG TCGGGTGGAA      3480
GTACCAGGCA GTGACAGCTA CTCTGGAGGA GAAACGGAAG GAAAAGGCAA AGATCCATTA      3540
CCGGAAGAAG AAGCAGCTCT TGAGGCTAAG GAAACAGGCA GAAAGAATG TGGAGAAGAA      3600
AATCTGCAAG TTCACAGAGG TCCTCAAGAC CAATGGACTC TTGGTGTGAA CCAATAAAGA      3660
CTGTTTGTGC CTCAAAAAAA AAAAAAAAAA AA                                   3692
```

( 2 ) INFORMATION FOR SEQ ID NO:18:

( i ) SEQUENCE CHARACTERISTICS:
  ( A ) LENGTH: 924 amino acids
  ( B ) TYPE: amino acid
  ( C ) STRANDEDNESS: single
  ( D ) TOPOLOGY: linear ( x i ) SEQUENCE DESCRIPTION: SEQ ID NO:18:

```
Met Ala Ala Ile Glu Pro Ser Gly Leu His Pro Gly Glu Arg Asp Ser
1               5                   10                  15

Ser Cys Pro Gln Glu Gly Ile Pro Arg Pro Ser Gly Ser Leu Glu Leu
            20                  25                  30

Ala Gln Glu Tyr Leu Gln Gln Phe Lys Val Thr Met Thr Gln Leu Gln
        35                  40                  45

Gln Ile Gln Ala Ser Leu Leu Cys Ser Met Glu Gln Ala Leu Lys Gly
    50                  55                  60

Gln Asp Ser Pro Ala Pro Ser Val Arg Met Leu Pro Thr Tyr Val Arg
65                  70                  75                  80

Ser Thr Pro His Gly Thr Glu Gln Gly Asp Phe Leu Val Leu Glu Leu
                85                  90                  95

Gly Ala Thr Gly Ala Ser Leu Arg Val Leu Trp Val Thr Leu Thr Gly
            100                 105                 110

Thr Lys Glu His Ser Val Glu Thr Arg Ser Gln Glu Phe Val Ile Pro
        115                 120                 125

Gln Glu Val Ile Leu Gly Ala Gly Gln Gln Leu Phe Asp Phe Ala Ala
    130                 135                 140

Arg Cys Leu Ser Glu Phe Leu Asp Ala Tyr Pro Val Glu Asn Gln Gly
145                 150                 155                 160

Leu Lys Leu Gly Phe Asn Phe Ser Phe Pro Cys His Gln Thr Gly Leu
                165                 170                 175

Asp Lys Ser Thr Leu Ile Ser Trp Thr Lys Gly Phe Arg Cys Ser Gly
            180                 185                 190

Val Glu Gly Gln Asp Val Val Gln Leu Leu Arg Asp Ala Ile Gln Arg
```

|     |     |     | 195 |     |     |     | 200 |     |     |     | 205 |     |     |
| --- | --- | --- | --- | --- | --- | --- | --- | --- | --- | --- | --- | --- | --- |
| Gln | Gly 210 | Thr | Tyr | Asn | Ile | Asp 215 | Val | Val | Ala | Met | Val 220 | Asn | Asp | Thr | Val |
| Gly 225 | Thr | Met | Met | Gly | Cys 230 | Glu | Leu | Gly | Thr | Arg 235 | Pro | Cys | Glu | Val | Gly 240 |
| Leu | Ile | Val | Asp | Thr 245 | Gly | Thr | Asn | Ala | Cys 250 | Tyr | Met | Glu | Glu | Ala 255 | Arg |
| His | Val | Ala | Ala 260 | Leu | Asp | Glu | Asp | Arg 265 | Gly | Arg | Thr | Cys | Val 270 | Ser | Ile |
| Glu | Trp | Gly 275 | Ser | Phe | Tyr | Asp | Glu 280 | Glu | Ala | Leu | Gly | Pro 285 | Val | Leu | Thr |
| Thr | Phe 290 | Asp | Asp | Ala | Leu | Asp 295 | His | Glu | Ser | Leu | Val 300 | Pro | Gly | Ala | Gln |
| Arg 305 | Phe | Glu | Lys | Met | Ile 310 | Gly | Gly | Leu | Tyr | Leu 315 | Gly | Glu | Leu | Val | Arg 320 |
| Leu | Val | Leu | Val | His 325 | Leu | Ser | Gln | His | Gly 330 | Val | Leu | Phe | Gly | Gly 335 | Cys |
| Ala | Ser | Pro | Ala 340 | Leu | Leu | Ser | Gln | Asn 345 | Ser | Ile | Leu | Leu | Glu 350 | His | Val |
| Ala | Lys | Met 355 | Glu | Asp | Pro | Ala | Thr 360 | Gly | Ile | Ala | His | Val 365 | His | Thr | Val |
| Leu | Gln 370 | Gly | Leu | Gly | Leu | Ser 375 | Pro | Gln | Ala | Ser | Asp 380 | Ala | Glu | Leu | Val |
| Gln 385 | Arg | Val | Cys | Met | Ala 390 | Val | Cys | Thr | Arg | Ala 395 | Ala | Gln | Leu | Cys | Ala 400 |
| Ser | Ala | Leu | Ala | Ala 405 | Val | Leu | Ser | Arg | Leu 410 | Gln | His | Ser | Arg | Glu 415 | Gln |
| Gln | Thr | Leu | His 420 | Val | Ala | Val | Ala | Thr 425 | Gly | Gly | Arg | Val | Phe 430 | Glu | Trp |
| His | Pro | Arg 435 | Phe | Leu | Cys | Ile | Leu 440 | Lys | Glu | Thr | Val | Met 445 | Leu | Leu | Ala |
| Pro | Glu 450 | Cys | Asp | Val | Ser | Phe 455 | Ile | Pro | Ser | Val | Asp 460 | Gly | Gly | Gly | Arg |
| Gly 465 | Val | Ala | Met | Val | Thr 470 | Ala | Val | Ala | Ala | Arg 475 | Leu | Ala | Thr | His | Arg 480 |
| Arg | Ile | Leu | Glu | Glu 485 | Thr | Leu | Ala | Pro | Phe 490 | Gln | Leu | Ser | Leu | Glu 495 | Gln |
| Leu | Thr | Ala | Val 500 | Gln | Ala | Gln | Met | Arg 505 | Glu | Ala | Met | Ile | Arg 510 | Gly | Leu |
| Gln | Gly | Glu 515 | Ser | Ser | Ser | Leu | Arg 520 | Met | Leu | Pro | Thr | Tyr 525 | Val | Arg | Ala |
| Thr | Pro 530 | Asp | Gly | Ser | Glu | Arg 535 | Gly | Asp | Phe | Leu | Ala 540 | Leu | Asp | Leu | Gly |
| Gly 545 | Thr | Asn | Phe | Arg | Val 550 | Leu | Leu | Val | Arg | Val 555 | Ala | Glu | Gly | Ser | Val 560 |
| Gln | Ile | Thr | Asn | Gln 565 | Val | Tyr | Ser | Ile | Pro 570 | Glu | Tyr | Val | Ala | Gln 575 | Gly |
| Ser | Gly | Gln | Lys 580 | Leu | Phe | Asp | His | Ile 585 | Val | Asp | Cys | Ile | Val 590 | Asp | Phe |
| Gln | Lys | Arg 595 | Gln | Gly | Leu | Ser | Gly 600 | Gln | Ser | Leu | Pro | Leu 605 | Gly | Phe | Thr |
| Phe | Ser 610 | Phe | Pro | Cys | Lys | Gln 615 | Leu | Gly | Leu | Asp | Gln 620 | Gly | Ile | Leu | Leu |

| Asn | Trp | Thr | Lys | Gly | Phe | Asn | Ala | Ser | Gly | Cys | Glu | Gly | Gln | Asp | Val |
| 625 | | | | 630 | | | | | 635 | | | | | | 640 |

| Val | Tyr | Leu | Leu | Arg | Glu | Ala | Ile | Arg | Arg | Gln | Ala | Val | Glu | Leu |
| | | | | 645 | | | | | 650 | | | | | 655 |

| Asn | Val | Val | Ala | Ile | Val | Asn | Asp | Thr | Val | Gly | Thr | Met | Met | Ser | Cys |
| | | | 660 | | | | | 665 | | | | | 670 | | |

| Gly | Tyr | Asp | Asp | Pro | Cys | Cys | Glu | Met | Gly | Leu | Ile | Val | Gly | Thr | Gly |
| | | 675 | | | | | 680 | | | | | 685 | | | |

| Thr | Asn | Ala | Cys | Tyr | Met | Glu | Glu | Leu | Arg | Asn | Val | Ala | Ser | Val | Pro |
| | 690 | | | | | 695 | | | | | 700 | | | | |

| Gly | Asp | Ser | Gly | His | Met | Cys | Ile | Asn | Met | Glu | Trp | Gly | Ala | Phe | Gly |
| 705 | | | | | 710 | | | | | 715 | | | | | 720 |

| Asp | Asp | Gly | Ser | Leu | Ser | Met | Leu | Gly | Thr | Cys | Phe | Asp | Ala | Ser | Val |
| | | | | 725 | | | | | 730 | | | | | 735 | |

| Asp | Gln | Ala | Ser | Ile | Asn | Pro | Gly | Lys | Gln | Arg | Phe | Glu | Lys | Met | Ile |
| | | | 740 | | | | | 745 | | | | | 750 | | |

| Ser | Gly | Met | Tyr | Leu | Gly | Glu | Ile | Val | Arg | His | Ile | Leu | Leu | His | Leu |
| | | 755 | | | | | 760 | | | | | 765 | | | |

| Thr | Ser | Leu | Gly | Val | Leu | Phe | Arg | Gly | Gln | Lys | Thr | Gln | Cys | Leu | Gln |
| | 770 | | | | | 775 | | | | | 780 | | | | |

| Thr | Arg | Asp | Ile | Phe | Lys | Thr | Lys | Phe | Leu | Ser | Glu | Ile | Glu | Ser | Asp |
| 785 | | | | | 790 | | | | | 795 | | | | | 800 |

| Ser | Leu | Ala | Leu | Arg | Gln | Val | Arg | Ala | Ile | Leu | Glu | Asp | Leu | Gly | Leu |
| | | | | 805 | | | | | 810 | | | | | 815 | |

| Thr | Leu | Thr | Ser | Asp | Asp | Ala | Leu | Met | Val | Leu | Glu | Val | Cys | Gln | Ala |
| | | | 820 | | | | | 825 | | | | | 830 | | |

| Val | Ser | Arg | Arg | Ala | Ala | Gln | Leu | Cys | Gly | Ala | Gly | Val | Ala | Ala | Val |
| | | 835 | | | | | 840 | | | | | 845 | | | |

| Val | Glu | Lys | Ile | Arg | Glu | Asn | Arg | Gly | Leu | Gln | Glu | Leu | Thr | Val | Ser |
| | 850 | | | | | 855 | | | | | 860 | | | | |

| Val | Gly | Val | Asp | Gly | Thr | Leu | Tyr | Lys | Leu | His | Pro | His | Phe | Ser | Arg |
| 865 | | | | | 870 | | | | | 875 | | | | | 880 |

| Leu | Val | Ser | Val | Thr | Val | Arg | Lys | Leu | Ala | Pro | Gln | Cys | Thr | Val | Thr |
| | | | | 885 | | | | | 890 | | | | | 895 | |

| Phe | Leu | Gln | Ser | Glu | Asp | Gly | Ser | Gly | Lys | Gly | Ala | Ala | Leu | Val | Thr |
| | | | 900 | | | | | 905 | | | | | 910 | | |

| Arg | Val | Ala | Cys | Arg | Leu | Thr | Gln | Met | Ala | Cys | Val |
| | | | 915 | | | | | 920 | | | |

( 2 ) INFORMATION FOR SEQ ID NO:19:

( i ) SEQUENCE CHARACTERISTICS:
      ( A ) LENGTH: 1769 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:19:

| | | | | | | |
|---|---|---|---|---|---|---|
| TCTAGAGGCC | ACCGGTCTCT | CACAGCGCAG | CATAGCTAGG | AAAAGTCAGT | CAACACTGAG | 60 |
| GACATTTCCC | TGGAACCACA | TGGCCCCTCC | TAGAGGCCGC | CGGGCCTGAG | GAGGCCTTGG | 120 |
| TGGGGAAGGG | GCCAGAAGTG | AACAATGAAA | AAGAGGAAGC | TGTTGCTGCA | ATCAGCCTGA | 180 |
| GGCGGACATC | ATCGTTCTCT | GAGGCCCGTG | GCTGGCTGGG | ACTCCGTGAG | AGAGGCCTGG | 240 |
| ACGATTTCTA | CTTTGGAAAT | CTTGCGGAAC | ACTGAGGGGG | TCCCAGTTCA | CCTGGGCTGG | 300 |
| TGGCTGCGCA | GATGCTGGAT | GACAGAGCCA | GGATGGAGGC | CACCAAGAAG | GAAAAGGTCG | 360 |

-continued

| | | | | | |
|---|---|---|---|---|---|
| AGCAGATCCT | GGCAGAGTTC | CAGCTGCAGG | AGGAAGACCT | GAAGAAGGTG | ATGAGCCGGA | 420 |
| TGCAGAAGGA | GATGGACCGT | GGCCTGAGGC | TGGAGACCCA | CGAGGAGGCC | AGTGTAAAGA | 480 |
| TGTTACCCAC | CTACGTGCGT | TCCACCCCAG | AAGGCTCAGA | AGTCGGAGAC | TTTCTCTCCT | 540 |
| TAGACCTGGG | AGGAACCAAC | TTCAGAGTGA | TGCTGGTCAA | AGTGGGAGAG | GGGGAGGCAG | 600 |
| GGCAGTGGAG | CGTGAAGACA | AAACACCAGA | TGTACTCCAT | CCCCGAGGAC | GCCATGACGG | 660 |
| GCACTGCCGA | GATGCTCTTT | GACTACATCT | CTGAATGCAT | CTCTGACTTC | CTTGACAAGC | 720 |
| ATCAGATGAA | GCACAAGAAA | CTGCCCCTGG | GCTTCACCTT | CTCCTTCCCT | GTGAGGCACG | 780 |
| AAGACCTAGA | CAAGGGCATC | CTCCTCAATT | GGACCAAGGG | CTTCAAGGCC | TCTGGAGCAG | 840 |
| AAGGGAACAA | CATCGTAGGA | CTTCTCCGAG | ATGCTATCAA | GAGGAGAGGG | GACTTTGAGA | 900 |
| TGGATGTGGT | GGCAATGGTG | AACGACACAG | TGGCCACAAT | GATCTCCTGC | TACTATGAAG | 960 |
| ACCGCCAATG | TGAGGTCGGC | ATGATTGTGG | GCACTGGCTG | CAATGCCTGC | TACATGGAGG | 1020 |
| AAATGCAGAA | TGTGGAGCTG | GTGGAAGGGG | ATGAGGGACG | CATGTGCGTC | AACACGGAGT | 1080 |
| GGGGCGCCTT | CGGGGACTCG | GGCGAGCTGG | ATGAGTTCCT | ACTGGAGTAT | GACCGGATGG | 1140 |
| TGGATGAAAG | CTCAGCGAAC | CCCGGTCAGC | AGCTGTACGA | GAAGATCATC | GGTGGGAAGT | 1200 |
| ATATGGGCGA | GCTGGTACGA | CTTGTGCTGC | TTAAGCTGGT | GGACGAGAAC | CTTCTGTTCC | 1260 |
| ACGGAGAGGC | CTCGGAGCAG | CTGCGCACGC | GTGGTGCTTT | TGAGACCCGT | TTCGTGTCAC | 1320 |
| AAGTGGAGAG | CGACTCCGGG | GACCGAAAGC | AGATCCACAA | CATCCTAAGC | ACTCTGGGGC | 1380 |
| TTCGACCCTC | TGTCACCGAC | TGCGACATTG | TGCGCCGTGC | CTGTGAAAGC | GTGTCCACTC | 1440 |
| GCGCCGCCCA | TATGTGCTCC | GCAGGACTAG | CTGGGGTCAT | AAATCGCATG | CGCGAAAGCC | 1500 |
| GCAGTGAGGA | CGTGATGCGC | ATCACTGTGG | GCGTGGATGG | CTCCGTGTAC | AAGCTGCACC | 1560 |
| CGAGCTTCAA | GGAGCGGTTT | CACGCCAGTG | TGCGCAGGCT | GACACCCAAC | TGCGAAATCA | 1620 |
| CCTTCATCGA | ATCAGAGGAG | GGCAGCGGCA | GGGAGCCGC | ACTGGTCTCT | GCGGTGGCCT | 1680 |
| GCAAGAAGGC | TTGCATGCTG | GCCCAGTGAA | ATCCAGGTCA | TATGGACCGG | GACCTGGGTT | 1740 |
| CCACGGGGGT | TCCACGGGGA | TCCTCTAGA | | | | 1769 |

( 2 ) INFORMATION FOR SEQ ID NO:20:

( i ) SEQUENCE CHARACTERISTICS:
        ( A ) LENGTH: 465 amino acids
        ( B ) TYPE: amino acid
        ( C ) STRANDEDNESS: single
        ( D ) TOPOLOGY: linear ( x i ) SEQUENCE DESCRIPTION: SEQ ID NO:20:

```
Met Leu Asp Asp Arg Ala Arg Met Glu Ala Thr Lys Lys Glu Lys Val
 1               5                  10                  15

Glu Gln Ile Leu Ala Glu Phe Gln Leu Gln Glu Glu Asp Leu Lys Lys
             20                  25                  30

Val Met Ser Arg Met Gln Lys Glu Met Asp Arg Gly Leu Arg Leu Glu
         35                  40                  45

Thr His Glu Glu Ala Ser Val Lys Met Leu Pro Thr Tyr Val Arg Ser
     50                  55                  60

Thr Pro Glu Gly Ser Glu Val Gly Asp Phe Leu Ser Leu Asp Leu Gly
 65                  70                  75                  80

Gly Thr Asn Phe Arg Val Met Leu Val Lys Val Gly Glu Gly Glu Ala
                 85                  90                  95

Gly Gln Trp Ser Val Lys Thr Lys His Gln Met Tyr Ser Ile Pro Glu
                100                 105                 110
```

-continued

| | | | | | | | | | | | | | | |
|---|---|---|---|---|---|---|---|---|---|---|---|---|---|---|
| Asp | Ala | Met 115 | Thr | Gly | Thr | Ala | Glu 120 | Met | Leu | Phe | Asp | Tyr 125 | Ile | Ser | Glu |
| Cys | Ile 130 | Ser | Asp | Phe | Leu | Asp 135 | Lys | His | Gln | Met | Lys 140 | His | Lys | Lys | Leu |
| Pro 145 | Leu | Gly | Phe | Thr | Phe 150 | Ser | Phe | Pro | Val | Arg 155 | His | Glu | Asp | Leu | Asp 160 |
| Lys | Gly | Ile | Leu | Leu 165 | Asn | Trp | Thr | Lys | Gly 170 | Phe | Lys | Ala | Ser | Gly 175 | Ala |
| Glu | Gly | Asn | Asn 180 | Ile | Val | Gly | Leu | Leu 185 | Arg | Asp | Ala | Ile | Lys 190 | Arg | Arg |
| Gly | Asp | Phe 195 | Glu | Met | Asp | Val | Val 200 | Ala | Met | Val | Asn | Asp 205 | Thr | Val | Ala |
| Thr | Met 210 | Ile | Ser | Cys | Tyr | Tyr 215 | Glu | Asp | Arg | Gln | Cys 220 | Glu | Val | Gly | Met |
| Ile 225 | Val | Gly | Thr | Gly | Cys 230 | Asn | Ala | Cys | Tyr | Met 235 | Glu | Glu | Met | Gln | Asn 240 |
| Val | Glu | Leu | Val | Glu 245 | Gly | Asp | Glu | Gly | Arg 250 | Met | Cys | Val | Asn | Thr 255 | Glu |
| Trp | Gly | Ala | Phe 260 | Gly | Asp | Ser | Gly | Glu 265 | Leu | Asp | Glu | Phe | Leu 270 | Leu | Glu |
| Tyr | Asp | Arg 275 | Met | Val | Asp | Glu | Ser 280 | Ser | Ala | Asn | Pro | Gly 285 | Gln | Gln | Leu |
| Tyr | Glu 290 | Lys | Ile | Ile | Gly | Gly 295 | Lys | Tyr | Met | Gly | Glu 300 | Leu | Val | Arg | Leu |
| Val 305 | Leu | Leu | Lys | Leu | Val 310 | Asp | Glu | Asn | Leu | Leu 315 | Phe | His | Gly | Glu | Ala 320 |
| Ser | Glu | Gln | Leu | Arg 325 | Thr | Arg | Gly | Ala | Phe 330 | Glu | Thr | Arg | Phe 335 | Val | Ser |
| Gln | Val | Glu | Ser 340 | Asp | Ser | Gly | Asp | Arg 345 | Lys | Gln | Ile | His | Asn 350 | Ile | Leu |
| Ser | Thr | Leu 355 | Gly | Leu | Arg | Pro | Ser 360 | Val | Thr | Asp | Cys | Asp 365 | Ile | Val | Arg |
| Arg | Ala 370 | Cys | Glu | Ser | Val | Ser 375 | Thr | Arg | Ala | Ala | His 380 | Met | Cys | Ser | Ala |
| Gly 385 | Leu | Ala | Gly | Val | Ile 390 | Asn | Arg | Met | Arg | Glu 395 | Ser | Arg | Ser | Glu | Asp 400 |
| Val | Met | Arg | Ile | Thr 405 | Val | Gly | Val | Asp | Gly 410 | Ser | Val | Tyr | Lys | Leu 415 | His |
| Pro | Ser | Phe | Lys 420 | Glu | Arg | Phe | His | Ala 425 | Ser | Val | Arg | Arg | Leu 430 | Thr | Pro |
| Asn | Cys | Glu 435 | Ile | Thr | Phe | Ile | Glu 440 | Ser | Glu | Glu | Gly | Ser 445 | Gly | Arg | Gly |
| Ala | Ala | Leu 450 | Val | Ser | Ala | Val 455 | Ala | Cys | Lys | Lys | Ala 460 | Cys | Met | Leu | Ala |
| Gln 465 | | | | | | | | | | | | | | | |

( 2 ) INFORMATION FOR SEQ ID NO:21:

( i ) SEQUENCE CHARACTERISTICS:
        ( A ) LENGTH: 2297 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

| | | | | | | |
|---|---|---|---|---|---|---|
| AACAGGTGGC | CTCAGGAGTC | AGGAACATCT | CTACTTCCCC | AACGACCCCT | GGGTTGTCCT | 60 |
| CTCAGAGATG | GCTATGGATA | CTACAAGGTG | TGGAGCCCAG | TTGTTGACTC | TGGTCGAGCA | 120 |
| GATCCTGGCA | GAGTTCCAGC | TGCAGGAGGA | AGACCTGAAG | AAGGTGATGA | GCCGGATGCA | 180 |
| GAAGGAGATG | GACCGTGGCC | TGAGGCTGGA | GACCCACGAG | GAGGCCAGTG | TAAAGATGTT | 240 |
| ACCCACCTAC | GTGCGTTCCA | CCCCAGAAGG | CTCAGAAGTC | GGAGACTTTC | TCTCCTTAGA | 300 |
| CCTGGGAGGA | ACCAACTTCA | GAGTGATGCT | GGTCAAAGTG | GGAGAGGGGG | AGGCAGGGCA | 360 |
| GTGGAGCGTG | AAGACAAAAC | ACCAGATGTA | CTCCATCCCC | GAGGACGCCA | TGACGGGCAC | 420 |
| TGCCGAGATG | CTCTTTGACT | ACATCTCTGA | ATGCATCTCT | GACTTCCTTG | ACAAGCATCA | 480 |
| GATGAAGCAC | AAGAAACTGC | CCCTGGGCTT | CACCTTCTCC | TTCCCTGTGA | GGCACGAAGA | 540 |
| CCTAGACAAG | GGCATCCTCC | TCAATTGGAC | CAAGGGCTTC | AAGGCCTCTG | GAGCAGAAGG | 600 |
| GAACAACATC | GTAGGACTTC | TCCGAGATGC | TATCAAGAGG | AGAGGGACT | TTGAGATGGA | 660 |
| TGTGGTGGCA | ATGGTGAACG | ACACAGTGGC | CACAATGATC | TCCTGCTACT | ATGAAGACCG | 720 |
| CCAATGTGAG | GTCGGCATGA | TTGTGGGCAC | TGGCTGCAAT | GCCTGCTACA | TGGAGGAAAT | 780 |
| GCAGAATGTG | GAGCTGGTGG | AAGGGGATGA | GGGACGCATG | TGCGTCAACA | CGGAGTGGGG | 840 |
| CGCCTTCGGG | GACTCGGGCG | AGCTGGATGA | GTTCCTACTG | GAGTATGACC | GGATGGTGGA | 900 |
| TGAAAGCTCA | GCGAACCCCG | GTCAGCAGCT | GTACGAGAAG | ATCATCGGTG | GAAGTATAT | 960 |
| GGGCGAGCTG | GTACGACTTG | TGCTGCTTAA | GCTGGTGGAC | GAGAACCTTC | TGTTCCACGG | 1020 |
| AGAGGCCTCG | GAGCAGCTGC | GCACGCGTGG | TGCTTTTGAG | ACCCGTTTCG | TGTCACAAGT | 1080 |
| GGAGAGCGAC | TCCGGGGACC | GAAAGCAGAT | CCACAACATC | CTAAGCACTC | TGGGGCTTCG | 1140 |
| ACCCTCTGTC | ACCGACTGCG | ACATTGTGCG | CCGTGCCTGT | GAAAGCGTGT | CCACTCGCGC | 1200 |
| CGCCCATATG | TGCTCCGCAG | GACTAGCTGG | GGTCATAAAT | CGCATGCGCG | AAAGCCGCAG | 1260 |
| TGAGGACGTG | ATGCGCATCA | CTGTGGGCGT | GGATGGCTCC | GTGTACAAGC | TGCACCCGAG | 1320 |
| CTTCAAGGAG | CGGTTTCACG | CCAGTGTGCG | CAGGCTGACA | CCCAACTGCG | AAATCACCTT | 1380 |
| CATCGAATCA | GAGGAGGGCA | GCGGCAGGGG | AGCCGCACTG | GTCTCTGCGG | TGGCCTGCAA | 1440 |
| GAAGGCTTGC | ATGCTGGCCC | AGTGAAATCC | AGGTCATATG | GACCGGGACC | TGGGTTCCAC | 1500 |
| GGGGACTCCA | CACACCACAA | ATGCTCCAG | CCCACCGGGG | CAGGAGACCT | ATTCTGCTGC | 1560 |
| TACCCCTGGA | AAATGGGGAG | AGGCCCCTGC | AAGCCGAGTC | GGCCAGTGGG | ACAGCCCTAG | 1620 |
| GGCTCTCAGC | CTGGGGCAGG | GGGCTGGGAG | GAAGAAGAGG | ATCAGAGGCG | CCAAGGCCTT | 1680 |
| TCTTGCTAGA | ATCAACTACA | GAAAATGGCG | GAAAATACTC | AGGACTTGCA | CTTTCACGAT | 1740 |
| TCTTGCTTCC | CAAGCGTGGG | TCTGGCCTCC | CAAGGGAATG | CTTCCTGGAC | CTTGCAATGG | 1800 |
| CCTGGCTTCC | CTGGGGGGA | CACACCTTCA | TGGGGAGGTA | ACTTCAGCAG | TTCGGCCAGA | 1860 |
| CCAGACCCCA | GGAGAGTAAG | GGCTGCTGGT | CACCCAGACC | TGGCTGTTTT | CTTGTCTGTG | 1920 |
| GCTGAAGAGG | CCGGGGAGCC | ATGAGAGACT | GACTATCCGG | CTACATGGAG | AGGACTTTCC | 1980 |
| AGGCATGAAC | ATGCCAGAGA | CTGTTGCCTT | CATATACCTC | CACCCGAGTG | GCTTACAGTT | 2040 |
| CTGGGATGAA | CCCTCCCAGG | AGATGCCAGA | GGTTAGAGCC | CCAGAGTCCT | TGCTCTAAGG | 2100 |
| GGACCAGAAA | GGGGAGGCCT | CACTCTGCAC | TATTCAAGCA | GGAATCATCT | CCAACACTCA | 2160 |
| GGTCCCTGAC | CCAGGAGGAA | GAAGCCACCC | TCAGTGTCCC | TCCAAGAGAC | CACCCAGGTC | 2220 |
| CTTCTCTCCC | TCGTTCCCAA | ATGCCAGCCT | CTCTACCTGG | GACTGTGGGG | GAGTTTTAA | 2280 |
| TTAAATATTT | AAAACTT | | | | | 2297 |

( 2 ) INFORMATION FOR SEQ ID NO:22:

(i) SEQUENCE CHARACTERISTICS:
  (A) LENGTH: 465 amino acids
  (B) TYPE: amino acid
  (C) STRANDEDNESS: single
  (D) TOPOLOGY: linear (xi) SEQUENCE DESCRIPTION: SEQ ID NO:22:

```
Met Ala Met Asp Thr Thr Arg Cys Gly Ala Gln Leu Leu Thr Leu Val
 1               5                  10                  15

Glu Gln Ile Leu Ala Glu Phe Gln Leu Gln Glu Glu Asp Leu Lys Lys
            20                  25                  30

Val Met Ser Arg Met Gln Lys Glu Met Asp Arg Gly Leu Arg Leu Glu
        35                  40                  45

Thr His Glu Glu Ala Ser Val Lys Met Leu Pro Thr Tyr Val Arg Ser
    50                  55                  60

Thr Pro Glu Gly Ser Glu Val Gly Asp Phe Leu Ser Leu Asp Leu Gly
65                  70                  75                  80

Gly Thr Asn Phe Arg Val Met Leu Val Lys Val Gly Glu Gly Glu Ala
                85                  90                  95

Gly Gln Trp Ser Val Lys Thr Lys His Gln Met Tyr Ser Ile Pro Glu
            100                 105                 110

Asp Ala Met Thr Gly Thr Ala Glu Met Leu Phe Asp Tyr Ile Ser Glu
            115                 120                 125

Cys Ile Ser Asp Phe Leu Asp Lys His Gln Met Lys His Lys Lys Leu
    130                 135                 140

Pro Leu Gly Phe Thr Phe Ser Phe Pro Val Arg His Glu Asp Leu Asp
145                 150                 155                 160

Lys Gly Ile Leu Leu Asn Trp Thr Lys Gly Phe Lys Ala Ser Gly Ala
                165                 170                 175

Glu Gly Asn Asn Ile Val Gly Leu Leu Arg Asp Ala Ile Lys Arg Arg
            180                 185                 190

Gly Asp Phe Glu Met Asp Val Val Ala Met Val Asn Asp Thr Val Ala
            195                 200                 205

Thr Met Ile Ser Cys Tyr Tyr Glu Asp Arg Gln Cys Glu Val Gly Met
    210                 215                 220

Ile Val Gly Thr Gly Cys Asn Ala Cys Tyr Met Glu Glu Met Gln Asn
225                 230                 235                 240

Val Glu Leu Val Glu Gly Asp Glu Gly Arg Met Cys Val Asn Thr Glu
                245                 250                 255

Trp Gly Ala Phe Gly Asp Ser Gly Glu Leu Asp Glu Phe Leu Leu Glu
            260                 265                 270

Tyr Asp Arg Met Val Asp Glu Ser Ser Ala Asn Pro Gly Gln Gln Leu
            275                 280                 285

Tyr Glu Lys Ile Ile Gly Gly Lys Tyr Met Gly Glu Leu Val Arg Leu
    290                 295                 300

Val Leu Leu Lys Leu Val Asp Glu Asn Leu Leu Phe His Gly Glu Ala
305                 310                 315                 320

Ser Glu Gln Leu Arg Thr Arg Gly Ala Phe Glu Thr Arg Phe Val Ser
                325                 330                 335

Gln Val Glu Ser Asp Ser Gly Asp Arg Lys Gln Ile His Asn Ile Leu
            340                 345                 350

Ser Thr Leu Gly Leu Arg Pro Ser Val Thr Asp Cys Asp Ile Val Arg
        355                 360                 365

Arg Ala Cys Glu Ser Val Ser Thr Arg Ala Ala His Met Cys Ser Ala
370                 375                 380
```

```
Gly Leu Ala Gly Val Ile Asn Arg Met Arg Glu Ser Arg Ser Glu Asp
385                 390                 395                 400

Val Met Arg Ile Thr Val Gly Val Asp Gly Ser Val Tyr Lys Leu His
                405                 410                 415

Pro Ser Phe Lys Glu Arg Phe His Ala Ser Val Arg Arg Leu Thr Pro
            420                 425                 430

Asn Cys Glu Ile Thr Phe Ile Glu Ser Glu Glu Gly Ser Gly Arg Gly
        435                 440                 445

Ala Ala Leu Val Ser Ala Val Ala Cys Lys Lys Ala Cys Met Leu Ala
    450                 455                 460

Gln
465
```

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:23:

CCGGATCCCA TGATTGAACA AGAT        24

(2) INFORMATION FOR SEQ ID NO:24:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (xi) SEQUENCE DESCRIPTION: SEQ ID NO:24:

CCCTACCTAA GAGAGAGAGA GAGAGAGAGA GAGAGAGAGA GATAAGAATA AGATTCTCTC    60

TCTCTCTCTC TCTCTCTC    78

(2) INFORMATION FOR SEQ ID NO:25:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:25:

CCGGATCCAG GTCGACGCCG GCCAA    25

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:26:

CGAGATCTTG CCAGCCAGTT GG    22

(2) INFORMATION FOR SEQ ID NO:27:

(i) SEQUENCE CHARACTERISTICS:
        (A) LENGTH: 25 base pairs
        (B) TYPE: nucleic acid
        (C) STRANDEDNESS: single (D) TOPOLOGY: linear (xi) SEQUENCE DESCRIPTION: SEQ ID NO:27:

CCCGGATCCC ACATACAGAC TTATT                              25

(2) INFORMATION FOR SEQ ID NO:28:

(i) SEQUENCE CHARACTERISTICS:
  (A) LENGTH: 28 base pairs
  (B) TYPE: nucleic acid
  (C) STRANDEDNESS: single
  (D) TOPOLOGY: linear (xi) SEQUENCE DESCRIPTION: SEQ ID NO:28:

CGGGATCCTC AGTTTTGGT GGCAGAGG                              28

(2) INFORMATION FOR SEQ ID NO:29:

(i) SEQUENCE CHARACTERISTICS:
  (A) LENGTH: 49 base pairs
  (B) TYPE: nucleic acid
  (C) STRANDEDNESS: single
  (D) TOPOLOGY: linear (xi) SEQUENCE DESCRIPTION: SEQ ID NO:29:

CTAGACTCCA TGCTCTGATG AGTCCGTGAG GACGAAACGT TCTGGTTCG            49

(2) INFORMATION FOR SEQ ID NO:30:

(i) SEQUENCE CHARACTERISTICS:
  (A) LENGTH: 49 base pairs
  (B) TYPE: nucleic acid
  (C) STRANDEDNESS: single
  (D) TOPOLOGY: linear (xi) SEQUENCE DESCRIPTION: SEQ ID NO:30:

GATCCGAACC AGAACGTTTC GTCCTCACGG ACTCATCAGA GCATGGAGT            49

(2) INFORMATION FOR SEQ ID NO:31:

(i) SEQUENCE CHARACTERISTICS:
  (A) LENGTH: 48 base pairs
  (B) TYPE: nucleic acid
  (C) STRANDEDNESS: single
  (D) TOPOLOGY: linear (xi) SEQUENCE DESCRIPTION: SEQ ID NO:31:

CTAGATCATG GTCCCCTGAT GAGTCCGTGA GGACGAAACT GTGTCATG             48

(2) INFORMATION FOR SEQ ID NO:32:

(i) SEQUENCE CHARACTERISTICS:
  (A) LENGTH: 48 base pairs
  (B) TYPE: nucleic acid
  (C) STRANDEDNESS: single
  (D) TOPOLOGY: linear (xi) SEQUENCE DESCRIPTION: SEQ ID NO:32:

GATCCATGAC ACAGTTTCGT CCTCACGGAC TCATCAGGGG ACCATGAT            48

(2) INFORMATION FOR SEQ ID NO:33:

(i) SEQUENCE CHARACTERISTICS:
  (A) LENGTH: 49 base pairs
  (B) TYPE: nucleic acid
  (C) STRANDEDNESS: single
  (D) TOPOLOGY: linear ( x i ) SEQUENCE DESCRIPTION: SEQ ID NO:33:

CTAGAGTTCC TCCAACTGAT GAGTCCGTGA GGACGAAATC CAAGGCCAG    49

( 2 ) INFORMATION FOR SEQ ID NO:34:

( i ) SEQUENCE CHARACTERISTICS:
        ( A ) LENGTH: 49 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:34:

GATCCTGGCC TTGGATTTCG TCCTCACGGA CTCATCAGTT GGAGGAACT    49

( 2 ) INFORMATION FOR SEQ ID NO:35:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:35:

CTGATGAGTC CGTGAGGACG AA    22

( 2 ) INFORMATION FOR SEQ ID NO:36:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:36:

TTTCCCCTCG AGCACCGCCC GGAACAGTAC C    31

( 2 ) INFORMATION FOR SEQ ID NO:37:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:37:

GTTGCGCCTC GAGCATGCTG ACGGTGGGGG    30

( 2 ) INFORMATION FOR SEQ ID NO:38:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:38:

GTTGGACTCG AGAGTCACCT AAGGGCCTAT G    31

( 2 ) INFORMATION FOR SEQ ID NO:39:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

GATTGGGAAG ACAATAGCAG GCATGC 26

( 2 ) INFORMATION FOR SEQ ID NO:40:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:40:

AGTCGCCTCT GCATGTCTGA GTTC 24

( 2 ) INFORMATION FOR SEQ ID NO:41:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:41:

CTTGAGCTCT TACATGGTGT CACG 24

( 2 ) INFORMATION FOR SEQ ID NO:42:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:42:

TCCCCAGGCG TGGGGTAGAA G 21

( 2 ) INFORMATION FOR SEQ ID NO:43:

( i ) SEQUENCE CHARACTERISTICS:
    ( A ) LENGTH: 1252 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:43:

GGGTATCTTT GCCCCGATGG ATGCTGGGCC TAGCCAGGGG CTCCCAGTCC CCAGGCGTGG 60
GGTAGAAGTT GGACTCTATA GTCACCTAAG GGCCTATGTT GCAGTCCTGG TCTCAGGCAC 120
GCGGCCTGCA GGAGAGGCTT AAAAGAAGAG AAACTGCACA CAATGGCTAG GTCACCGGCG 180
TTAAAGCTAA GCAAACCCAG CGCTACTCCT GGGCAGCAAC TGCAAAGCGT TTCTTCAGGT 240
CCCTCACCTG TAGAATCAGA GCGGTAGTCG CCTCTGCATG TCTGAGTTCT TACATGTCGT 300
AATGTACAAA CACGATTTCC CCTCAATCAC CGCCCGGAAC AGTACCTCCA ACTTCCCAGA 360
CCCGGATGCC CCAAGAGCCA GAGTAGGGTG GGAAAATCGG GACAGGCCCC CAAATTCCAC 420
TCGGGGCCT TGAGCTCTTA CATGGTGTCA CGGGGCAGG TAGTTTGGGT TTAGCAATGT 480
GAACTCTGAC AATTTGGGAT GTAGAGCTGG TGGGCCATCG TGGACGCCA AGCATCATCC 540
TTAGAGTTTG GATCCTTTAG GGCAGGCAGG CACAGGGACC CAGTGCGAGA TCAGTGAAGC 600
CGCCCAGTTT CGGCTTCCGC TCTTTTTCCA CGCCCACTTG CGTGCTTCTC CAACAGTGTG 660
GATGGGAGGG GTGGGGACG AGCCCTAATC TCCGAGGAAG GGGTGTGGCC CCGTTCGTGT 720
TCTCCAGTTT GTGGCGTCCT GGATCTGTCC TCTGGTCCCC TCCAGATCGT GTCCACACC 780
CACCCGTTCA GGCATGGCAC TGTGCCGCCA CGCGTGACCG TGCGCTCCTT ACGTGGGGA 840

-continued

| | | | | | | |
|---|---|---|---|---|---|---|
| CGTGCAGGGT | GCTGCCTCCT | TTCCGGTGCG | GGAGGGAGCG | GCCGTCTTTC | TCCTGCTCTG | 900 |
| GCTGGGAAGC | CCCAGCCATT | GCGCTGCAGA | GGAGACTTGC | AGCCAATGGG | GACTGAGGAA | 960 |
| GTGGGCCGGC | TGGCGGTTGT | CACCCTCCCG | GGGACCGGAG | CTCCGAGGTC | TGGAGAGCGC | 1020 |
| AGGCAGACGC | CCGCCCCGCC | CGGGGACTGA | GGGGGAGGAG | CGAAGGGAGG | AGGAGGTGGA | 1080 |
| GTCTCCGATC | TGCCGCTGGA | GGACCACTGC | TCACCAGGCT | ACTGAGGAGC | CACTGGCCCC | 1140 |
| ACACCTGCTT | TTCCGCATCC | CCCACCGTCA | GCATGATCGC | CGCGCAACTA | CTGGCCTATT | 1200 |
| ACTCACCGAG | CTGAAGGATG | ACCAAGTCAA | AAAGGTGAGC | CCCGCCGGCG | CC | 1252 |

METHODS AND COMPOSITIONS FOR INHIBITING HEXOKINASE

BACKGROUND OF THE INVENTION

1. Field of the Invention

The present invention relates generally to the field of cellular biochemistry and also to the field of diabetes. More particularly, it provides compositions and methods for inhibiting hexokinases in mammalian cells. Specifically provided are agents that stimulate the production of trehalose-6-phosphate; hexokinase-specific ribozymes and agents that competitively reduce hexokinase activity, e.g., by displacing hexokinase from mitochondria. Cells incorporating such agents and their respective genes, and advantageous methods of making and using cells with reduced hexokinase activity are also provided.

2. Description of the Related Art

The participation of the pancreatic islets of Langerhans in fuel homeostasis is mediated in large part by their ability to respond to changes in circulating levels of key metabolic fuels by secreting peptide hormones. Insulin secretion from islet β-cells is stimulated by amino acids, three-carbon sugars such as glyceraldehyde and, most prominently, by glucose. The capacity of normal islet β-cells to sense a rise in blood glucose concentration and to respond to elevated levels of glucose (as occurs following ingestion of a carbohydrate containing meal) by secreting insulin is critical to control of blood glucose levels. Increased insulin secretion in response to a glucose load prevents chronic hyperglycemia in normal individuals by stimulating glucose uptake into peripheral tissues, particularly muscle and adipose tissue.

Individuals in which islet β-cell function is impaired suffer from diabetes. Insulin-dependent diabetes mellitus (IDDM, also known as Juvenile-onset, or Type I diabetes) represents approximately 15% of all human diabetes. IDDM is distinct from non-insulin dependent diabetes (NIDDM) in that only IDDM involves specific destruction of the insulin producing β-cells of the islets of Langerhans in the pancreas. The destruction of β-cells in IDDM appears to be a result of specific autoimmune attack, in which the patient's own immune system recognizes and destroys the β-cells, but not the surrounding α (glucagon producing) or δ (somatostatin producing) cells that comprise the islet.

The precise events involved in β-cell recognition and destruction in IDDM are currently unknown, but involve both the cellular and humoral components of the immune system. In IDDM, islet β-cell destruction is ultimately the result of cellular mechanisms, in which cytotoxic T cells destroy β cells which are erroneously perceived as foreign or harmful. The humoral component of the immune system, comprised of the antibody-producing B cells, is also inappropriately active in IDDM patients, who have serum antibodies against various β cell proteins.

Glucose stimulates de novo insulin biosynthesis in β-cells by increasing transcription, mRNA stability, translation, and protein processing. Glucose also rapidly stimulates the release of pre-stored insulin. Glucose transport into the β-cell and metabolism of this sugar are absolute requirements for insulin secretion, leading to the hypothesis that its specific stimulatory effect is mediated by, and proportional to, its flux rate through glycolysis and related pathways.

The facilitated-diffusion type glucose transporter, GLUT-2, and the glucose phosphorylating enzyme, glucokinase, are known to be involved in the control of glucose metabolism in islet β-cells (U.S. Pat. No. 5,427,940). Both proteins are members of gene families; GLUT-2 is unique among the five-member family of glucose transporter proteins in that it has a distinctly higher $K_m$ and Vmax for glucose. Glucokinase is the high $K_m$ and high Vmax counterpart of GLUT-2 among the family of hexokinases. Importantly, both proteins have affinities for glucose that allow dramatic changes in their activities over the physiological range of glucose. These proteins thus work in concert as the "glucose-sensing apparatus" that modulates insulin secretion in response to changes in circulating glucose concentrations by regulating glycolytic flux.

Treatment for IDDM is still centered around self-injection of insulin once or twice daily. The development of new therapeutic strategies is therefore necessary. The possibility of islet or pancreas fragment transplantation has been investigated as a means for permanent insulin replacement (Lacy et al., 1986). However, this approach has been severely hampered by the difficulties associated with obtaining tissue, as well as the finding that transplanted islets are recognized and destroyed by the same autoimmune mechanism responsible for destruction of the patients original islet β cells.

U.S. Pat. No. 5,427,940 provided, for the first time, recombinant cells that secrete insulin in response to glucose. The generation of such artificial β cells is achieved through the introduction of one or more genes selected from the insulin gene, the glucokinase gene and the GLUT-2 glucose transporter gene, so as to provide an engineered cell having all three of these genes in a biologically functional and responsive configuration.

The availability of the engineered cells of U.S. Pat. No. 5,427,940 makes cell-based insulin replacement therapy for IDDM a realistic goal. However, while evidently of significant use, it appears that these cells are not optimal for IDDM treatment owing to the fact that the glucokinase:hexokinase activity ratio in such cells is not likely to result in insulin secretion at physiological glucose concentrations. Accordingly, it is evident that improvements are needed in the engineering of cells for use in the treatment of diabetes and in other applications.

SUMMARY OF THE INVENTION

The present invention seeks to overcome these and other drawbacks inherent in the prior art by providing compositions and methods for inhibiting hexokinase in mammalian cells. Metabolic inhibitors of hexokinase activity are provided in the form of agents that stimulate the production of trehalose-6-phosphate and molecular biological inhibitors of hexokinase are provided in the form of hexokinase-specific ribozymes. Further provided are agents that displace hexokinase from mitochondria and thus competitively reduce hexokinase activity. This group of agents includes inactive hexokinases and fragments thereof that retain mitochondrial binding functions and, also, hexokinase-glucokinase chimeras that further substitute glucokinase activity for hexokinase activity. All of the inhibitory agents may be provided in the form of a gene or vector that expresses the particular agent.

Mammalian cells including such hexokinase inhibitors are also provided, as are methods of making and using cells with reduced hexokinase activity. Important examples of mammalian cells that include hexokinase inhibitors are cells that have been engineered to secrete polypeptide hormones and other biologically active agents, as exemplified by cells that secrete insulin in response to glucose. The cells may be used in various in vitro and in vivo embodiments, such as, in the production of large quantities of proteins and in cellular-based delivery methods and treatment protocols.

Further aspects of the invention concern the role of low $K_m$ hexokinases as regulators of cell growth. These aspects are generally based on the Inventors' findings that inhibition of low $K_m$ hexokinase achieved using knockout technology significantly slows cell growth. Accordingly, methods of reducing the growth of a cell by inhibiting the ultimate activity of a low $K_m$ hexokinase form yet another aspect of the invention.

Accordingly, the present invention provides mammalian cells that comprise at least one inhibitor of a low $K_m$ hexokinase, the inhibitor selected from:

(a) an agent that stimulates the production of trehalose-6-phosphate;

(b) a low $K_m$ hexokinase-specific ribozyme; or (c) an agent that competitively reduces low $K_m$ hexokinase activity;

wherein said inhibitor is present in an amount effective to reduce the low $K_m$ hexokinase activity of the cell.

The cells of the invention will generally have a reduced a low $K_m$ hexokinase activity relative to a parent cell from which the instant cell was prepared. It is contemplated that cells in which the low $K_m$ hexokinase activity is reduced by any degree relative to control levels, i.e., levels within the cell prior to contact with an inhibitor, will be useful in the context of the present invention.

Depending on the intended use of the cells, cells in which a moderate hexokinase inhibition is achieved will still have utility. Such inhibition levels are contemplated to be those in which the low $K_m$ hexokinase activity is reduced by at least about 5%, about 10%, about 15%, about 20%, or about 25% relative to control levels. Of course, cells exhibiting more significant inhibition are also contemplated within the invention. Accordingly, cells in which the low $K_m$ hexokinase activity is reduced by about 30%, about 40%, about 50%, about 60% or even about 70% or higher, with respect to control levels, are contemplated as part of this invention and will be preferred in certain embodiments.

In certain embodiments, particularly where the cell in question is an engineered cell designed to secrete insulin in response to glucose, other parameters may be applied in assessing useful levels of low $K_m$ hexokinase inhibition. For example, it may be desired to determine the ratio of glucokinase to hexokinase (GK:HK ratio) and to monitor changes in this ratio as hexokinase is inhibited. It will be understood that a cell in which this ratio is changed to reflect the ratio commonly observed in functional or natural pancreatic β cells, or in which the ratio is changed towards this, will be an advantageous engineered cell in the context of this invention.

In certain preferred embodiments, it is contemplated that cells of this invention will have a low $K_m$ hexokinase activity that has been reduced to a level appropriate to confer more physiological insulin secretion capacity to the cell. This includes genetically engineered cells that have a near-homeostatic insulin secretion capacity.

"Engineered cells that exhibit more physiological insulin secretion" are cells that exhibit glucose-stimulated insulin secretion (GSIS) closer to the normal range than the parent cell from which they were prepared and, generally, also than the previously described engineered cells. In this regard, the maximal glucose response of previously described cell lines generally occurs at subphysiological glucose concentrations of between about 10 μM and about 100 μM.

The GSIS of normal islet β cells generally occurs at glucose concentrations of between about 3 mM to 20 mM, with ranges of 5 to 20 mM and 4 to 9 mM being frequently reported. Insulin responses in these ranges would therefore be described as "near-homeostatic insulin secretion." Cells that comprise an inhibitor in an amount effective to reduce the low $K_m$ hexokinase activity of the cell to a level sufficient to confer insulin secretion in response to an extracellular glucose concentration of between about 1 mM and about 20 μM will thus be most preferred. Extracellular glucose concentrations of "between about 1 μM and about 20 μM" will be understood to include each and every numerical value within this range, such as being about 1, 2, 3, 4, 5, 7.5, 10, 12, 14, 16, 18, and about 20 μM or so.

Any of the low $K_m$ hexokinases present within mammalian cells may be inhibited according to the present invention, that is hexokinase I, hexokinase II and/or hexokinase III. In embodiments concerning engineered cells for use in treating diabetes, the preferred target are hexokinase I and/or hexokinase II, as these are the predominant isoforms present in cell lines contemplated for such uses.

Irrespective of the type of inhibitor provided to a cell in order to inhibit hexokinase, it is generally preferred that the inhibitor be introduced into the cell by means of a recombinant gene that expresses the inhibitor. Generally, this will be achieved by introducing into the cell a recombinant vector that comprises a promoter operatively linked to a gene that encodes the inhibitor, where the promoter directs the expression of the inhibitor in the host cell. The construction and use of recombinant vectors and promoters is well known to those of skill in the art and is further described in detail herein.

In certain embodiments, the inhibitory agents for use in this invention is an agent, such as an enzyme, that stimulate the production of trehalose-6-phosphate. A currently preferred enzyme is trehalose-6-phosphate synthase, as may be exemplified by the yeast enzyme termed TPS1. Synthase genes from insects, blue-green algae and bacteria such as *E. coli* may also be used in these aspects of the invention.

Cells provided with a TPS1 enzyme that includes a contiguous amino acid sequence from SEQ ID NO:2 are currently preferred. The TPS1 protein may be advantageously provided to a cell by introducing into the cell a recombinant gene that includes a contiguous nucleic acid sequence from SEQ ID NO:1. Of course, it will be well understood that all biological functional equivalents of enzymes such as TPS1 are included within the scope of the present invention. In fact, the invention contemplates the use of any agent, whether biological or chemical, that result in an increase in trehalose-6-phosphate concentration within a mammalian cell.

Further aspects of the present invention concern mammalian cells that comprise a low $K_m$ hexokinase-specific ribozyme or a gene encoding such a ribozyme. As used herein, the term "a low $K_m$ hexokinase-specific ribozyme" means a nucleic acid sequence that comprises a ribozyme catalytic domain sequence in combination with a nucleic acid sequence that is complementary to and binds to an RNA transcript of a low $K_m$ hexokinase gene.

A number of ribozymes are known, virtually any one of which may be used in conjunction with the present invention. By way of example only, one may mention ribozyme catalytic domains from hammerhead ribozymes and from hairpin ribozyme structures. Specific examples include ribozyme sequences from RNaseP, hepatitis delta virus, avocado sunblotch viroid virus, lucerne transient streak, and tobacco ringspot virus.

In certain of these embodiments, the hexokinase-specific ribozyme will comprise a ribozyme catalytic domain linked to a nucleic acid sequence that is complementary to and binds to an RNA transcript of a hexokinase I gene; in other embodiments, the ribozyme will comprise a nucleic acid sequence that directs binding to a hexokinase II gene. The hexokinase nucleic acid sequence may be linked either to the 5' a or to the 3' end of the ribozyme sequence, although it is most preferred that the ribozyme sequence be linked at each end to a hexokinase nucleic acid sequence. In this manner, this hexokinase-specific sequences will flank the ribozyme catalytic sequence.

Hexokinase sequences of between about 6 and about 30 bases in length may be used in the aforementioned constructs, with sequences of between about 10 and about 15 bases in length being currently preferred. Hexokinase I-specific nucleic acid sequences are represented by contiguous sequences from SEQ ID NO:13; with hexokinase II-specific sequences being represented by contiguous sequences from SEQ ID NO:15. Exemplary low $K_m$ hexokinase-specific ribozymes for use in the present invention include SEQ ID NO:3, SEQ ID NO:4, and SEQ ID NO:5.

In still further embodiments, the inhibitory agents for use in the present invention will be agents that competitively reduce low $K_m$ hexokinase activity. One example of such an agent is the glucokinase enzyme. Other possible examples include glycerol kinase. Preferred examples of these agents are agents that lack low $K_m$ hexokinase activity and that displace low $K_m$ hexokinase from mitochondria. A number of such constructs are contemplated to be useful in the context of the present invention.

One broad group of such inhibitors are those that simply compete for hexokinase binding sites and consequentially displace endogenous low $K_m$ hexokinases from their mitochrondial binding sites within an intact cell. Such "displacing agents" will generally comprise a mitochondrial binding region from the N-terminal domain of a low $K_m$ hexokinase, such as hexokinase I or hexokinase II.

The term "mitochrondial binding region from the N-terminal domain," as used herein, includes constructs of between about 15 amino acids in length and about 455 amino acids in length, with all intermediates between these two extremes being contemplated. Such mitochondrial binding regions are exemplified by peptides, polypeptides and proteins that include a contiguous amino acid sequence from SEQ ID NO:7 and those that include a contiguous sequence from between about position 1 to about position 455 of SEQ ID NO:16. Currently preferred recombinant genes that encode such mitochondrial binding agents are those that include a contiguous nucleic acid sequence from SEQ ID NO:6 and those that include a contiguous sequence from between about position 1 to about position 1563 of SEQ ID NO:15.

Constructs that consist essentially of the N-terminal domain of a low $K_m$ hexokinase will be preferred for use in certain aspects of the invention. This is based upon the belief that this domain will readily form a correctly folded structure that effectively competes with endogenous hexokinase enzymes.

Constructs capable of displacing low $K_m$ hexokinases from mitochondria, whilst simultaneously providing to the cell a high $K_m$ hexokinase (gluconase) activity form another preferred aspect of the present invention. Of course, it will be understood that such "displacement-replacement" constructs will not themselves exhibit low $K_m$ hexokinase activity. These constructs will generally comprise a mitochondrial binding peptide, polypeptide or protein from the N-terminal domain of a low $K_m$ hexokinase operatively linked to at least the catalytic domain of a glucokinase enzyme (hexokinase IV).

Appropriate hexokinase IV domains that may be used in this manner are those that include a contiguous amino acid sequence from SEQ ID NO:20 or SEQ ID NO:22, so long as the domains exhibit appropriate hexokinase IV activity. In certain embodiments, it will be preferred to use the full-length hexokinase IV sequence in creating a HK:GK chimera, as this will be one of the most straightforward approaches. In constructing a recombinant gene that encodes such a chimera or fusion protein, one may use a contiguous nucleic acid sequence from SEQ ID NO:19 or SEQ ID NO:21. A currently preferred example of such a gene construct is that which comprises the contiguous nucleic acid sequence of SEQ ID NO:8.

In addition to truncated hexokinases and hexokinase-glucokinase chimeras low $K_m$ hexokinases that have been subjected to mutagenesis to render them catalytically inactive may also be used in displacing endogenous hexokinase from the mitochondria. In this way, a substantially full-length low $K_m$ hexokinase enzyme may be used, so long as it does not exhibit any significant enzymatic activity. Hexokinase enzymes may be mutated both chemically and by using molecular biological techniques to introduce amino acid changes at specific points in the protein sequence.

The range of mammalian cells that may be used in connection with the present invention is virtually limitless. By way of example only, one may mention neuroendocrine cells and secretory cells, as exemplified in certain circumstances by insulinoma cells. Both glucose-responsive and non-glucose-responsive cells are also contemplated for use herewith.

In certain embodiments, the present invention provides engineered cells that secrete insulin in response to glucose, which cells comprise an inhibitor of a low $K_m$ hexokinase, the inhibitor selected from:

(a) an agent that stimulates the production of trehalose-6-phosphate;

(b) a low $K_m$ hexokinase-specific ribozyme; or (c) an agent that competitively reduces low $K_m$ hexokinase activity;

wherein said inhibitor is present in an amount effective to reduce the low $K_m$ hexokinase activity of said cell.

Such engineered cells will generally comprise at least one of a recombinant hexokinase IV gene, a recombinant insulin gene and/or a recombinant GLUT-2 gene. In preferred embodiments, where the cell comprises a hexokinase IV gene and/or a GLUT-2 gene, these genes will be an islet isoform of such genes. In general, it is preferred to introduce the recombinant gene into the cell by means of a recombinant vector.

Any cells in accordance with the present invention may be cells that further comprise a recombinant gene that expresses a selected protein. The foregoing insulin-secreting cells are just one example of this concept. Any one of an extremely large number of therapeutic proteins could be produced in such a recombinant host cell. All such cells fall within the scope of the present invention so long as they comprise an inhibitor of a low $K_m$ hexokinase.

As mentioned above, cells that are capable of forming secretory granules will be preferred in certain aspects of the invention. Such cells are exemplified by neuroendocrine cells, AtT-20 cells, GH-1 and GH-3 cells; pancreatic β cells such as βTC, HIT or RIN cells. Such cells may secrete recombinant insulin. The cells may also comprise a glutamic acid decarboxylase gene, which may be present in a recombinant form.

The TPS, ribozyme and hexokinase displacement agents described above may be combined in any given cell in order to effect even greater hexokinase inhibition. Any one or more of the foregoing methods may also be combined with other methods of inhibiting hexokinase. For example, combination of these methods along with the expression or over-expression of glucokinase is particularly contemplated.

It is also contemplated that any or all of the foregoing agents could be used in a cell in which a low $K_m$ hexokinase gene has been interrupted using knockout technology, such as homologous recombination or random integration. Combination of any of the foregoing agents along with an antisense RNA molecule that is complementary to, and that binds to, a low $K_m$ hexokinase gene or RNA transcript is also contemplated within the invention.

Any of the cells of the present invention may be formulated in pharmaceutically acceptable vehicles. They may also be encapsulated within biocompatible coatings and semi-permeable devices. The cells of the invention may also be contained within an animal or human subject.

The present invention further provides an engineered mammalian cell derived from a cell that forms secretory granules, the cell secreting insulin in response to glucose and comprising a first recombinant gene selected from the group consisting of hexokinase IV, insulin and GLUT-2 and a second recombinant gene selected from the group consisting of:

(a) a recombinant gene that expresses a protein that stimulates the production of trehalose-6-phosphate;

(b) a recombinant gene that expresses a low $K_m$ hexokinase-specific ribozyme; and (c) a recombinant gene that expresses an agent that competitively reduces low $K_m$ hexokinase activity.

Also included within the invention are methods for making engineered cells that have reduced low $K_m$ hexokinase activity. Such methods generally comprise contacting a cell with a composition comprising an inhibitory agent characterized as:

(a) an agent that stimulates the production of trehalose-6-phosphate;

(b) a low $K_m$ hexokinase-specific ribozyme; or (c) an agent that competitively reduces low $K_m$ hexokinase activity.

In general, the inhibitory agents will be introduced into the cell by means of a recombinant gene or vector that expresses the inhibitory agent. Preferred cells that can be generated in this manner include cells that comprise a recombinant gene that expresses a selected protein, such as insulin, and cells that further secrete the encoded protein.

Many methods of using the cells of the present invention are provided herein. A first method is that for providing glucose-responsive insulin secreting capacity to a mammal or human subject. This method generally comprises administering to the mammal or patient, an effective amount of a population of engineered cells that secrete insulin in response to glucose, the population comprising cells that have a reduced low $K_m$ hexokinase activity and which cells comprise:

(a) an agent that stimulates the production of trehalose-6-phosphate;

(b) a low $K_m$ hexokinase-specific ribozyme; or (c) an agent that competitively reduces low $K_m$ hexokinase activity.

The engineered cells will preferably be provided to the animal or patient in the form of a semipermeable device or following encapsulation in a biocompatible coating.

A further method is that for producing insulin, which method generally comprises the steps of:

(a) culturing an engineered cell that secretes insulin in response to glucose, the cell having a reduced low $K_m$ hexokinase activity and comprising:

(i) an agent that stimulates the production of trehalose-6-phosphate;

(ii) a low $K_m$ hexokinase-specific ribozyme; or (iii) an agent that competitively reduces low $K_m$ hexokinase activity; and (b) obtaining insulin from the cultured cell.

In addition to cells that contain an inhibitor of a low $K_m$ hexokinase, the present invention also provides compositions comprising the inhibitors themselves. Therefore, another aspect of the present invention is a composition comprising an inhibitor of a low $K_m$ hexokinase, characterized as:

(a) a recombinant vector comprising a promoter operably linked to a gene that encodes a protein that stimulates the production of trehalose-6-phosphate, the promoter expressing the protein in a mammalian cell;

(b) a low $K_m$ hexokinase-specific ribozyme or a recombinant gene or vector that expresses said ribozyme; or (c) an agent that competitively reduces low $K_m$ hexokinase activity or a recombinant gene or vector that expresses said agent.

In yet still further embodiments, the present invention provides advantageous methods for inhibiting the growth rate of a cell, whether in vitro or in vivo. To inhibit the growth rate of a cell in accordance with the aspects of the invention, one would simply reduce the low $K_m$ hexokinase activity in the cell, as exemplified by inhibiting hexokinase I and/or hexokinase II.

Any of the foregoing trehalose-6-phosphate generation, hexokinase-specific ribozymes and agents that competitively reduce low $K_m$ hexokinase activity, e.g., by displacing hexokinase from the mitochondria, may be used to inhibit low $K_m$ hexokinase with a view to inhibiting the growth rate of a cell.

In addition to the foregoing methods, any other methods known to those of skill in the art may also be employed in these aspects of the invention. By way of example only, one may mention methods to reduce hexokinase activity by interruption of a low $K_m$ hexokinase gene, as may be achieved by homologous recombination or random integration, and also, the use of antisense technology.

Regardless of the particular method or methods employed, it will generally be preferred to contact the target cell with a recombinant gene or vector that expresses the active inhibitory agent or construct. Providing to the cell a recombinant glucokinase enzyme in this manner is another method that is contemplated to be useful in the generation of a cell with a reduced growth rate.

As described earlier, the range of cells that may be manipulated in this manner to produce slower-growing cells is virtually inexhaustible. The cells may or may not comprise a recombinant gene that expresses a selected protein, and may or may not secrete a natural or recombinant protein product, either constitutively or in response to a specific signal or stimulatory agent.

Such growth rate-inhibited cells may be administered to an animal or human subject in order to provide to the animal or patient a selected protein or polypeptide. In such embodiments, one would administer to an animal or human an effective amount of a growth rate-inhibited cell or population of such cells, wherein the cell or cells express the selected protein that one wishes to deliver to the animal or human subject. Using cells with low $K_m$ hexokinase activity in this manner is contemplated to be advantageous in that the cells are likely to survive for longer periods within the host animal. Preferably, the growth rate-inhibited cells will be encapsulated in a biocompatible coating prior to administration to the animal or human subject.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Hexokinase ribozyme transgene expression in RIN cells. Northern analysis of RNA isolated from RNA isolated from two independent G418 resistant transfected with pCMV8/HKRIBO1+2/IRES/NEO (EP113/1A and B). A probe specific for the neomycin resistance gene detects the HKribozyme/IRES/Neo message at the expected molecular weight of 1100 base pairs in both polyclones with no detectable signal in the parental RIN 1046-38.

DETAILED DESCRIPTION OF THE PREFERRED EMBODIMENTS

Figure 1:
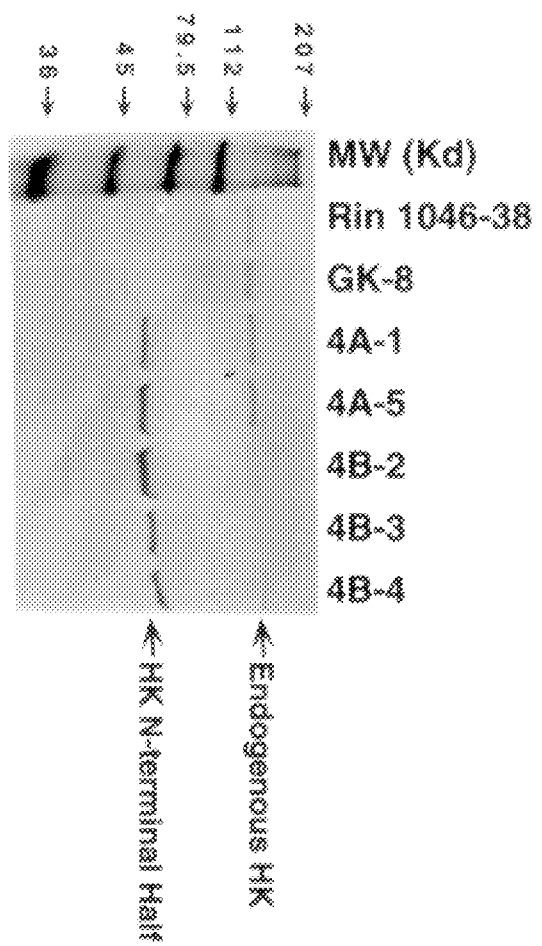
FIG. 1. Western analysis of Hexokinase N-terminal half expression in RIN 1046-38 cells. Whole cell lysates were resolved by SDS-PAGE and immunoreactive proteins were detected using a rat hexokinase I specific antibody. Lysates prepared from parental RIN 1046-38 and GK-8 cells (a RIN clone overexpressing rat glucokinase) are in lanes 1 and 2 as controls. Endogenous hexokinase I runs with an apparent molecular weight of greater than 100 kD on this gel system. Lysates from five monoclonal RIN lines expressing the hexokinase N-terminal half are in lanes 3 through 7.

The present invention relates to several compositions and methods for reducing the activity of a particular class of enzymes, known as hexokinases, in mammalian cells. Three general groups of compositions and methods for achieving this end are described. These methods may, of course, be combined with other methods of hexokinase inhibition, such as expression of glucokinase, and with other cellular engineering methods.

The invention relates first to compositions and methods for displacing cellular hexokinases from their mitochondrial binding site or sites. As mitochondrial binding enhances the activity of hexokinases, displacement is an effective method of inhibition. In certain aspects, an inactive hexokinase variant or fragment that still binds to mitochondria is supplied to a cell. In other aspects, the inactive hexokinase or hexokinase fragment is fused to an active glucokinase or portion thereof, resulting in a displacement-replacement method. In this embodiment, the chimeric enzyme not only displaces cellular hexokinases from their mitochondrial site, thus inhibiting hexokinase, but also provides to the cell additional copies of the glucokinase enzyme that operates in glucose sensing. It is preferred that the engineered hexokinase or hexokinase-glucokinase chimera be provided to the cell by means of a eukaryotic expression vector that is introduced into the cell and that directs expression of the desired protein.

Next, the present invention concerns compositions and methods for stimulating the production of the compound trehalose-6-phosphate in a mammalian cell. The yeast enzyme trehalose-6-phosphate synthase (TPS1) is currently the preferred agent for use in generating trehalose-6-phosphate, which is a metabolic inhibitor of hexokinase activity. Engineering of the yeast gene encoding TPS1 into a eukaryotic expression vector and introduction of the vector into a mammalian cell is generally the preferred method of producing the trehalose-6-phosphate inhibitor.

The third general aspect of the invention relates to compositions and methods for inhibiting hexokinase at the messenger RNA (mRNA) level. In these aspects, the invention provides hexokinase-specific ribozymes that destroy hexokinase mRNA species. These are fragments of ribonucleic acid that comprise a sequence complementary to a specific portion of one or more hexokinase mRNAs and that also contain a second segment of ribonucleic acid with RNA degradative catalytic activity ("catalytic ribozyme"). Again, it is preferred to engineer the hexokinase-specific ribozyme into a eukaryotic expression vector and to introduce the vector into a mammalian cell, where it directs the destruction of hexokinase mRNA and reduces expression of the hexokinase enzyme.

Any of the three aspects of the invention may be combined together and/or with other methods for inhibiting hexokinase. One such method is that for stimulating the production of the compound glucose-6-phosphate in a mammalian cell. The enzyme glucokinase, the high $K_m$ member of the hexokinase gene family, is currently the preferred agent for use in generating glucose-6-phosphate, which is a metabolic inhibitor of low $K_m$ hexokinases that are inhibited as disclosed herein. Engineering of a mammalian glucokinase cDNA or gene into a eucaryotic expression vector and introduction of the vector into a mammalian cell is generally the preferred method of producing the glucose-6-phosphate inhibitor.

A. Hexokinases

Glucose enters mammalian cells through glucose transport proteins. Following entry into the cell, the first step of glucose metabolism is its phosphorylation to glucose-6-phosphate, which is catalyzed by one of a family of hexokinase enzymes. There are four known members of the family, termed hexokinases I, II, III, and IV (HKI, HKII, HKIII and HKIV; Wilson, 1985), which are encoded by separate genes (Schwab and Wilson, 1989; 1991; Thelan and Wilson, 1991). Hexokinases I, II, and III have similar kinetic and structural properties, while hexokinase IV, also known as glucokinase (GK), is less related. Hexokinases I, II, and III are generally termed "low $K_m$" hexokinases because they have a $K_m$ for glucose in the range of 10–50 μM, compared to approximately 6–8 mM for glucokinase (Wilson, 1985).

The low $K_m$ hexokinases have a molecular mass of approximately 100,000 daltons. Gene cloning and amino acid sequence analysis has revealed that the low $K_m$ hexokinases are comprised of two halves of homologous sequence. Glucokinase lacks this internal repeat, and is thus only half as large as the low $K_m$ enzymes. The two halves of the low $K_m$ hexokinases are commonly described as the C-terminal "catalytic" domain and the N-terminal "regulatory" domain. The C-terminal domain retains full catalytic activity when expressed independently of the N-terminal domain and also exhibits allosteric inhibition by glucose-6-phosphate. It is believed that the glucose-6-phosphate allosteric site of the C-terminal domain is latent in the intact enzyme, and that allosteric regulation of the intact enzyme is conferred by the glucose-6-phosphate binding site of the N-terminal "regulatory" domain (Wilson, 1994).

Different members of the hexokinase gene family tend to be expressed in different mammalian tissues. Thus, hexokinase I is expressed in brain, red blood cells, and many other tissues, hexokinase II is expressed mainly in muscle and fat, hexokinase III is expressed in lung, and glucokinase is expressed primarily in liver and pancreatic islet β cells. Transformed cell lines, such as those contemplated by the inventors for use in insulin replacement in diabetes generally express high levels of hexokinase I and II, irrespective of the hexokinase isoforms expressed in their primary tissue of origin (Mathupala et al., 1995). For example, insulinoma cell lines derived from islet β cells often contain 4–6 times more low $K_m$ hexokinase enzymatic activity than normal islet β cells (Ferber et al., 1994; Efrat et al., 1993) and studies performed by inventors on one such cell line, RIN1046-38, reveals that the low $K_m$ hexokinase activity is contributed by expression of both hexokinases I and II, with no detectable expression of hexokinase III. Thus, the methods described in this application are generally focused upon inhibition of the activities of hexokinases I and II, as these are the major low $K_m$ isoforms found in cell lines.

All four isoforms of rat hexokinase (I through III, and IV being glucokinase) have been cloned. The nucleic acid and amino acid sequences of each are included herein as SEQ ID NO:13 through SEQ ID NO:22. Referring to the nucleic acid sequence first, these are HKI, SEQ ID NO:13 and SEQ ID NO:14; HKII, SEQ ID NO:15 and SEQ ID NO:16; HKIII, SEQ ID NO:17 and SEQ ID NO:18; rat islet GK, SEQ ID NO:19 and SEQ ID NO:20; and rat liver GK, SEQ ID NO:21 and SEQ ID NO:22.

Hexokinase isoforms have also been cloned from many other species that are known to have similar properties to the rat hexokinases referenced above. These include human isoforms of HKI(GenBank Accession # M75126 and X69160), HK II (# Z46376), HK III (# U42303) and GK (# M88011, # M69051, and # M90299), yeast *S. cerevisiae* HKs (# M14410, M11184 and M11181) and GK (# M24077), mouse HK (# J05277) and GK (# L38990), bovine HK (# M65140), Plasmodium HK (# M92054) and *E. coli* GK (# U22490). It is contemplated that the foregoing HK and GK sequence information could be employed in designing and creating inhibitory constructs for use as disclosed herein, although the use of the rat HK and GK sequence information is currently preferred.

B. Mitochondrial Binding

Low $K_m$ hexokinases are distinguished from glucokinase in that they are allosterically regulated by glucose-6-phosphate and by binding to mitochondria (Wilson, 1968; 1973; 1985; 1995). Micromolar concentrations of glucose-6-phosphate inhibit the activities of hexokinases I, II, and III, but appreciable inhibition of glucokinase requires glucose-6-phosphate concentrations in excess of 10 mM. Binding of hexokinases I and II to mitochondria alters their kinetic properties (Wilson, 1968; 1985; 1995), while glucokinase does not appear to be capable of binding to mitochondria at all (Becker et al. 1996).

When bound to mitochondria, hexokinase I undergoes an increase in affinity (a decrease in $K_m$) for its substrate ATP (Wilson, 1985). In addition, the enzyme becomes far less inhibitable by glucose-6-phosphate, as indicated by a several-fold increase in $K_i$ for this ligand (Wilson, 1985). Studies with hexokinase I have revealed the existence of two types of mitochondrial binding sites (Kabeer and Wilson, 1994). Glucose-6-phosphate causes displacement of a proportion of mitochondrially-bound hexokinase from one type of site. The enzyme that remains bound to mitochondria after glucose-6-phosphate treatment is considered to occupy the second site, from which it can be removed by treatment with 0.5M KSCN.

It has been known for some time that limited digestion of hexokinase I with chymotrypsin yields an enzyme fragment that retains catalytic activity but that loses its capacity for mitochondrial binding, and that enzyme treated in this manner is lacking in a portion of its N-terminal domain (Polakis and Wilson, 1985). The N-terminal sequences of both hexokinases I and II are relatively hydrophobic, and it has been shown that the hydrophobic N-terminus of hexokinase I is capable of insertion into the lipid bilayer of the mitochondrial membrane (Xie and Wilson, 1988).

Subsequently, Gelb et al., (1992) demonstrated that a chimeric protein consisting of the N-terminal 15 amino acids of hexokinase I fused to chloramphenicol acetyltransferase was capable of binding to rat liver mitochondria, and that this binding was competitive with authentic hexokinase I (Gelb et al. 1992). Although Gelb et al. (1992) have suggested that the first 15 amino acids of hexokinase are sufficient to target such a chimeric protein to mitochondria, these studies were not designed to attempt to alter metabolic regulation in target cell lines. Thus, the elements required to effect displacement of endogenous hexokinase from its mitochondrial binding site were not unequivocally identified in the study of Gelb and co-authors as discussed below.

While the results of Gelb et al. (1992) argue for the importance of this small N-terminal segment in targeting of hexokinase to mitochondria, others have suggested that other regions of the molecule may also be important in stabilizing the interaction (Polakis and Wilson, 1985; Felgner and Wilson, 1977; Smith and Wilson, 1991). This is based on studies showing that hexokinase I binding to mitochondria is stabilized by $Mg^{2+}$, an effect likely reflecting electrostatic interactions between the enzyme and the outer mitochondrial membrane (i.e., not involving the N-terminal 15 amino acids that are intercalated into the membrane). Therefore, the mitochondrial binding regions of HK have not been clearly identified to date, and there is even less information available on the issue of HK displacement.

At least part of hexokinase binding to mitochondria is via interactions with members of a family of proteins known as voltage-dependent anion channels (VDAC) or porins (Fiek et al., 1982; Linden et al., 1982). These porins form a channel through which metabolites such as ATP and various anions traverse the outer mitochondrial membrane. Binding of hexokinases to porin thus may ensure a supply of intramitochondrially-generated ATP as substrate.

Constructs of the present invention may comprise the N-terminal 15 amino acids of a hexokinase enzyme, preferably hexokinase I or II, since this segment should be easily expressed in cells and retained as a stable peptide. Constructs comprising the entire N-terminal domain of either hexokinase I or hexokinase II, or the intact, full-length hexokinase I or II proteins that have been rendered inactive by site-directed mutagenesis of amino acids that are important for the enzyme's catalytic function are also contemplated. Constructs based upon hexokinase I will be particularly, or even exclusively, preferred in certain embodiments.

The reason for preferring the N-terminal domain construct is that this element seems to comprise a complete structural domain, based upon studies in which this domain can be expressed in bacteria and shown to bind glucose-6-phosphate (Wilson, 1994; Arora et al., 1993; White and Wilson, 1987; White and Wilson, 1990). This suggests that the intact N-terminal domain should fold and form a structure analogous to its structure in the full-length hexokinase I or II protein. As the present inventors contemplate that this structure mediates attachment of the intact hexokinase protein to mitochondria, the intact, correctly folded N-terminal domain is a preferred embodiment of this invention.

For embodiments involving the N-terminal domain, a segment comprising amino acids 1–455 is preferred because of a naturally occurring NcoI restriction enzyme site in the DNA sequence corresponding to amino acid 482. This NcoI site allows the fragment encoding the N-terminal domain to be easily isolated and subcloned, and also allows direct fusion of the N-terminal domain of hexokinase to the intact functional sequence of glucokinase via an NcoI site located at the AUG start codon of this gene.

Of course, it will be understood that peptides, polypeptides and protein domains of any intermediate length between about 15 amino acids and about 455 amino acids, and longer proteins, may be used in displacing endogenous hexokinase from the mitochondria. Accordingly, constructs comprising about 20, about 50, about 100, about 150, about 200, about 300 or about 400 amino acids in length may be used for these purposes. It is also contemplated that an intact hexokinase protein that is rendered catalytically inactive will interact with mitochondria in a manner identical to the active proteins. Expression of such a HK variant is therefore another method for inhibiting endogenous HK (Baijal and Wilson, 1992). Inactivated hexokinase proteins include those that have been subjected to chemical mutagenesis and also those produced using molecular biological techniques and recombinant protein production.

The identification of appropriate polypeptide regions and/or particular amino acid sites that may be targeted in order to inactivate hexokinase will be known to those of skill in the art. The crystal structure of certain hexokinase enzymes is available. Coupling the crystal structure information with a comparison of the primary sequence information for various distinct hexokinases will allow one to identify those regions and sites that are important for hexokinase activity, such as the binding sites for ATP, glucose and glucose-6-phosphate. This has been discussed in detail in various publications, such as Printz et al. (1993), incorporated herein by reference, which information can be used in connection with preparing mutants and variants for use herewith. Deletion of certain amino acids or peptide segments, as may be achieved by molecular biological manipulation, is another contemplated method for preparing inactive hexokinases.

The enzyme glycerol kinase is another protein thought to bind to mitochondria via porins or VDACs (Adams et al., 1991). Glycerol kinase catalyzes formation of glycerol phosphate from glycerol, using ATP as phosphate donor. Thus, expression of glycerol kinase in cell lines represents an alternative to expression of inactive hexokinase proteins or fragments thereof which is also contemplated for use in the displacement of endogenous low-$K_m$ hexokinases from their normal mitochondrial binding site.

A particularly powerful method of inhibiting hexokinase within a mammalian cell involves the displacement of hexokinase from the mitochondria and the concomitant provision of inactive glucokinase. This is advantageously achieved by providing to the cell a hexokinase-glucokinase chimera or fusion protein, in which the hexokinase portion is capable of binding to the mitochondria and yet does not exhibit hexokinase catalytic activity, and in which the glucokinase portion is catalytically active. Chemically-fused polypeptides are a possibility, but recombinant proteins are naturally most preferred for use in this manner. The identification of appropriate hexokinase fragments for use in such a chimera has been described herein above.

In terms of the glucokinase portions of these fusion proteins, any glucokinase-derived sequence that contains enough primary sequence information to confer glucokinase catalytic activity to the chimera will be useful in this context. However, it will often be preferred to use the entire glucokinase enzyme as this is more straightforward in terms of methodology. Again, one may look to the extensive information available in various published references in order to assist with the identification of appropriate glucokinase enzymes or fragments thereof.

At this point, a discussion of the kinetic properties of hexokinase and glucokinase is relevant. It will be understood that in providing a functional equivalent of a hexokinase or glucokinase enzyme, one would desire to provide a protein that has substantially the same kinetic parameters as the native enzyme. Equally, in providing a hexokinase mutant that is devoid of catalytic activity, one would provide an enzyme that is either completely inactivated or whose kinetic parameters have been shifted so that it is, in fact, distinct from the native enzyme.

Table 1, below, sets forth a comparison of glucokinase with hexokinases I–III. This information may be used in order to determine whether any particular variant is "equivalent", and also, to confirm that any inactive mutants have indeed been properly disabled.

TABLE 1

A Comparison of Glucokinase With Hexokinases

|  | GK | HKI–III |
|---|---|---|
| Km glucose | 5–12 mM | 0.02–0.13 mM |
| Km ATP | 0.5 mM | 0.2–0.5 mM |
| Ki G-6-P | 60 mM | 0.2–0.9 mM |
| Molecular weight | 52 kd | ~100 kd |

TABLE 1-continued

A Comparison of Glucokinase With Hexokinases

|  | GK | HKI–III |
|---|---|---|
| Substrate preference | | |
| Glucose | 1 | 1 |
| Mannose | 0.8 | 1–1.2 |
| 2-Deoxyglucose | 0.4 | 1–1.4 |
| Fructose | 0.2 | 1.1–1.3 |

The activity of glucose as a substrate is taken as 1. The other numbers are expressed in relation to the activity of glucose as a substrate.

C. Trehalose-6-Phosphate Metabolism

In Bakers yeast, glucose phosphorylation is also catalyzed by a family of hexokinases that are related in sequence and function to the mammalian hexokinase gene family. Yeast cells, however, contain other genes involved in carbohydrate metabolism for which there are no mammalian counterparts. The trehalose-6-phosphate synthase/trehalose-6-phosphate phosphatase complex is an example of such an activity.

The trehalose-6-phosphate synthase/phosphatase complex catalyzes the formation of trehalose, a disaccharide of two glucose molecules (α-D-glucopyranosyl (1-1) α-D-glucopyranoside) by first forming trehalose-6-phosphate by condensation of two molecules of glucose-6-phosphate and then using its phosphatase activity to remove the phosphate groups to generate free trehalose (Bell et al., 1992). Trehalose is thought to represent a form of storage polysaccharide in yeast, bacteria and other lower organisms, but neither the trehalose-6-phosphate synthase enzyme complex nor its products trehalose-6-phosphate or free trehalose are known to be present in mammalian cells.

Blazquez et al. have demonstrated that trehalose-6-phosphate can inhibit the activity of hexokinases from a variety of different organisms, including rat brain, which expresses predominantly hexokinase I (Blasquez et al., 1993). This has led to the suggestion that trehalose-6-phosphate may be an important regulator of glycolytic flux in yeast cells. Consistent with this notion, the yeast gene known as cif-1 was originally cloned from yeast that are unable to grow in glucose (Blasquez et al., 1993) and subsequently shown to be identical to the smallest subunit (56 kD) of the trehalose phosphate synthase/trehalose-6-phosphate phosphatase complex (Bell et al., 1992). Cells lacking in the CIF-1 gene product exhibit rapid depletion of ATP, presumably because they are unable to produce trehalose-6-phosphate that normally serves to moderate yeast hexokinase activity. It is believed that the 56 kDa CIF-1 gene product encodes the trehalose phosphate synthase activity (Bell et al., 1992).

One of the three general methods described in this application for inhibiting low $K_m$ hexokinase activity in mammalian cells is to express an enzyme, such as yeast trehalose-6-phosphate synthase, that will allow trehalose-6-phosphate to accumulate. This will have two effects. First, the accumulated trehalose-6-phosphate will serve to allosterically inhibit endogenous low $K_m$ hexokinase activity. Second, where trehalose-phosphate synthase is used, this enzyme will divert glucose-6-phosphate into trehalose-6-phosphate at low, non-stimulatory glucose concentrations where low $K_m$ hexokinases but not glucokinases are active, thereby "short-circuiting" metabolic signalling for insulin secretion, which is thought to require ATP produced via further glucose metabolism (Newgard and McGarry, 1995).

A currently preferred gene for use in these aspects is the S. cerevisiae gene encoding trehalose-6-phosphate synthase (TPS1) (nucleic acid, SEQ ID NO:1; and encoded amino acid, SEQ ID NO:2). Genes from several other organisms encoding treholose-6-phosphate synthase have been isolated and the amino acid sequences deduced. These include E. coli (GenBank Accession # X69160), S. pombe (# Z29971), Mycobacterium laprae (# U15187) and Aspergillus niger (# U07184). It is contemplated that any of the foregoing or other biological functional equivalents thereof may be used in the context of the present invention.

D. Hexokinase Inhibition at Nucleic Acid Level

Several different ribozyme motifs have been described with RNA cleavage activity (reviewed in Symons, 1992). Examples that would be expected to function equivalently for the down regulation of low $K_m$ hexokinases include sequences from the Group I self splicing introns including Tobaco Ringspot Virus (Prody et al., 1986), Advocado Sunblotch Viroid (Palukaitis et al., 1979 and Symons, 1981), and Lucerne Transient Streak Virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al, 1992, Yuan and Altman, 1994), hairpin ribozyme structures (Berzal-Herranz et al, 1992 and Chowrira et al., 1993) and Hepatitis Delta virus based ribozymes (Perrotta and Been, 1990). The general design and optimization of ribozyme directed RNA cleavage activity has been discussed in detail (Haseloff and Gerlach, 1988, Symons, 1992, Chowrira, et al., 1994, and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes the cleavage site is a dinucleotide sequence on the target RNA, is a uracil (U) followed by either an adenine, cytosine or uracil (A,C or U) (Perriman, et al., 1992 and Thompson, et al., 1995). The frequency of this dinucleotide occurring in any given RNA is statistically 3 out of 16. Therefore, for a given target messenger RNA of 1000 bases, 187 dinucleotide cleavage sites are statistically possible. The message for low $K_m$ hexokinases targeted here are greater than 3500 bases long, with greater than 500 possible cleavage sites.

The large number of possible cleavage sites in the low $K_m$ hexokinases coupled with the growing number of sequences with demonstrated catalytic RNA cleavage activity indicates that a large number of ribozymes that have the potential to downregulate the low $K_m$ hexokinases are available. Designing and testing ribozymes for efficient cleavage of a target RNA is a process well known to those skilled in the art. Examples of scientific methods for designing and testing ribozymes are described by (Chowrira, et al., (1994) and Lieber and Strauss (1995), each incorporated by reference. Therefore, it will be understood that the sequences of SEQ ID NO:3, SEQ ID NO:4 and SEQ ID NO:5 are exemplary and by no means limiting. The identification of operative and preferred sequences for use in hexokinase-targeted ribozymes is simply a matter of preparing and testing a given sequence, and is a routinely practiced "screening" method known to those of skill in the art.

E. Combination of Inhibitory Methods

Any of the three general methods of HK inhibition described above (Mitochondrial HK displacement, trehalose-6-phosphate generation and anti-HK ribozymes) may be combined with one another and/or with other engineering methods. It is particularly contemplated that these methods could be used in combination with glucokinase overproduction. Glucokinase overproduction alone is even thought to be a useful method of inhibiting hexokinase, as set forth below.

Low $K_m$ hexokinases, including hexokinases I and II that are present at high levels in mammalian cell lines, are inhibited by glucose-6-phosphate. Thus, this invention also relates to methods for maintaining glucose-6-phosphate at high levels in cell lines. The preferred method for achieving consistently high levels of glucose-6-phosphate in cells is to overexpress glucokinase in such lines.

Expression of glucokinase is considered advantageous for two distinct reasons. First, as described in U.S. Pat. No. 5,427,940 expression of glucokinase is part of an advantageous method for engineering of glucose-stimulated insulin secretion in cell lines. Glucokinase expression is herein shown to have the added benefit of maintaining high levels of glucose-6-phosphate to keep low $K_m$ hexokinases in an inhibited state. This advantage would become particularly relevant at glucose concentrations in the physiological range (4–9 mM), because glucokinase is active at these levels. Also, while glucokinase is a member of the hexokinase gene family, it is not itself inhibited by glucose-6-phosphate.

F. Advantages of Hexokinase Inhibition in Mammalian Cells

The various aspects of this invention focus specifically on reducing the levels of low $K_m$ hexokinase activity in mammalian cells. A particular type of target cell is a neuroendocrine cell. There are at least two significant achievements accomplished by the hexokinase inhibition of the present invention, as set forth below.

1. Reduced Growth Rate

In addition to the regulation of insulin secretion by glucose, the hexokinase gene family may also be important in the regulation of cell growth and proliferation. As described above, increases in low $K_m$ hexokinase activity usually correlate with the transformation of cells from a normal to cancerous phenotype. However, the correlation has not been proven to exist as a cause and effect relationship. In addition, increases in mitotic activity are not universally linked to induction of low $K_m$ hexokinases. The activity of these enzymes did not increase in preneoplastic mouse beta cell lines over-expressing simian virus 40 large T antigen (Tag)(Radvanyi et al., 1993); nor are they universally elevated in fully transformed mouse β cells (Efrat et al., 1993).

The reduction of hexokinase activity in a cell line by any suitable method, including any of the novel methods disclosed herein, is contemplated to be of use in inhibiting cell growth. Hexokinase I was discovered to be a regulator of cell growth during the inventors' studies in which a RIN cell line (86/X4) that contains a disrupted allele of the HKI gene was surprisingly found to grow about one-half as fast as clones containing the normal compliment of two HKI wild-type genes.

A relationship between low $K_m$ hexokinase activity and cellular growth rates has three important implications relative to the application of cell-based therapies. First, from the perspective of iterative genetic engineering, an untimely or unregulated decrease of hexokinase activity will potentially hinder the growth and selection of clones possessing desired genotypes and traits. A cell line that over-expresses hexokinase I from a regulatable promoter may provide the optimal genetic background for engineering of gene targets. For example, a RIN cell line could be developed that transgenically expresses hexokinase under the control of the tetracycline (Tet)-resistance operon regulator system (Gossen and Bujard 1992). This expression system allows powerful transcription of gene products and permits the ablation of gene expression in the presence of Tet and Tet derivatives. Efrat et al. (1995) have demonstrated the feasibility of using this expression system to regulate large Tag gene expression. The expression of Tag caused transformation and expansion of mouse beta cells. A decrease of Tag expression, by the in vitro or in vivo administration of Tet, led to an inhibition of cellular proliferation.

A RIN or neuroendocrine cell line that expresses HKI from a repressible promoter could be further engineered to express high levels of human insulin, glucokinase, and GLUT-2. In addition, such a cell line would be an ideal host for the ablation or down regulation of low $K_m$ hexokinases. Such engineering could be pursued without the hindering complication of slowed growth. Following a series of desired genetic manipulations, the growth of the cells and the glucose sensing ability could be modulated by down regulating hexokinase expression.

A second implication of low $K_m$ hexokinase as a regulator of cellular growth concerns the use of engineered cells for in vivo therapies. It is envisioned that cell-based delivery will be conducted by maintenance of the cells in vivo in a perm-selective device. It is contemplated that cells with reduced levels of low $K_m$ hexokinase activity will survive for longer periods of time in devices or capsules as a consequence of their reduced growth rates.

A third implication of low $K_m$ hexokinases as regulators of cellular growth involves the creation of novel β cell lines. The over-expression of HKI by introduction of exogenous DNA into a primary beta cell could be an essential ingredient of the transformation process. NIH-3T3 cells, an immortalized cell line, showed increases in glycolysis and growth rates following transfection with low $K_m$ hexokinase (Fanciulli et al., 1994). In a preferred embodiment, hexokinase I would need to be under the control of a promoter that can be down regulated. Such transcriptional regulation would allow the subsequent modulation of growth and glucose sensing.

2. Glucose-Regulatable Protein Secretion

A second important reason for reducing hexokinase activity is that it will contribute to the development of engineered cells that exhibit glucose-regulatable protein secretion, the most important aspect of which is presently the physiologically regulated release of insulin. Insulin release from the β-cells of the islets of Langerhans in the pancreas is prominently regulated by the circulating glucose concentration. Glucose stimulates insulin release over the physiological range of glucose concentrations (approximately 4–9 mM), with the amount of insulin secreted being proportional to the rate of glucose metabolism (Newgard and McGarry, 1995).

Glucose phosphorylation appears to play an important role in regulating glucose metabolism and insulin responsiveness (Meglasson and Matschinsky, 1986). Thus, while islet extracts contain approximately equal amounts of high $K_m$ glucokinase and low $K_m$ hexokinase activities (Meglasson and Matchinsky, 1986; Hughes et al., 1992), the hexokinases appear to be inhibited in intact islets, presumably by glucose-6-phosphate, allowing the glucokinase activity to be predominant. Since glucokinase has a $K_m$ for glucose (approximately 6–8 mM) that is within the physiological range, it is ideally suited for regulating glycolytic flux and insulin release in proportion to the extracellular glucose concentration.

The concept of a regulatory role for glucokinase, which has been developed over several years (Meglasson and Matschinsky, 1986; Matschinsky, 1990), is supported by recent genetic and molecular studies, in which reduced expression of glucokinase was shown to result in less robust glucose-stimulated insulin secretion (Froguel et al., 1993; Efrat et al., 1994). Islet β-cells are also equipped with a specialized glucose transporter, GLUT-2, which like glucokinase is the high $K_m$ member of its gene family.

One of the present inventors has shown that GLUT-2 and glucokinase work in tandem as the "glucose sensing apparatus" of the β-cell (U.S. Pat. No. 5,427,940; Newgard et al., 1990). U.S. Pat. No. 5,427,940, incorporated herein by reference, describes methods for conferring glucose sensing in neuroendocrine cells and cell lines by transfection of such cells with one or more genes selected from the insulin gene, the glucokinase gene and the GLUT-2 glucose transporter gene, so as to provide an engineered cell having all three of these genes.

The overexpression of low $K_m$ hexokinases is known to exert a dominant effect on the glucose concentration threshold for insulin secretion. Overexpression of a low $K_m$ hexokinase from yeast in islet β-cells of transgenic animals results in increased rates of low $K_m$ glucose metabolism and enhanced insulin release at subphysiological glucose concentrations (Epstein et al., 1992; Voss-McGowan et al., 1994). Similar changes were noted upon overexpression of hexokinase I in isolated rat islets (Becker et al., 1994a) or in a well-differentiated insulinoma cell line called MIN-6 (Ishihara et al., 1994).

It has been shown that the neuroendocrine cell lines that are contemplated for use in engineering artificial β cells generally have significantly higher low $K_m$ hexokinase activity than normal islet β-cells (Hughes et al., 1992; Efrat et al., 1993; Hughes et.al., 1993; Ferber et al., 1994; Knaack et al., 1994), and that glucose metabolism in such cells is highly active at low glucose concentrations. As the glucokinase:hexokinase activity ratio is a critical determinant of the glucose response threshold in insulin secreting neuroendocrine cells, and as an imbalance in favor of hexokinase can cause insulin secretion to occur at glucose concentrations that are below the physiological threshold, it is evident that the most preferred artificial β cells should be further engineered to reduce hexokinase activity. The application of the methods of the present invention to the development of improved insulin secreting cells thus represents a significant advance.

G. Inhibition Levels

As defined herein, the degree of inhibition of hexokinase that is preferred is that necessary to achieve a glucose responsive insulin secretion in the physiologic range of 1.0 to 20 mM glucose. It will be understood by those working in this field that the absolute level of inhibition is difficult to predict. Measurements of hexokinase and glucokinase in freshly isolated islets as well as cell lines varies dramatically. Ratios of HK to GK can vary from 2.8 (Burch et al., 1981) to 0.8 (Liang et al., 1990) to 0.5 (Hosokawa et al., 1995) in fresh islets all with "normal" glucose stimulated insulin secretion. Reports of cell lines with "normal" secretion show an HK to GK ratio of 0.6 (Efrat et al., 1993), in the range of the fresh islets. These discrepancies illustrate the difficulties in specifying absolute numbers of glucokinase and hexokinase activities, hence the preference for using glucose responsive insulin secretion ranges as a meaningful parameter in characterizing the cells of the invention.

The present discoveries may be utilized in conjunction with certain further techniques, as described in the following sections, or as known to those of skill in the art.

1. Host Cells

Using the present invention may be combined with engineering of secretory cells to synthesize proteins for either in vitro large scale production, or for in vivo cell-based delivery. Regulated secretory cells present a natural bioreactor containing specialized enzymes involved in the processing and maturation of secreted proteins. These processing enzymes include endoproteases (Steiner et al., 1992) and carboxypeptidases (Fricker, 1998) for the cleavage of prohormones to hormones and PAM, an enzyme catalyzing the amidation of a number of peptide hormones (Eipper et al., 1992a). Similarly, maturation and folding of peptide hormones is performed in a controlled, stepwise manner with defined parameters including pH, calcium and redox states.

Complete processing requires sufficient levels of the processing enzymes as well as sufficient retention of the maturing peptides. In this way, physiological signals leading to the release of the contents of the secretory granules ensures release of fully processed, active proteins. This is important for both maximum production for in vitro purposes and for the possible use of cells for in vivo purposes.

All cells secrete proteins through a constitutive, non-regulated secretory pathway. A subset of cells are able to secrete proteins through a specialized regulated secretory pathway. Proteins destined for secretion by either mechanism are targeted to the endoplasmic reticulum and pass through the golgi apparatus. Constitutively secreted proteins pass directly from the golgi to the plasma membrane in vesicles, fusing and releasing the contents constitutively without the need for external stimuli. In cells with a regulated pathway, proteins leave the golgi and concentrate in storage vesicles or secretory granules. Release of the proteins from secretory granules is regulated, requiring an external stimuli. This external stimuli, defined as a secretagogue, can vary depending on cell type, optimal concentration of secretagogue, and dynamics of secretion. Proteins can be stored in secretory granules in their final processed form for long periods of time. In this way a large intracellular pool of mature secretory product exists which can be released quickly upon secretagogue stimulation.

A cell specialized for secreting proteins via a regulated pathway can also secrete proteins via the constitutive secretory pathway. Many cell types secrete proteins by the constitutive pathway with little or no secretion through a regulated pathway. As used herein, "secretory cell" defines cells specialized for regulated secretion, and excludes cells that are not specialized for regulated secretion. The regulated secretory pathway is found in secretory cell types such as endocrine, exocrine, neuronal, some gastrointestinal tract cells and other cells of the diffuse endocrine system.

(a) Glucose Responsive Cells.

For delivery of some peptide hormones or factors, it may be desirable to cause the polypeptide to be released from cells in response to changes in the circulating glucose concentration. A well-known example of a secretory cell type that is regulated in this fashion is the β-cell of the pancreatic islets of Langerhans, which releases insulin in response to changes in the blood glucose concentration.

Engineering of primary β-cells for production of products other than insulin is not particularly practical. Instead, a preferred vehicle may be one of the several cell lines derived from islet β-cells that have emerged over the past two decades. While early lines were derived from radiation or virus-induced tumors (Gazdar et al., 1980, Santerre et al., 1981), more recent work has centered on the application of transgenic technology (Efrat et al., 1988, Miyazaki et al., 1990). A general approach taken with the latter technique is to express an oncogene, most often SV40 T-antigen, under control of the insulin promoter in transgenic animals, thereby generating β-cell tumors that can be used for propagating insulinoma cell lines (Efrat et al., 1988, Miyazaki et al., 1990).

While insulinoma lines provide an advantage in that they can be grown in essentially unlimited quantity at relatively low cost, most exhibit differences in their glucose-stimulated insulin secretory response relative to normal islets. These differences can be quite profound, such as in the case of RINm5F cells, which were derived from a radiation-induced insulinoma and which in their current form are completely lacking in any acute glucose-stimulated insulin secretion response (Halban et al., 1983, Shimuzu et al., 1988). RIN1046-38 cells are also derived from a radiation-induced insulinoma but can be shown to be glucose responsive when studied at low passage numbers (Clark et al., 1990). This response is maximal at subphysiological glucose concentrations and is lost entirely when these cells are cultured for more than 40 passages (Clark et al., 1990).

GLUT-2 and glucokinase are expressed in low passage RIN 1046-38 cells but are gradually diminished with time in culture in synchrony with the loss of glucose-stimulated insulin release (Ferber et al., 1994). Restoration of GLUT-2 and glucokinase expression in RIN1046-38 cells by stable transfection restores glucose-stimulated insulin secretion (Ferber et al., 1994), and the use of these genes as a general tool for engineering of glucose sensing has been described in a previously issued patent (Newgard, U.S. Pat. No. 5,427,940). RIN 1046-38 cells transfected with the GLUT-2 gene alone are maximally glucose responsive at low concentrations of the sugar (approximately 50 $\mu$M), but the threshold for response can be shifted by preincubating the cells with 2-deoxyglucose, which when converted to 2-deoxyglucose-6-phosphate inside the cell serves as an inhibitor of low $K_m$ hexokinase, but not glucose activity (Ferber et al., 1994).

Recently, Asafari et al. have reported on the isolation of a new insulinoma cell line called INS-1 that retains many of the characteristics of the differentiated β-cell, most notably a relatively high insulin content and a glucose-stimulated insulin secretion response that occurs over the physiological range (Asafari et al., 1992). This line was isolated by propagating cells freshly dispersed from an X-ray induced insulinoma tumor in media containing 2-mercaptoethanol. Consistent with the finding of physiological glucose responsiveness, a recent report indicates that INS-1 cells express GLUT-2 and glucokinase as their predominant glucose transporter and glucose phosphorylating enzyme, respectively (Marie et al., 1993). INS-1 cells grow very slowly in the presence of 2-mercaptoethanol, and it remains to be determined whether glucose responsiveness and expression of GLUT-2 and glucokinase are retained with prolonged culturing of these cells.

Cell lines derived by transgenic expression of T-antigen in β-cells (generally termed bTC cells) also exhibit variable phenotypes (Efrat et al., 1988, Miyazaki et al., 1990, Whitesell et al., 1991 and Efrat et al., 1993). Some lines have little glucose-stimulated insulin release or exhibit maximal responses at subphysiological glucose concentrations (Efrat et al., 1988, Miyazaki et al., 1990, Whitesell et al., 1991), while others respond to glucose concentrations over the physiological range (Miyazaki et al., 1990 and Efrat et al., 1993). It appears that the near-normal responsiveness of the latter cell lines is not permanent, since further time in culture results in a shift in glucose dose response such that the cells secrete insulin at subphysiological glucose concentrations (Efrat et al., 1993). In some cases, these changes have been correlated with expression of glucose transporters and glucose phosphorylating enzymes.

Miyazaki et al. isolated two classes of clones from transgenic animals expressing an insulin promoter/T-antigen construct. Glucose unresponsive lines such as MIN-7 were found to express GLUT-1 rather than GLUT-2 as their major glucose transporter isoform, while MIN-6 cells were found to express GLUT-2 and to exhibit normal glucose-stimulated insulin secretion (Miyazaki et al., 1990).

More recently, Efrat and coworkers demonstrated that their cell line bTC-6, which exhibits a glucose-stimulated insulin secretion response that resembles that of the islet in magnitude and concentration dependence, expressed GLUT-2 and contained a glucokinase:hexokinase activity ratio similar to that of the normal islet (Efrat et al., 1993). With time in culture, glucose-stimulated insulin release became maximal at low, subphysiological glucose concentrations. GLUT-2 expression did not change with time in culture, and glucokinase activity actually increased slightly, but the major change was a large (approximately 6-fold) increase in hexokinase expression (Efrat et al., 1993). Furthermore, overexpression of hexokinase I, but not GLUT-1, in well-differentiated MIN-6 cells results in both increased glucose metabolism and insulin release at subphysiological glucose concentrations. Similar results have been obtained upon overexpression of hexokinase I in normal rat islets (Becker et al., 1994b). These results are all consistent with the observations of Ferber, et al. described above in showing that a high hexokinase:glucokinase ratio will cause insulin-secreting cells to respond to glucose concentrations less than those required to stimulate the normal β-cell.

(b) Non-glucose Responsive Cells

An alternative to insulinoma cell lines are non-islet cell lines of neuroendocrine origin that are engineered for insulin expression. The foremost example of this is the AtT-20 cell, which is derived from ACTH secreting cells of the anterior pituitary. Over a decade ago, Moore et al. demonstrated that stable transfection of AtT-20 cells with a construct in which a viral promoter is used to direct expression of the human proinsulin cDNA resulted in cell lines that secreted the correctly processed and mature insulin polypeptide (Moore et al., 1983). Insulin secretion from such lines (generally termed AtT-20ins) can be stimulated by agents such as forskolin or dibutyryl cAMP, with the major secreted product in the form of mature insulin, suggesting that these cells contain a regulated secretory pathway that is similar to that operative in the islet β-cell (Moore et al., 1983, Gross et al., 1989).

More recently, it has become clear that the peptidases that process proinsulin to insulin in the islet β-cell, termed PC2 and PC3, are also expressed in AtT-20ins cells (Smeekens et al., 1990, Hakes et al., 1991). AtT-20ins cells do not respond to glucose as a secretagogue (Hughes et al., 1991). Interestingly, AtT-20 cells express the glucokinase gene (Hughes et al., 1991, Liang et al., 1991) and at least in some lines, low levels of glucokinase activity (Hughes et al., 1991 and 1992, Quaade et al., 1991), but are completely lacking in GLUT-2 expression (Hughes et al., 1991and 1992). Stable transfection of these cells with GLUT-2, but not the related transporter GLUT-1 confers glucose-stimulated insulin secretion, albeit with maximal responsiveness at subphysiological glucose levels, probably because of a non-optimal hexokinase:glucokinase ratio (Hughes et al., 1992, 1993).

The studies with AtT-20ins cells are important because they demonstrate that neuroendocrine cell lines that normally lack glucose-stimulated peptide release may be engineered for this function. Other cell lines that are characterized as neuroendocrine, but lacking in endogenous glucose response include PC12, a neuronal cell line (ATCC CRL 1721) and GH3, an anterior pituitary cell line that secretes growth hormone (ATCC CCL82.1). It is not possible to determine whether such cell lines will gain glucose responsiveness by engineering similar to that described for the AtT-20ins cell system without performing the studies. However, these lines do exhibit other important properties, such as a regulated secretory pathway, expression of endopeptidases required for processing of prohormones to their mature hormone products, and post-translational modification enzymes.

In sum, all neuroendocrine cell lines are useful for recombinant protein production, and supplemented by the hexokinase inhibition methods disclosed herein, which is the production of heterologous products in a cell line in which the natural product (insulin, growth hormone, ACTH, etc.) has been eliminated. Some or all of these lines will also be useful for glucose-regulated product delivery, using the methods described in U.S. Pat. No. 5,427,940 to generate such responsiveness.

(c) Methods for Blocking Endogenous Protein Production

Blocking expression of an endogenous gene product is an important modification of host cells that may be used in combination with the present invention. The targeted endogenous gene encodes a protein normally secreted by the host cell. Blocking expression of this endogenous gene product, while engineering high level expression of genes of interest, represents a unique way of designing cells for protein production.

Cells generated by this two-step process express heterologous proteins, including a variety of natural or engineered proteins (fusions, chimeras, protein fragments, etc.). Cell lines developed in this are uniquely suited for in vivo cell-based delivery or in vitro large scale production of defined peptide hormones with little or no contaminating or unwanted endogenous protein production.

Four basic approaches are contemplated for blocking of expression of an endogenous gene in host cells. First, constructs are designed to homologously recombine into particular endogenous gene loci, rendering the endogenous gene nonfunctional. Second, constructs are designed to integrate randomly throughout the genome. Third, constructs are designed to introduce nucleic acids complementary to a target endogenous gene. Expression of RNAs corresponding to these complementary nucleic acids will interfere with the transcription and/or translation of the target sequences. And fourth, constructs are designed to introduce nucleic acids encoding ribozymes—RNA-cleaving enzymes—that will specifically cleave a target mRNA corresponding to the endogenous gene.

(i) Antisense

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs may include regions complementary to intron/exon splice junctions. Thus, antisense constructs with complementarity to regions within 50–200 bases of an intron-exon splice junction may be used. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

(ii) Homologous Recombination

Another approach for blocking of endogenous protein production involves the use of homologous recombination. Homologous recombination relies, like antisense, on the tendency of nucleic acids to base pair with complementary sequences. In this instance, the base pairing serves to facilitate the interaction of two separate nucleic acid molecules so that strand breakage and repair can take place. In other words, the "homologous" aspect of the method relies on sequence homology to bring two complementary sequences into close proximity, while the "recombination" aspect provides for one complementary sequence to replace the other by virtue of the breaking of certain bonds and the formation of others.

Put into practice, homologous recombination is used as follows. First, a target gene is selected within the host cell. Sequences homologous to the target gene are then included in a genetic construct, along with some mutation that will render the target gene inactive (stop codon, interruption, etc.). The homologous sequences flanking the inactivating mutation are said to "flank"the mutation. Flanking, in this context, simply means that target homologous sequences are located both upstream (5') and downstream (3') of the mutation. These sequences should correspond to some sequences upstream and downstream of the target gene. The construct is then introduced into the cell, thus permitting recombination between the cellular sequences and the construct.

As a practical matter, the genetic construct will normally act as far more than a vehicle to interrupt the gene. For example, it is important to be able to select for recombinants and, therefore, it is common to include within the construct a selectable marker gene. This gene permits selection of cells that have integrated the construct into their genomic DNA by conferring resistance to various biostatic and biocidal drugs. In addition, a heterologous gene that is to be expressed in the cell also may advantageously be included within the construct. The arrangement might be as follows:

. . . vector•5'-flanking sequence•heterologous gene•selectable marker gene•flanking sequence-3'•vector . . .

Thus, using this kind of construct, it is possible, in a single recombinatorial event, to (i) "knock out" an endogenous gene, (ii) provide a selectable marker for identifying such an event and (iii) introduce a heterologous gene for expression.

Another refinement of the homologous recombination approach involves the use of a "negative" selectable marker. This marker, unlike the selectable marker, causes death of cells which express the marker. Thus, it is used to identify undesirable recombination events. When seeking to select homologous recombinants using a selectable marker, it is difficult in the initial screening step to identify proper homologous recombinants from recombinants generated from random, non-sequence specific events. These recombinants also may contain the selectable marker gene and may express the heterologous protein of interest, but will, in all likelihood, not have the desired "knock out" phenotype. By attaching a negative selectable marker to the construct, but outside of the flanking regions, one can select against many random recombination events that will incorporate the negative selectable marker. Homologous recombination should not introduce the negative selectable marker, as it is outside of the flanking sequences.

In a particular aspect of this embodiment, the negative selectable maker may be GLUT-2. It is also contemplated that GLUT-5 would function in a similar manner to GLUT-2. Therefore, the selection protocols described below are intended to refer to the use of both GLUT-2 and GLUT-5.

In a first embodiment, a target gene within a GLUT-2 host cell is selected as the location into which a selected gene is to be transferred. Sequences homologous to the target gene are included in the expression vector, and the selected gene is inserted into the vector such that target gene homologous sequences are interrupted by the selected gene or, put another way, such the target gene homologous sequences "flank" the selected gene. In preferred embodiments, a drug selectable marker gene also is inserted into the target gene homologous sequences. Given this possibility, it should be apparent that the term "flank" is used broadly herein, namely, as describing target homologous sequences that are both upstream (5') and downstream (3') of the selected gene and/or the drug selectable marker gene. In effect, the flanking sequences need not directly abut the genes they "flank."

The construct for use in this embodiment is further characterized as having a functional GLUT-2 gene attached thereto. Thus, one possible arrangement of sequences would be:

. . . 5'-GLUT-2•flanking target sequences•selected gene•drug-selectable marker gene•flanking target sequences-3' . . .

Of course, the GLUT-2 could come at the 3'-end of the construct and the selected gene and drug-selectable marker genes could exchange positions.

Application of a drug to such cells will permit isolation of recombinants, but further application of Streptozotocin (glucopyranose, 2-deoxy-2-[3-methyl-e-nitrosourido-D]; STZ) to such cells will result in killing of non-homologous recombinants because the incorporated GLUT-2 gene will produce GLUT-2 transporter, rendering the cells susceptible to STZ treatment (the original cell was GLUT-2$^-$).

On the other hand, site-specific recombination, relying on the homology between the vector and the target gene, will result in incorporation of the selected gene and the drug selectable marker gene only; GLUT-2 sequences will not be introduced in the homologous recombination event because they lie outside the flanking sequences. These cells will be drug resistant and but not acquire the GLUT-2 sequences and, thus, remain insensitive to STZ. This double-selection procedure (drug$^{res}$/STZ$^{res}$) should yield recombinants that lack the target gene and express the selected gene. Further screens for these phenotypes, either functional or immunologic, may be applied.

A modification of this procedure is one where no selected gene is included, i.e., only the selectable marker is inserted into the target gene homologous sequences. Use of this kind of construct will result in the "knock-out" of the target gene only. Again, proper recombinants are screened by drug resistance and STZ resistance (the original cell was GLUT-2$^-$).

(iii) Random Integration

Though less specific than homologous recombination, there may be situations where random integration will be used as a method of knocking out a particular endogenous gene. Unlike homologous recombination, the recombinatorial event here is completely randon, i.e., not reliant upon base-pairing of complementary nucleic acid sequences. Random integration is like homologous recombination, however, in that a gene construct, often containing a heterologous gene and a selectable marker, integrates into the target cell genomic DNA via strand breakage and reformation.

Because of the lack of sequence specificity, the chances of any given recombinant integrating into the target gene are greatly reduced. As a result, it may be necessary to "brute force" the selection process. In other words, it may be necessary to screen hundreds of thousands of drug-resistant recombinants before a desired mutant is found. Screening can be facilitated, for example, by examining recombinants for expression of the target gene using immunologic or even functional tests; expression of the target gene indicate recombination elsewhere and, thus, lack of suitability.

(iv) Ribozymes

The use of hexokinase-specific ribozymes has been described herein above. However, while the inhibition of hexokinase is intended for use in a recombinant cell which is also used for high level protein production, additional ribozymes may also be used to block endogenous protein production. The following information is provided in order to compliment the earlier section and to assist those of skill in the art in this endeavor.

Ribozymes are RNA-protein complexes that cleave nucleic acids in a site-specific fashion. Ribozymes have specific catalytic domains that possess endonuclease activity (Kim and Cook, 1987; Gerlack et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant condon that is cleaved by a specific ribozyme. In light of the information included herein and the knowledge of one of ordinary skill in the art, the preparation and use of additional ribozymes that are specifically targeted to a given gene will now be straightforward.

(d) Methods for Increasing Production of Recombinant Peptides from Secretory Cells The present invention may also be used in methods for augmenting or increasing the capabilities of cells to produce biologically active polypeptides. This can be accomplished, in some instances, by overexpressing the proteins involved in protein processing, such as the endoproteases PC2 and PC3 (Steiner et al., 1992) or the peptide amidating enzyme, PAM (Eipper et al., 1992a) in the case of peptide hormones.

Expression of proteins involved in maintaining the specialized phenotype of host cells, especially their secretory capacity, is important. Engineering the overexpression of a cell type-specific transcription factor such as the Insulin Promoter Factor 1 (IPF1) found in pancreatic β cells (Ohlsson et al., 1993) could increase or stabilize the capabilities of engineered neuroendocrine cells. Insulin promoter factor 1 (IPF-1; also referred to as STF-1, IDX-1, PDX-1 and βTF-1) is a homeodomain-containing transcription factor proposed to play an important role in both pancreatic development and insulin gene expression in mature β cells (Ohlsson et al., 1993, Leonard et al., 1993, Miller et al., 1994, Kruse et al., 1993). In embryos, IPF-1 is expressed prior to islet cell hormone gene expression and is restricted to positions within the primitive foregut where pancreas will later form. Indeed, mice in which the IPF-1 gene is disrupted by targeted knockout do not form a pancreas (Jonsson et al., 1994). Later in pancreatic development, as the different cell types of the pancreas start to emerge, IPF-1 expression becomes restricted predominantly to β cells. IPF-1 binds to TAAT consensus motifs contained within the FLAT E and P1 elements of the insulin enhancer/promoter, whereupon, it interacts with other transcription factors to activate insulin gene transcription (Peers et al. 1994).

Stable overexpression of IPF-1 in neuroendocrine β cell lines will serve two purposes. First, it will increase transgene expression under the control of the insulin enhancer/promoter. Second, because IPF-1 appears to be critically involved in β cell maturation, stable overexpression of IPF-1 in β cell lines should cause these mostly dedifferentiated β-cells to regain the more differentiated function of a normal animal β cell. If so, then these redifferentiated β cell lines could potentially function as a more effective neuroendocrine cell type for cell-based delivery of fully processed, bioactive peptide hormones.

Also, further engineering of cells to generate a more physiologically relevant regulated secretory response is contemplated. Examples would include engineering overexpression of other signalling proteins known to play a role in the regulated secretory response of neuroendocrine cells. These include cell surface proteins such as the β-cell specific inwardly rectifying potassium channel (sulfonylurea receptor, SUR, and ATP sensitive channel, BIR; Inagaki et al., 1995), involved in release of the secretory granule contents upon glucose stimulation. Other cell surface signalling receptors which help potentiate the glucose stimulated degranulation of β-cells including the glucagon-like peptide I receptor (Thorens, 1992) and the glucose-dependent insulinotropic polypeptide receptor (also known as gastric inhibitory peptide receptor) (Usdin, 1993) can be engineered into neuroendocrine cells. These β-cell specific signaling receptors, as well as GLUT-2 and glucokinase, are involved in secretory granule release in response to glucose. In this way glucose stimulated release of any heterologous peptide targeted to the secretory granule can be engineered.

Alternatively, other cell surface signaling proteins involved in non-glucose stimulated release of secretory granule contents can be engineered into neuroendocrine cells. Examples would include releasing factor receptors such as Growth Hormone Releasing Factor Receptor (Lin et al., 1992) and Somatostatin or Growth Hormone Releasing Hormone Receptor (Mayo, 1992). Engineering these receptors, and receptors specific for other releasing factors, into neuroendocrine cell lines should result in physiological release of heterologous peptides targeted to the secretory granules for either in vivo cell based delivery or for in vitro production.

(e) Methods for Re-engineering Engineered Cells

In many situations, multiple rounds of iterative engineering will be undertaken in generating the final cell lines. The events that may be conducted as separate construction events include blocking expression of endogenous gene products by molecular methods (including targeting of both copies of the endogenous gene), introducing a heterologous gene, and further modification of the host cell to achieve high level expression. The particular difficulty in performing multiple steps like this is the need for distinct selectable markers. This is a limitation in that only a few selectable markers are available for use in mammalian cells and not all of these work sufficiently well for many purposes.

The Cre/Lox site specific recombination system (Sauer, 1993, available through Gibco/BRL, Inc., Gaithersburg, Md.) may be used to rescue specific genes out of a genome, especially drug selection markers, as a way of increasing the number of rounds of engineering. Briefly, the system involves the use of a bacterial nucleotide sequence knows as a LoxP site, which is recognized by the bacterial Cre protein. The Cre protein catalyzes a site specific recombination event. This event is bidirectional, i.e., Cre will catalyze the insertion of sequences at a LoxP site or excise sequences that lie between two LoxP sites. Thus, if a construct containing a selectable marker also has LoxP sites flanking the selectable marker, introduction of the Cre protein, or a polynucleotide encoding the Cre protein, into the cell will catalyze the removal of the selectable marker. If successfully accomplished, this will make the selectable marker again available for use in further genetic engineering of the cell. This technology is explained in detail in U.S. Pat. No. 4,959,317, which is hereby incorporated by reference in its entirety.

It also is contemplated that a series of different markers may be employed in some situations. These markers are discussed in greater detail, below.

(f) Proteins

A variety of different proteins can be expressed in which hexokinase has been inhibited according to the present invention. Proteins can be grouped generally into two categories—secreted and non-secreted—discussions of each are set out below. There are some general properties of proteins that are worthy of discussion at this juncture.

First, it is contemplated that many proteins will not have a single sequence but, rather, will exists in many forms. These forms may represent allelic variation or, rather, mutant forms of a given protein. Second, it is contemplated that various proteins may be expressed advantageously as "fusion" proteins. Fusions are generated by linking together the coding regions for two proteins, or parts of two proteins. This generates a new, single coding region that gives rise to the fusion protein. Fusions may be useful in producing secreted forms of proteins that are not normally secreted or producing molecules that are immunologically tagged. Tagged proteins may be more easily purified or monitored using antibodies to the tag. A third variation contemplated involves the expression of protein fragments. It may not be necessary to express an entire protein and, in some cases, it may be desirable to express a particular functional domain, for example, where the protein fragment remains functional but is more stable or less antigenic.

(i) Secreted Proteins

Expression of several proteins that are normally secreted can be engineered into neuroendocrine cells. The cDNA's encoding a number of useful human proteins are available. Examples would include soluble CD-4, Factor VIII, Factor IX, von Willebrand Factor, TPA, urokinase, hirudin, interferons, TNF, interleukins, hematopoietic growth factors, antibodies, glucocerebrosidase, adenosine deaminase, phenylalanine hydroxylase, albumin, transferin and nerve growth factors.

The exogenous polypeptide may be a hormone, such as growth hormone, prolactin, placental lactogen, luteinizing hormone, follicle-stimulating hormone, chorionic gonadotropin, thyroid-stimulating hormone, adrenocorticotropin (ACTH), angiotensin I, angiotensin II, beta-endorphin, beta-melanocyte stimulating hormone (beta-MSH), cholecystokinin, endothelin I, galanin, gastric inhibitory peptide (GIP), glucagon, insulin, lipotropins, neurophysins and somatostatin.

The exogenous polypeptide to be secreted may be amidated or a fusion protein. Amidated polypeptides include calcitonin, calcitonin gene related peptide (CGRP), beta-calcitonin gene related peptide, hypercalcemia of malignancy factor (1-40), parathyroid hormone-related protein (107-139) (PTH-rP), parathyroid hormone-related protein (107-111) (PTH-rP), cholecystokinin (27-33) (CCK), galanin message associated peptide, preprogalanin (65-105), gastrin I, gastrin releasing peptide, glucagon-like peptide (GLP-1), pancreastatin, pancreatic peptide, peptide YY, PHM, secretin, vasoactive intestinal peptide (VIP), oxytocin, vasopressin (AVP), vasotocin, enkephalins, enkephalinamide, metorphinamide (adrenorphin), alpha melanocyte stimulating hormone (alpha-MSH), atrial natriuretic factor (5-28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

(ii) Non-Secreted Proteins

Expression of non-secreted proteins can be engineered into neuroendocrine cells. The cDNA's encoding a number of useful human proteins are available. These include cell surface receptors and channels such as GLUT-2, CFTR and the leptin receptor.

(g) Growth-Rate Reduced Cells

In that inhibiting one or more hexokinases is intended as a method for slowing the growth of a mammalian cell, cells from virtually any established cell line that grows continuously in culture may be used in these aspects of the invention. Examples of such mammalian host cell lines include VERO cells, HeLa cells, Chinese hamster ovary (CHO) cell lines, COS cells, such as COS-7, W138, BHK, HepG2, 3T3, RIN, MDCK, A549, PC12, K562 and 293 cells.

Cells intended for use in generating monoclonal antibodies (MAbs) may also be provided with a low $K_m$ hexokinase inhibitor, or be rendered hexokinase deficient, in order to slow their growth rate. MAbs are readily prepared through use of well-known techniques, such as those exemplified in U.S. Pat. No. 4,196,265, incorporated herein by reference.

MAb-producing cells are generally hybrid cells derived from the fusion of a somatic cell that has the potential to produce antibodies, specifically a B lymphocyte or B cell, with an immortal myeloma cell, generally one of the same species as the animal that was immunized in order to provide the B cells. Such cells that have reduced low $K_m$ hexokinase activity form another aspect of this invention.

Primary cell lines are also contemplated for use with these aspects of the invention. Primary cell lines are those cells that have been removed from an animal or human subject and are capable of surviving in culture for a limited period of time. Such cells are often manipulated, e.g., to introduce a beneficial gene that expresses a selected protein, and then re-introduced into the animal from which they were originally obtained. This technique is often termed ex vivo gene therapy, and can be used to deliver cytotoxic proteins, e.g., to cancer cells, and therapeutic proteins intended to correct a deficiency in a given cell type or types.

Primary cells of all vertebrate species are thus considered for use with the hexokinase inhibition aspects of this invention, whether or not they are returned to the body of an animal. These include, by way of example only, bone marrow cells, nerve cells, lung epithelial cells and hepatocytes.

Cells that contain a low $K_m$ hexokinase inhibitor and which are located within an animal or human subject are also encompassed within the cells of the invention, whether or not they were originally derived from the animal. Cells that were not so-obtained from the ultimate host animal may be cells from an immunologically compatible animal, cells that have been immunologically modified or disabled, cells that are protected within a semi-permeable device in the host animal and even cells that are largely unmodified in immunological terms and that are intended to have a temporary life span within the host animal.

2. Genetic Constructs

DNA expression plasmids may be used to optimize production of hexokinase inhibitors and/or heterologous proteins. A number of promoter/enhancers from both viral and mammalian sources may be used to drive expression of the genes of interest in neuroendocrine cells. Elements designed to optimize messenger RNA stability and translatability in neuroendocrine cells are defined. The conditions for the use of a number of dominant drug selection markers for establishing permanent, stable neuroendocrine cell clones expressing the peptide hormones are also provided, as is an element that links expression of the drug selection markers to expression of the heterologous polypeptide.

(a) Vector Backbone

Throughout this application, the term "expression vector or construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid encoding a particular gene is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter and the Rous sarcoma virus long terminal repeat can be used to obtain high-level expression of the gene of interest. The use of other viral or mammalian cellular or bacterial phage promoters which are well-known in the art to achieve expression of a gene of interest is contemplated as well, provided that the levels of expression are sufficient for a given purpose.

By employing a promoter with well-known properties, the level and pattern of expression of the gene product following transfection can be optimized. Further, selection of a promoter that is regulated in response to specific physiologic signals can permit inducible expression of the gene product. Tables 4 and 5 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Viral promoters, cellular promoters/enhancers and inducible promoters/enhancers could be used in combination with the nucleic acid encoding a gene of interest in an expression construct. Some examples of enhancers include Immunoglobulin Heavy Chain; Immunoglobulin Light Chain; T-Cell Receptor; HLA DQ α and DQ β β-Interferon; Interleukin-2; Interleukin-2 Receptor; Gibbon Leukemia Virus; MHC Class II 5 or HLA-DRα; β-Actin; Muscle Creatine Kinase; Prealbumin (Transthyretin); Elastase I; Metallothionein; Collagenase; Albumin Gene; α-Fetoprotein; α-Globin; α-Globin; c-fos; c-HA-ras; Insulin Neural Cell Adhesion Molecule (NCAM); α1-Antitrypsin; H2B (TH2B) Histone; Mouse or Type I Collagen; Glucose-Regulated Proteins (GRP94 and GRP78); Rat Growth Hormone; Human Serum Amyloid A (SAA); Troponin I (TN I); Platelet-Derived Growth Factor; Duchenne Muscular Dystrophy; SV40 or CMV; Polyoma; Retroviruses; Papilloma Virus; Hepatitis B Virus; Human Immunodeficiency Virus. Inducers such as phorbol ester (TFA) heavy metals; glucocorticoids; poly (rI)X; poly(rc); Ela; $H_2O_2$; IL-1; Interferon, Newcastle Disease Virus; A23187; IL-6; Serum; SV40 Large T Antigen; FMA; thyroid Hormone; glucose could be used. Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

In preferred embodiments, the expression construct will comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal et al., 1986; Temin, 1986). The first viruses used as gene vectors were DNA viruses including the papovaviruses (simian virus 40, bovine papilloma virus, and polyoma) (Ridgeway, 1988; Baichwal et al., 1986) and adenoviruses (Ridgeway, 1988; Baichwal et al., 1986). These have a relatively low capacity for foreign DNA sequences and have a restricted host spectrum. Furthermore, their oncogenic potential and cytopathic effects in permissive cells raise safety concerns. They can accommodate only up to 8 kB of foreign genetic material but can be readily introduced in a variety of cell lines and laboratory animals (Nicolas and Rubenstein, 1988; Temin, 1986).

(b) Regulatory Elements

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. The inventors have employed the human Growth Hormone and SV40 polyadenylation signals in that they were convenient and known to function well in the target cells employed. Also contemplated as an element of the expression cassette is a terminator. These elements can serve to enhance message levels and to minimize read through from the cassette into other sequences.

(c) Selectable Markers

In certain embodiments, the delivery of a nucleic acid in a cell may be identified in vitro or in vivo by including a marker in the expression construct. The marker would result in an identifiable change to the transfected cell permitting easy identification of expression. Usually the inclusion of a drug selection marker aids in cloning and in the selection of transformants, for example, neomycin, puromycin, hygromycin, DHFR, GPT, zeocin and histidinol. Alternatively, enzymes such as herpes simplex virus thymidine kinase (tk) (eukaryotic) or chloramphenicol acetyltransferase (CAT) (prokaryotic) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(d) Multigene Constructs and IRES

In certain embodiments, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each seperated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins encoded by independent genes, intracellular or membrane-bound proteins and selectable markers. In this way expression of several proteins can be simultaneously engineered into a cell with a single construct and a single selectable marker.

3. Biological Functional Equivalents

Various nucleic acid and protein sequences are described herein that may be used in the diverse hexokinase inhibition methods of the present invention. Particularly preferred genes and proteins are trehalose-6-phosphate synthase (TPS1); hexokinase I; hexokinase II; hexokinase III; glucokinase (hexokinase IV); and fragments thereof. The following description is provided in order to further explain the equivalents of the foregoing genes and proteins that will be understood by those of skill in the art to fall within the scope of the present invention.

(a) Proteins and DNA Segments

As used herein, in the context of the foregoing nucleic acid sequences, the terms "gene", "DNA segment" and "polynucleotide" refer to DNA molecules that have been isolated free of total genomic DNA of a particular species. Therefore, the DNA segments encode their respective proteins or polypeptides, but are isolated away from, or purified free from, total genomic DNA. Included within the term "DNA segment", are DNA segments and smaller fragments of such segments, and also recombinant vectors, including, for example, plasmids, cosmids, phage, viruses, and the like.

DNA segments such as those encoding TPS1, low $K_m$ hexokinase, glucokinase, and other polypeptides and proteins described herein may comprise isolated or purified genes including their respective coding sequences and, in certain aspects, regulatory sequences, isolated substantially away from other naturally occurring genes or protein encoding sequences. In this respect, the term "gene" is used for simplicity to refer to a functional protein encoding unit. As will be understood by those in the art, this functional term includes both genomic sequences and cDNA sequences.

"Isolated substantially away from other coding sequences" means that the particular protein-encoding unit forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, this invention concerns the use of isolated DNA segments and recombinant vectors incorporating DNA sequences that encode various proteins defined herein in terms of their amino acid sequences. Other sequences that are "essentially" as set forth in the sequence identifiers are, of course, encompassed within the invention. The term "a sequence essentially as set forth in" means that the sequence substantially corresponds to a portion of the recited sequence and has relatively few amino acids that are not identical to, or a biologically functional equivalent of, the amino acids of the recited sequence.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of a recited sequence will be sequences that are "essentially as set forth in the recited sequence. Naturally, there is the very important provision that to be "equivalent" the encoded protein must function essentially in the same way as the recited protein. This is particularly important in the present invention, where the different kinetic properties of isoenzymes catalysing the same biochemical steps lies at the heart of several features of the invention. However, with this in mind, there are still a number of equivalents and sequence variants of the aforementioned proteins that can be generated and used.

In certain other embodiments, the invention concerns the use of isolated DNA segments and recombinant vectors that include within their sequence a nucleic acid sequence essentially as set forth in a recited sequence identifier. The term "essentially as set forth in", when referring to nucleic acids, is used in the same sense as described above and means that the nucleic acid sequence substantially corresponds to a portion of the recited sequence and has relatively few codons that are not identical, or functionally equivalent, to the codons of the recited sequence. The term "functionally equivalent codon" is used herein to refer to codons that encode the same amino acid, such as the six codons for arginine or serine, and also refers to codons that encode biologically equivalent amino acids, as set forth in the table below.

TABLE 2

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | B | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAN | AAG | | | | |
| Leucine | Leu | L | UUA | UUG | CUA | CVC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Accordingly, DNA segments prepared in accordance with the present invention may also encode biologically functional equivalent proteins or peptides that have variant amino acids sequences. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged, as described herein.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity following expression, where proteins are concerned. The addition of terminal sequences particularly applies to nucleic acid sequences for use in vectors that may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences that have between about 70% and about 80%; or more preferably, between about 81% and about 90%; or even more preferably, between about 91% and about 99%; of nucleotides that are identical to the nucleotides of a recited sequence will be sequences that are "essentially as set forth in the recited sequence. Sequences that are essentially the same as those set forth in a recited sequence may also be functionally defined as sequences that are capable of hybridizing to a nucleic acid segment containing the complement of the recited sequence under relatively stringent conditions. Suitable relatively stringent hybridization conditions are well known to those of skill in the art.

(b) Biological Functional Equivalents

Modification and changes may be made in the structure of protein molecules and still obtain other molecules having like characteristics. For example, certain amino acids may be substituted for other amino acids in a protein structure without appreciable loss of interactive binding capacity with structures such as, for example, substrates and effectors.

Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties. Equally, it is these same type considerations that are employed to create a protein or polypeptide with counterveiling (or antagonistic) properties, as discussed herein in terms of modifying hexokinase and/or glucokinase sequences to provide mutants with selected features.

In terms of maintaining protein function essentially as in the wild type, or natural molecule, it is thus contemplated by the inventors that various changes may be made in the sequence of a given protein or peptides (or underlying DNA) without appreciable loss of their biological utility or activity.

It is also well understood by the skilled artisan that, inherent in the definition of a biologically functional equivalent protein, is the concept that there is a limit to the number of changes that may be made within a defined portion of the molecule and still result in a molecule with an acceptable level of equivalent biological activity. Biologically functional equivalents are thus defined herein as those proteins in which only certain, not most or all, of the amino acids have been substituted. To be equivalent, the overall function or kinetic parameters of the resultant protein cannot be significantly changed. However, a plurality of distinct proteins with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention where many residues are critical.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes/In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. It is known that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent proteins arising from amino acid changes, it will be appreciated that these changes may be effected by alteration of the encoding DNA: taking into consideration also that the genetic code is degenerate and that two or more codons may code for the same amino acid. The table of amino acids and their codons, presented herein above, is useful in the design of mutant proteins and in DNA probes and primers and the like.

(c) Site-Specific Mutagenesis

Site-specific mutagenesis is a technique useful in the preparation of modified proteins through specific mutagenesis of the underlying DNA. The technique further provides a ready ability to prepare and test sequence variants by introducing one or more nucleotide sequence changes into the DNA. The techniques are generally well known, as exemplified by U.S. Pat. No. 4,888,286, incorporated herein by reference.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes GLUT-2. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement. Further relevant publications include Adelman et al. (1983).

The preparation of sequence variants of GLUT-2 using site-directed mutagenesis is provided as one means of producing useful species and is not meant to be limiting as there are other ways in which sequence variants of GLUT-2 may be obtained. For example, recombinant vectors encoding GLUT-2 may be treated with mutagenic agents to obtain sequence variants (see, e.g., a method described by Eichenlaub, 1979) for the mutagenesis of plasmid DNA using hydroxylamine.

Although the foregoing methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

4. In Vivo Delivery and Treatment Protocols (a) Adenovirus

One of the preferred methods for in vivo delivery involves the use of an adenovirus expression vector. "Adenovirus expression vector" is meant to include those constructs containing adenovirus sequences sufficient to support packaging of the construct and to express an antisense polynucleotide that has been cloned therein. In this context, expression does not require that the gene product be synthesize.

The expression vector comprises a genetically engineered form of adenovirus. Knowledge of the genetic organization or adenovirus, a 36 kB, linear, double-strained DNA virus, allows substitution of large pieces of adenoviral DNA with foreign sequences up to 7 kB (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system in is an alternative approach for the production of recombinant adenovirus.

Generation and propagation of adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the E3 or both regions (Graham and Prevec, 1991).

In nature, adenovirus can package approximately 105% of the wild-type genome (Ghosh-Choudhury et al., 1987), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity.

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al. (1995) disclosed improved methods for culturing 293 cells and propagating adenovirus. In one format, natural cell aggregates are grown by inoculating individual cells into 1 L siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, it has historically been used for most constructions employing adenovirus as a vector and it is non-oncogenic.

As stated above, a typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus can be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

(b) Retroviruses

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a human cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

(c) Other Viral Vectors as Expression Constructs

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al. recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

(d) Non-viral vectors

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. As described above, the preferred mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a gene of interest may also be transferred in a similar manner in vivo and express the gene product.

Another embodiment for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialogangliposide, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

(e) Pharmaceutical Compositions

Where clinical applications are contemplated, it will be necessary to prepare a pharmaceutical composition—either gene delivery vectors or engineered cells—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

Solutions of the active ingredients as free base or pharmacologically acceptable salts can be prepared in water suitably mixed with surfactant, such as hydroxypropylcellulose. Dispersions also can be prepared in glycerol, liquid polyethylene glycols, mixtures thereof and in oils. Under ordinary conditions of storage and use, these preparations contain a preservative to prevent growth of microorganisms.

The expression vectors and delivery vehicles of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The vectors and cells of the present invention are advantageously administered in the form of injectable compositions either as liquid solutions or suspensions; solid forms suitable for solution in, or suspension in, liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well know parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

(f) Cell Implantation

It is proposed that engineered cells of the present invention, including those that respond to glucose by secreting insulin, those that deliver other polypeptides and/or those having reduced growth rates, may be introduced into animals with certain needs, such as animals with insulin-dependent diabetes.

In the diabetic treatment aspects, ideally cells are engineered to achieve glucose dose responsiveness closely resembling that of islets. However, other cells will also achieve advantages in accordance with the invention. It should be pointed out that the experiments of Madsen and coworkers have shown that implantation of poorly differentiated rat insulinoma cells into animals results in a return to a more differentiated state, marked by enhanced insulin secretion in response to metabolic fuels (Madsen, et al., 1988). These studies suggest that exposure of engineered cell lines to the in vivo milieu may have some effects on their response(s) to secretagogues.

The preferred methods of administration involve the encapsulation of the hexokinase-inhibited cells in a biocompatible coating. In this approach, the cells are entrapped in a capsular coating that protects the contents from immunological responses. One preferred encapsulation technique involves encapsulation with alginate-polylysine-alginate. Capsules made employing this technique generally have a diameter of approximately 1 mm and should contain several hundred cells.

Cells with reduced low $K_m$ hexokinase activity in accordance herewith may thus be implanted using the alginate-polylysine encapsulation technique of O'Shea and Sun (1986), with modifications, as later described by Fritschy, et al. (1991). The engineered cells are suspended in 1.3% sodium alginate and encapsulated by extrusion of drops of the cell/alginate suspension through a syringe into $CaCl_2$. After several washing steps, the droplets are suspended in polylysine and rewashed. The alginate within the capsules is then reliquified by suspension in 1 mM EGTA and then rewashed with Krebs balanced salt buffer.

An alternative approach is to seed Amicon fibers with cells of the present invention. The cells become enmeshed in the fibers, which are semipermeable, and are thus protected in a manner similar to the micro encapsulates (Altman, et al., 1986). After successful encapsulation or fiber seeding, the cells may be implanted intraperitoneally, usually by injection into the peritoneal cavity through a large gauge needle (23 gauge).

A variety of other encapsulation technologies have been developed that are applicable to the practice of the present invention (see, e.g., Lacy et al., 1991; Sullivan et al., 1991; WO 91/10470; WO 91/10425; WO 90/15637; WO 90/02580; U.S. Pat. No. 5,011,472; U.S. Pat. No. 4,892,538; and WO 8901967, each of the foregoing being incorporated by reference).

Lacy et. al. (1991)encapsulated rat islets in hollow acrylic fibers and immobilized these in alginate hydrogel. Following intraperitoneal transplantation of the encapsulated islets into diabetic mice, normoglycemia was reportedly restored. Similar results were also obtained using subcutaneous implants that had an appropriately constructed outer surface on the fibers. It is therefore contemplated that engineered cells of the present invention may also be straightforwardly "transplanted" into a mammal by similar subcutaneous injection.

Sullivan et. al. (1991) reported the development of a biohybrid perfused "artificial pancreas", which encapsulates islet tissue in a selectively permeable membrane. In these studies, a tubular semi-permeable membrane was coiled inside a protective housing to provide a compartment for the islet cells. Each end of the membrane was then connected to an arterial polytetrafluoroethylene (PTFE) graft that extended beyond the housing and joined the device to the vascular system as an arteriovenous shunt. The implantation of such a device containing islet allografts into pancreatectomized dogs was reported to result in the control of fasting glucose levels in 6/10 animals. Grafts of this type encapsulating engineered cells could also be used in accordance with the present invention.

The company Cytotherapeutics has developed encapsulation technologies that are now commercially available that will likely be of use in the application of the present invention. A vascular device has also been developed by Biohybrid, of Shrewsbury, Mass., that may have application to the technology of the present invention.

Implantation employing such an encapsulation technique are preferred for a variety of reasons. For example, transplantation of islets into animal models of diabetes by this method has been shown to significantly increase the period of normal glycemic control, by prolonging xenograft survival compared to unencapsulated islets (O'Shea, et al., 1986; Fritschy, et al., 1991). Also, encapsulation will prevent uncontrolled proliferation of clonal cells. Capsules containing cells are implanted (approximately 1,000–10,000/ animal) intraperitoneally and blood samples taken daily for monitoring of blood glucose and insulin.

An alternate approach to encapsulation is to simply inject glucose sensing cells into the scapular region or peritoneal cavity of diabetic mice or rats, where these cells are reported to form tumors (Sato, et al., 1962). Implantation by this approach may circumvent problems with viability or function, at least for the short term, that may be encountered with the encapsulation strategy. This approach will allow testing of the function of the cells in experimental animals but obviously is not applicable as a strategy for treating human diabetes.

Engineering of primary cells isolated from patients is also contemplated as described by Dr. Richard Mulligan and colleagues using retroviral vectors for the purposes of introducing foreign genes into bone marrow cells (see, e.g., Cone, et al., 1984; Danos, et al., 1988). The cells of the bone marrow are derived from a common progenitor, known as pluripotent stem cells, which give rise to a variety of blood borne cells including erythrocytes, platelets, lymphocytes, macrophages, and granulocytes. Interestingly, some of these cells, particularly the macrophages, are capable of secreting peptides such as tumor necrosis factor and interleukin 1 in response to specific stimuli. There is also evidence that these cells contain granules similar in structure to the secretory granules of β-cells, although there is no clear evidence that such granules are collected and stored inside macrophages as they are in β-cells (Stossel, 1987).

It may ultimately be possible to use the present hexokinase-inhibition technology in combination with that previously described by the one of the present inventors (U.S. Pat. No. 5,427,940, incorporated herein by reference) in a manner described for clonal cells to engineer primary cells that perform glucose-stimulated insulin secretion. This approach would completely circumvent the need for encapsulation of cells, since the patient's own bone marrow cells would be used for the engineering and then re-implanted. These cells would then develop into their differentiated form (i.e., the macrophage) and circulate in the blood where they would be able to sense changes in circulating glucose by secreting insulin.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Expression Vectors

The present example describes expression vectors that have been found to be particularly useful in the context of the invention.

Initial expression plasmids were based on pCB6 and pCB7 (Brewer, 1994). These plasmids utilize the strong promoter/enhancer of the human Cytomegalovirus (CMV) immediate-early regulatory sequence capable of driving expression of inserted genes of interest. Efficient polyadenylation of transcribed messenger RNA is directed by the human Growth Hormone polyadenylation sequence. pCB6 encodes the Neomycin resistance gene conferring resistance to the neomycin analog G418 while pCB7 encodes the hygromycin resistance gene. Both resistant markers are transcribed by the SV40 early promoter.

A second expression plasmid was constructed with many of the same elements as pCB6. The open reading frame of the neomycin resistance gene was amplified with the polymerase chain reaction from pCB6 (Brewer, 1994) using oligos (CCGGATCCCATGATTGAACAAGAT; SEQ ID NO:23 and CCAAGATCTCGCTCAGAAGAACTC; SEQ ID NO:24). The resulting 816 bp. amplified product was restricted with BamHI and BglII and subcloned into the BamH1 site of pCMV8, generating pCMV8/NEO/hGH PolyA.

pCMV8 was derived from pCMV4 (Anderson et al., 1989) following removal of the alpha mosaic virus 4 RNA translational enhancer and replacing it with the 5' leader sequence of the adenovirus tripartite leader (+14 to +154 of major late transcript) fused to a hybrid intron composed of the adenovirus major late transcript 5' donor site and a 3' splice site from a variable region immunoglobulin gene (Kaufman and Sharp, 1982).

A portion of the gene encoding the 5' transcribed leader of the human Glucose Regulated Protein 78 (GRP78) was amplified using the polymerase chain reaction from pThu6.5 (corresponding to bases 372 to 594, Ting and Lee, 1988) using oligos (CCGGATCCAGGTCGACGCCGGCCAA; SEQ ID NO:25 and CGAGATCTTGCCAGCCAGTTGG; SEQ ID NO:26), generating A construct with the sequence of SEQ ID NO:10. The 5' leader of human GRP 78 has been shown to direct internal initiation of translation allowing for construction of functional polycistronic genes in mammalian cells (Macejak and Sarnow, 1991).

The 235 bp. amplified product (SEQ ID NO:10) was restricted with BamHI and BglII and subcloned into the BamH1 site of pCMV8/NEO/hGH PolyA generating pCMV8/IRES/NEO/hGH PolyA. Unique restriction endonuclease sites exist (5' Sal1/Xba1/BamH1 3') for subcloning fragments into this expression plasmid between the CMV promoter/intron and the internal ribozyme entry site/NEO elements. cDNA's or other open reading frames cloned into these sites are transcribed from the CMV promoter into a bicistronic message containing the cDNA as the upstream open reading frame and neomycin resistance (NEO) as the downstream open reading frame. Both open reading frames are translated efficiently, linking neomycin drug resistance and expression of the upstream gene of interest.

A final expression plasmid was designed for expression of genes of interest. The 5' elements found in pCMV8 composed of the 5' leader sequence of the adenovirus tri-partite leader (+14 to +154 of major late transcript) fused to a hybrid intron composed of the adenovirus major late transcript 5' donor site and a 3' splice site from a variable region immunoglobulin gene (Kaufman and Sharp, 1982) was removed by endonuclease restriction by SnaB1 and BamH1 and ligated into SnaB1 and BglII restricted pCB6 (Brewer, 1994), generating pCB6/intron. SnaB1 cuts uniquely in both plasmids at identical positions in the CMV promoter sequence.

pCB6/intron has several unique endonuclease restriction sites for subcloning fragments downstream of the intron sequence and upstream of the hGH PolyA sequence (5' Xba1/Kpn1/Mlu1/Cla1/BspD1/Xba1/BamH1 3'). The neomycin resistance gene is transcribed using the SV40 promoter from an independent transcriptional unit encoded on the plasmid (Brewer, 1994).

EXAMPLE II

The N terminal Domain of Hexokinase Inhibits Hexokinase Binding to Mitochondria The present example describes truncated hexokinase compositions and methods for displacing hexokinase from mitochondria, thus inhibiting the enzyme. These methods and the protein constructs used in this manner form one aspect of the so-called "dominant negative" strategies and proteins of the invention.

A. Materials and Methods

1. Expression Plasmids

An EcoR1/Nco1 fragment corresponding to bases 1 to 1452 of rat hexokinase I cDNA (SEQ ID NO:6, Schwab and Wilson, 1989) was isolated encoding the first 455 amino acids of Hexokinase I (SEQ ID NO:7). SEQ ID NO:7 represents the entire N terminal half of the protein and should fold into a stable domain containing the hexokinase I non-catalytic, regulatory domain as well as the mitochondrial binding domain targeting hexokinase I to the outer mitochondrial membrane (Polakis and Wilson, 1985).

The 1463 base fragment was treated with Klenow Fragment to blunt the ends and ligated into pCMV8/IRES/NEO/hGH PolyA that had been digested with Xba1 and Klenow treated. The resulting plasmid, pCMV8/HKNterm/IRES/NEO, will express the 455 amino acid hexokinase domain with an additional 33 novel amino acids that are in frame as encoded by the plasmid. The neomycin resistance gene is encoded in the downstream open reading frame.

Alternatively, the same Klenow treated 1463 base fragment was ligated into pCB6/intron that had been previously digested with Xba1 and treated with Klenow. The resulting plasmid, pCB6/intron/HKNterm, will express the 455 amino acid hexokinase domain with an additional 27 novel amino acids that are in frame as encoded by the plasmid. The neomycin resistance gene is independently transcribed off of the SV40 promoter.

2. Cell Culture

RIN 1046-38 cells (Gazdar et al., 1980; Clark et al., 1990) were grown in Medium 199 with Earle's salts, containing 11 mM glucose and supplemented with 5% fetal calf serum (Mediatech, Washington, D.C.), 100 milliunits/ml penicillin and 100 µg/ml streptomycin. Cells were passaged once a week using 0.05% trypsin—EDTA solution and kept under an atmosphere of 95% air and 5% $CO_2$ at 37° C. The human embryonic kidney cell line, 293, was obtained from the American Type Culture Collection, Bethesda, Md. (ATCC CRL 1573) and cultured as recommended.

3. Stable Transfection of Cell Lines

Cells were transfected by electroporation (BTX, Inc., San Diego, Calif., Electro Cell Manipulator 600) using 10–20× $10^6$ cells/ml with expression plasmids at a concentration of 30 µg/ml in a 0.2 cm cuvette at settings of 165–170 volts and 450–500 µF. Initial drug selection of stable transformants was done using 500 µg/ml active fraction G418 (Geneticin, Gibco Life Sciences) for 10 days without media changes.

4. Northern Analysis

Total RNA from RIN cell lines grown in vitro was isolated using RNAzol B RNA Isolation Reagent (Cinna/Biotex Laboratories Int., Friendswood, Tex.). 10 µg total RNA was resolved on methyl mercury/1.5% agarose gels as described (Bailey and Davidson, 1976). Gels were subsequently stained with ethidium bromide (1 µg/ml in 0.5M $NH_4CH_3CO_2$) to visualize RNA for integrity and loading consistency. RNA was electro transferred to nylon membranes as described for primer extension protocol. Membranes were hybridized with a full-length digoxigenin-labeled antisense probe corresponding to the rat hexokinase cDNA (SEQ ID NO:6) made using Genius 4 RNA Labeling Kit (Boehringer Mannheim, Indianapolis, Ind.) and T7 polymerase.

5. Western Analysis of Hexokinase

Cells were grown to 85%–90% confluence then washed twice with PBS. Cells were harvested into 200 µl of Cell Lysate Solution, containing 10 mM Tris, pH 7.5, 150 mM Nacl, 1 mM EDTA, 0.1% Triton, 1 mM DTT, and protease inhibitors AEBSF, Aprotinin, Leupeptin, each at 1 µg/ml. Cells were sonicated two times each 10–15 seconds on ice. Protein concentration was measured using Bio-Rad Bradford Assay Kit. 10–20 µg proteins were heated at 80° C. for five minutes before loading onto 10% SDS-PAGE gel.

Proteins were then transferred onto PVDF membranes. The membranes were first pre-hybridized with 3% BSA in 10 mM Tris, pH 7.5, 150 mM Nacl solution for a hour at room temperature. Membranes were incubated with Hexokinase I polyclonal antibody (John E. Wilson, Michigan State University) overnight at 4° C. at a 1:2000 dilution.

Goat anti-rabbit IgG conjugate Alkaline Phosphatase was used as the second antibody (Sigma, St. Louis, Mo., No. N-7375) for two to four hours at 1:8000 dilution. The color reaction was performed with substrates b-Naphthyl acid phosphate (Sigma, St. Louis, Mo., No. N-7375) and α-Dianisidine, tetrazotized (Sigma, St. Louis, Mo., No. D-3502) in 0.25 ml of 1M MgCl and membranes were developed in 0.6M sodium borate pH 9.6.

B. Results

1. Clones Expressing the N-terminal Domain of Hexokinase I

Stable G418 resistant clones of RIN 1046-38 transfected with pCB6/intron/HKNterm were screened for expression of the hexokinase N-terminal half by western analysis as described. A protein of 482 amino acids with a predicted molecular weight of 55 Kd was expected.

Five clones were identified with high level expression of a novel protein of this size detected by western analysis using a hexokinase I specific antibody (FIG. 1). Endogenous hexokinase I is present in all five clones as well as in the parental RIN 1046-38 and an independent RIN 1046-38 clone, GK-8, which overexpresses rat glucokinase. There is no crossreactivity of the hexokinase I antibody with any other protein in the 50 to 70 kD range, including rat glucokinase as shown in the GK-8 lane.

All five clones express the hexokinase N-terminal half protein at levels higher than endogenous hexokinase I. Overexpression is expected to be required to dislodge mitochondrial bound endogenous hexokinase.

2. Effects of the N-terminal Domain of Hexokinase I

The effects of overexpression of the hexokinase N-terminal half on endogenous hexokinase in RIN cells are analyzed using the hexokinase enzymatic assay procedure described in detail by Kuwajima et al., (1986) and Becker et al., (1994), each incorporated herein by reference.

Unlike the chimeric hexokinase/glucokinase proteins described in Example III, the hexokinase N-terminal half is enzymatically inactive, but is competent to bind to mitochondria and dislodge endogenous hexokinase. This is expected to have the result of lowering the overall hexokinase activity in RIN cells.

EXAMPLE III

Hexokinase-Glucokinase Chimeras Inhibit Hexokinase Binding to Mitochondria

This example describes chimeric hexokinase-glucokinase enzymes that function to displace hexokinase from mitochondria, thus inhibiting hexokinase, and also provide an active glucokinase enzyme to a cell. These methods and the protein constructs are a second aspect of the dominant negative strategies and proteins of the invention.

A. Materials and Methods

1. Expression Plasmids

A second hexokinase dominant negative strategy involved expressing a Hexokinase I/glucokinase fusion protein. An EcoR1/Nco1 fragment of the hexokinase I cDNA encoding the first 455 amino acids was fused in frame to an Nco1/BamH1 fragment from either pGKL1 or pGKB1 (Quaade et al., 1991) encoding either the entire rat liver glucokinase or rat islet glucokinase open reading frame, respectively.

SEQ ID NO:8 is the resulting 2911 base sequence encoding a 919 amino acid fusion protein consisting of the N terminal 455 amino acids of Hexokinase I and the entire 465 amino acid sequence of liver glucokinase (SEQ ID NO:9). SEQ ID NO:11 is the resulting 2911 base sequence encoding a 919 amino acid fusion protein consisting of the N terminal 455 amino acids of Hexokinase I and the entire 465 amino acid sequence of islet glucokinase (SEQ ID NO:12).

The EcoR1/BamH1 fragment encoding SEQ ID NO:8 and SEQ ID NO:11 was ligated into EcoR1 and BamH1 restriction endonuclease digested pCMV8/IRES/NEO/hGH PolyA, generating pCMV/HK-liverGK/IRES/NEO and pCMV/HK-isletGK/IRES/NEO, respectively (the adenovirus tri-partite leader and hybrid intron of pCMV8/IRES/

NEO/hGH PolyA was removed in the process). The CMV promoter drives transcription of a bicistronic messenger RNA with the HK-GKfusion protein encoded in the upstream open reading frame and the neomycin resistance gene encoded in the downstream open reading frame. Stable transfectants from this plasmid are selected in G418.

2. Western Analysis of Glucokinase

Cells were grown to 85%–90% confluence then washed twice with PBS. Cells were harvested into 200 µl of Cell Lysate Solution, containing 10 mM Tris, pH 7.5, 150 mM Nacl, 1 mM EDTA, 0.1% Triton, 1 mM DTT, and protease inhibitors AEBSF, Aprotinin, Leupeptin, each at 1 µg/ml. Cells were sonicated two times each 10–15 seconds on ice. Protein concentration was measured using Bio-Rad Bradford Assay Kit. 10–20 µg proteins were heated at 80° C. for five minutes before loading onto 10% SDS-PAGE gel.

Proteins were then transferred onto PVDF membranes. The membranes were first pre-hybridized with 3% BSA in 10 mM Tris, pH 7.5, 150 mM Nacl solution for a hour at room temperature. Membranes were incubated with a glucokinase polyclonal antibody raised against a glucokinase/glutathione-S-transferase fusion protein produced and purified from $E.$ $coli$ as recommended by supplier (Pharmacia Biotech, Uppsala, Sweden).

Goat anti-rabbit IgG conjugate Alkaline Phosphatase was used as the second antibody (Sigma, St. Louis, Mo., No. N-7375) for two to four hours at 1:8000 dilution. The color reaction was performed with substrates b-Naphthyl acid phosphate (Sigma, St. Louis, Mo., No. N-7375) and α-Dianisidine, tetrazotized (Sigma, St. Louis, Mo., No. D-3502) in 0.25 ml of 1M MgCl and membranes were developed in 0.6M sodium borate pH 9.6.

Methods of cell culture, transfection and Northern analysis are performed as described in Example II.

B. Results

1. Chimeric Hexokinase/Glucokinases in Transient Transfection

For transient transfection studies, cDNAs encoding chimeric hexokinase/glucokinase proteins consisting of the N-terminal domain of hexokinase I (amino acids 1–455) linked in frame to either the full length liver isoform of glucokinase (HK-liverGK, SEQ ID NO:8) or the islet isoform of glucokinase (HK-isletGK, SEQ ID NO:11) were cloned into pAC.CMVpLpA.

This vector is commonly used for preparation of recombinant adenoviruses, but is also useful for transient expression studies because of its strong CMV promoter and its bacterial origin of replication which allows its propagation in bacteria. pAC.CMV.pLpA and methods for its use have previously been described in detail (Gomez-Foix, et al., 1992; Becker, et al., 1994b, each incorporated herein by reference).

Plasmids containing DNA encoding either intact islet glucokinase, hexokinase I or one of the two hexokinase/glucokinase chimeras were introduced into the human embryonic kidney cell line 293, using $Ca_2PO_4$ co-precipitation. After incubation with the plasmid DNA, cells were cultured for an additional 48 hours. Cells were harvested and crude extracts prepared for assay of glucose phosphorylating activity, using a radioisotopic assay that monitors conversion of U-$^{14}$C glucose to U$^{14}$C glucose-6-phosphate. The extract buffer and assay procedure have previously been described in detail (Kuwajima, et al., 1986; Becker, et al., 1994; each incorporated herein by reference).

Assays were performed at 3 and 20 mM glucose. At the lower glucose concentration, hexokinase activity is maximal while glucokinase activity is very low. At the higher concentration, glucokinase activity is increased to near maximal. The assay was also performed in the presence and absence of 10 mM unlabeled glucose-6-phosphate (G6P). In the presence of G6P, low $K_m$ hexokinases are inhibited, but glucokinase is not.

Figure 2:
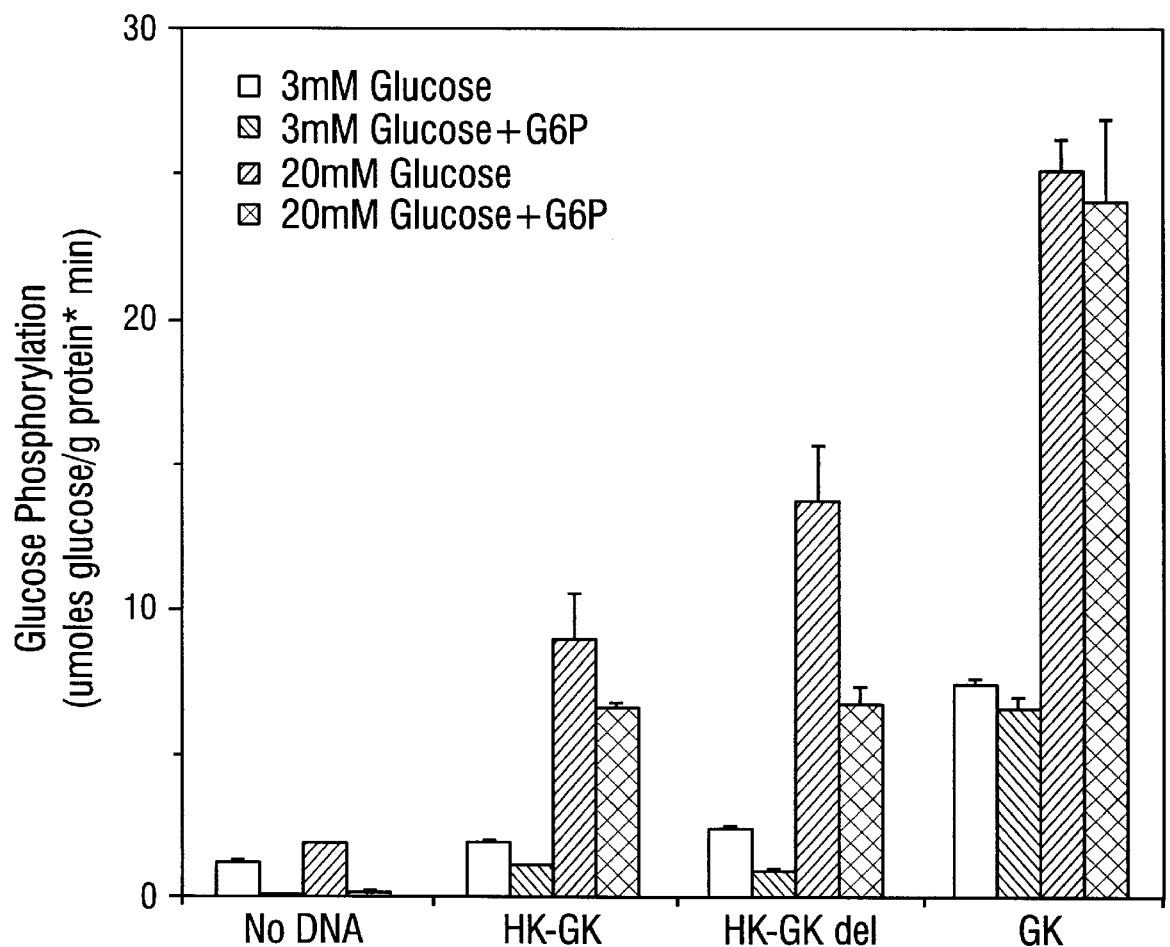
FIG. 2. Measurement of glucose phosphorylating activity in 293 cell extracts which were transiently transfected with chimeric constructs. Assays were done either at 3 or 20 mM glucose in the absence or presence of glucose-6-phosphate (G6P) as indicated. 293 cells were transiently transfected with plasmids expressing the wild type HK-I (HK), HK-isletGK fusion (HK/GK), or wild type islet GK (GK) and compared with nontransfected 293 cells (Parental). Activity is reported as micromoles glucose phosphorylated per gram protein per minute.

As shown in FIG. 2, these assays provide important pieces of information. First, expression of all three expressed enzymes (islet glucokinase, native HKI and HK-isletGK) causes a clear increase in glucose phosphorylating activity in 293 cell extracts relative to untransfected control cells. Second, there is a sharp increase in enzyme activity at 20 mM glucose relative to 3 mM glucose for all three expressed enzymes. Finally, glucose-6-phosphate has no significant effect on the activity measured in the presence of overexpressed native glucokinase.

For the HK-isletGK chimera, G6P inhibits approximately 40% of the activity measured at 20 mM glucose. A similar result was observed for 293 cells transiently transfected with the HK-liverGK chimera, with approximately 20% of the activity measured at 20 mM glucose inhibitable by G6P. While possibly significant, the effects of G6P on the glucose phosphorylating activity of the chimeras is much less than the 90% inhibition typically seen with overexpressed hexokinase I (Becker, et al., 1994; Becker, et al., 1996).

These data demonstrate that the chimeric proteins are active enzymes, and that they behave like glucokinases in two key respects: 1) They have a high apparent $K_m$ for glucose, as evidenced by the sharp increase in activity at 20 mM glucose relative to 3 mM glucose, and 2) they are poorly inhibited by glucose-6-phosphate relative to native hexokinase. These findings predict that expression of the chimeric proteins in cells will displace the native hexokinase from the mitochondria, replacing the low $K_m$ activity with a high $K_m$ activity that is insensitive to G6P inhibition.

2. Stable Expression of Chimeric Hexokinase/Glucokinases

Stable clones of RIN 1046-38 transfected with pCMV/HK-liverGK/IRES/NEO are analyzed for expression of the fusion protein. Western analysis using a glucokinase specific antibody is used to screen individual clones. A novel fusion protein with an expected molecular weight of 105 Kd is produced with the identical enzymatic characteristics of the fusion protein produced transiently in 293 cells. Stable RIN clones expressing the fusion protein are used to determine the dominant negative effects on endogenous hexokinase.

EXAMPLE IV

Glucokinase Expression Inhibits Hexokinase

The present example concerns the demonstration that the expression of glucokinase in mammalian cells inhibits hexokinase.

A. Materials and Methods

Rat glucokinase expression plasmid—a 1763 bp fragment encoding islet/RIN glucokinase cDNA corresponding to bases 180 to 1927 of the published sequence (Hughes et al., 1991) was cloned into pCB7 generating pCB7/GK. Stable transformants of pCB7/GK are selected in 300 ug/ml hygromycin for 14 days without media changes.

The cell culture, stable transfection of cell lines, and Western analyses of glucokinase were performed as described in Examples II and III. Glucokinase activity and glucose usage assays were performed according to standard methodology.

B. Results

RIN 1046-38 cells were transfected with pCB7/GK and stable clones overexpressing rat glucokinase were identified. Individual clones were screened by Western analysis using a glucokinase specific assay. RIN 40-2c represents a pool of clones overexpressing rat glucokinase and was used for subsequent experiments. Glucokinase enzymatic activity increased from 3.94±1.3 U/g in the parental cells to 21.6±2.2 U/g in the glucokinase transfected line.

Figure 3:
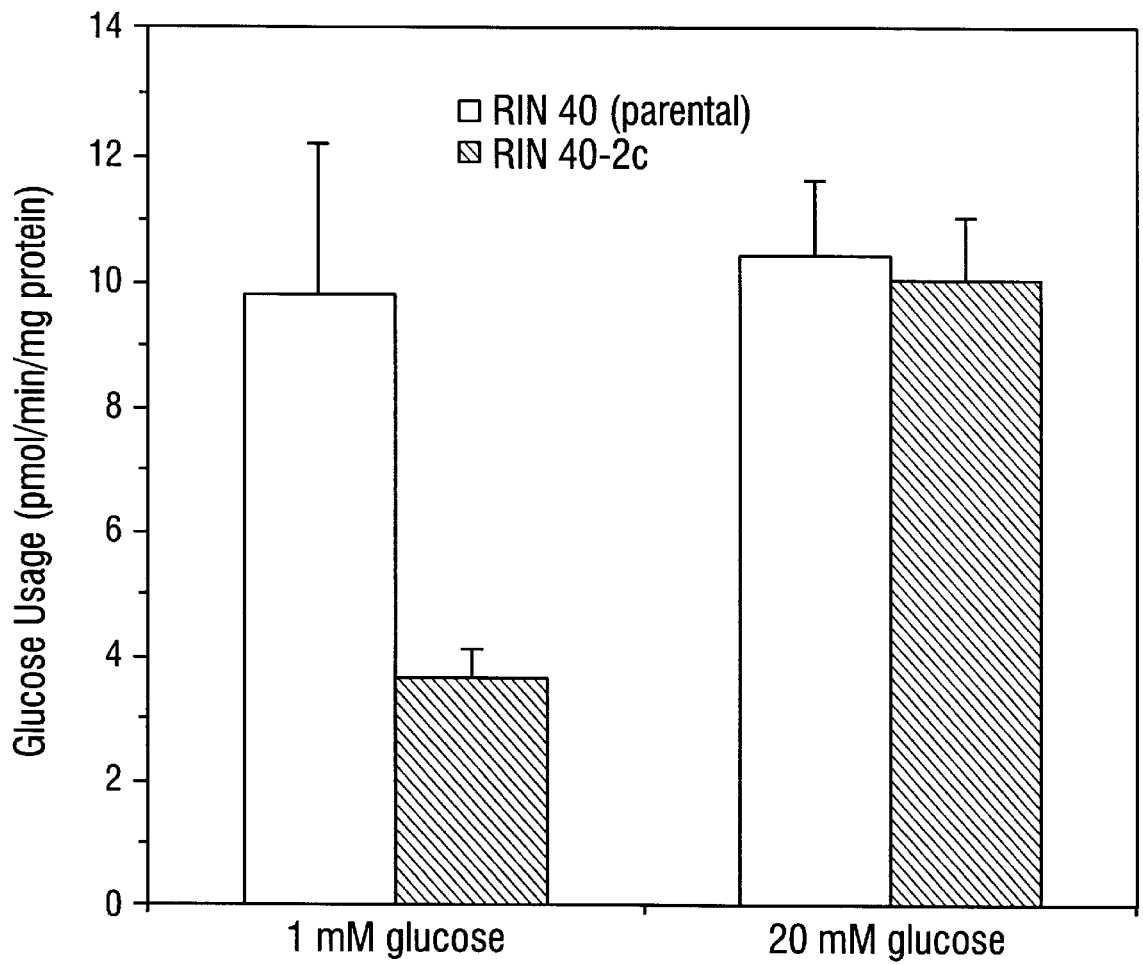
FIG. 3. Glucose usage at low and high glucose concentrations in parental RIN 1046-38 cells compared to RIN cells overexpressing glucokinase (RIN 40-2c).

In the studies of FIG. 3, glucose usage was measured at low (1 mM) and high (20 mM) glucose by administration of [5-$^3$H] glucose to RIN 1046-38 cells of intermediate passage number (passage 40). As would be expected in cells with abundant low $K_m$ hexokinase activity, the rate of glucose usage is similar at the low and high glucose concentrations. Overexpression of glucokinase in RIN 40-2c cells resulted in a 60% decrease in glucose usage at 1 mM glucose relative to the untransfected control cells, while glucose metabolism at 20 mM glucose was unchanged. These results are consistent with the concept that overexpression of glucokinase leads to inhibition of low $K_m$ hexokinase activity in the transfected cells, which in turn reduces the rate of glucose metabolism at low glucose concentrations.

EXAMPLE V

Trehalose-6-Phosphate Synthase Expression Inhibits Hexokinase

The present example concerns the expression of trehalose-6-phosphate synthase in mammalian cells in order to inhibit hexokinase.

A. Materials and Methods

1. Trehalose-6-Phosphate Synthase Expression Plasmid

The open reading frame of the *S. cerevisiae* gene CIF1, encoding trehalose-6-phosphate synthase, was amplified with the polymerase chain reaction from pMB14 (corresponding to bases 249 to 1765 of published sequence, Gonzalez et al., 1992) using oligos (CCCGGA TCCCA-CATACAGACTTATT; SEQ ID NO:28 and CGGGATCCT-CAGTTTTTGGTGGCAGAGG; SEQ ID NO:29. The resulting 1534 base fragment (SEQ ID NO:1) was restricted with BamH1 and ligated into the BamH1 site of pCMV8/IRES/NEO/hGH PolyA generating pCMV8/TPS/IRES/NEO.

The CMV promoter drives transcription of a bicistronic messenger RNA with yeast trehalose-6-phosphate synthase encoded in the upstream open reading frame (SEQ ID NO:2) and the neomycin resistance gene encoded in the downstream open reading frame. Stable transfectants from this plasmid are selected in G418. Alternatively, the 1434 base BamH1 fragment was ligated into the BamH1 site of pCB6/intron, generating pCB6/intron/TPS. Stable transfectants from this plasmid are again selected in G418.

2. Northern Analysis

Northern analysis of trehalose-6-phosphate synthase transcripts in cell lines was performed as described in Example II above for hexokinase message detection. Filters were hybridized with a full-length digoxigenin-labeled antisense probe corresponding to yeast trehalose-6-phosphate synthase (SEQ ID NO:1) made using Genius 4 RNA Labeling Kit (Boehringer Mannheim, Indianapolis, Ind.) and T7 polymerase.

Cell culture and stable transfection of cell lines were performed as described above in Example II.

EXAMPLE VI

Hexokinase Ribozymes Inhibit Hexokinase

This example relates to the use of hexokinase-specific ribozymes for inhibiting hexokinase.

A. Materials and Methods

1. Hexokinase Ribozyme Expression Plasmids

Three separate ribozyme constructs were made directed at target sequences of rat Hexokinase I and/or rat Hexokinase II. The first ribozyme is encoded by oligos 1 and 2 (CTAGACTCCATGCTCTGATGAGTCCGTGAGGAC GAAACGTTCTGGTTCG; SEQ ID NO:29 and GATC-CGAACCAGAACGTTTCGTCCTCACG-GACTCATCAGAGCATGGAGT; SEQ ID NO:30 Bases 3 through 14 of oligo 1 are complimentary to bases 417 to 407 of the published rat hexokinase I messenger RNA (Schwab and Wilson, 1989) while bases 37 to 48 of oligo 1 (SEQ ID NO:29) are complimentary to bases 405 to 394 of rat hexokinase I. Bases 15 through 36 of oligo 1 (SEQ ID NO:29) encode a synthetic ribozyme based on the catalytic domain of the satellite RNA of tobacco ringspot virus (Forster and Symons, 1987).

Once this oligo is transcribed, an RNA (SEQ ID NO:3) with the following components is generated: (i) an internal 22 base highly conserved catalytic domain; (ii) capable of base pairing to the specific sequences of rat hexokinase I, 5' and 3' of the catalytic domain; (iii) and catalyzing cleavage of the rat hexokinase message at a defined cleavage site (between bases 406 and 407 of the rat hexokinase I message).

Oligo 1 (SEQ ID NO:29) and oligo 2 (SEQ ID NO:29) are complimentary in their sequence, annealing together to give a double stranded DNA duplex with an Xba1 endonuclease restriction site overhang at one end and a BamH1 endonuclease restriction site overhang at the other end. The annealed oligos are ligated into pCMV8/IRES/NEO/hGH PolyA that has been restricted with Xba1 and BamH1, generating pCMV8/HKR I BO1+2/IRES/NEO.

The second ribozyme is encoded by oligos 3 and 4 (CTAGATCATGGTCCCCTGATGAGTCCGTGAGGA CGAAACTGTGTCATG; SEQ ID NO:31 and GATCCAT-GACACAGTTTCGTCCTCACGGACTCAT-CAGGGGACCATGAT; SEQ ID NO:32). Bases 5 through 15 of oligo 3 are complimentary to bases 736 to 725 of the published rat hexokinase I messenger RNA (Schwab and Wilson, 1989) and are also complimentary to bases 841 to 831 of rat hexokinase II messenger RNA (Thelen and Wilson, 1991). Bases 38 to 47 of oligo 3 (SEQ ID NO:31) are complimentary to bases 723 to 714 of rat hexokinase I and bases 829 to 820 of rat hexokinase II. Bases 16 through 37 of oligo 3 (SEQ ID NO:31) encode the same synthetic ribozyme as oligo 1, above, which is based on the catalytic domain of the satellite RNA of tobacco ringspot virus (Forster and Symons, 1987).

This second ribozyme (SEQ ID NO:4) will catalyze cleavage of the rat hexokinase I message at a between bases 724 and 725 and cleavage of the rat hexokinase II message between bases 830 and 831. As in the above example, oligo 3 (SEQ ID NO:31) and oligo 4 (SEQ ID NO:32) are complimentary in their sequence, annealing together to give a double stranded DNA duplex with an Xba1 endonuclease restriction site overhang at one end and a BamH1 endonuclease restriction site overhang at the other end. The annealed oligos are ligated into pCMV8/IRES/NEO/hGH PolyA that has been restricted with Xba1 and BamH1, generating pCMV8/HKR I BO3+4/IRES/NEO.

The third ribozyme is encoded by oligos 5 and 6 (CTAGAGTTCCTCCAACTGATGAGTCCGTGAGGA CGAAATCCAAGGCCAG; SEQ ID NO:33 and GATC-CTGGCCTTGGATTTCGTCCTCACGGACT-CATCAGTTGGAGGAACT; SEQ ID NO:34. Bases 6 through 15 of oligo 5 are complimentary to bases 1698 to 1689 of the published rat hexokinase I messenger RNA (Schwab and Wilson, 1989 and 1988) and are also complimentary to bases 1804 to 1795 of rat hexokinase II messenger RNA (Thelen and Wilson, 1991). Bases 38 to 48 of oligo 5 (SEQ ID NO:33) are complimentary to bases 1687 to 1677 of rat hexokinase I and bases 1793 to 1783 of rat hexokinase II. Bases 16 through 37 of oligo 5 (SEQ ID NO:33) encode the same synthetic ribozyme as oligo 1, above, which is based on the catalytic domain of the satellite RNA of tobacco ringspot virus (Forster and Symons, 1987).

This third ribozyme (SEQ ID NO:5) will catalyze cleavage of the rat hexokinase I message at a between bases 1688 and 1689 and cleavage of the rat hexokinase II message between bases 1794 and 1795. As in the above example, oligo 5 (SEQ ID NO:33) and oligo 6 (SEQ ID NO:34) are complimentary in their sequence, annealing together to give a double stranded DNA duplex with an Xba1 endonuclease restriction site overhang at one end and a BamH1 endonuclease restriction site overhang at the other end. The annealed oligos are ligated into pCMV8/IRES/NEO/hGH PolyA that has been restricted with Xba1 and BamH1, generating pCMV8/HKRIBO5+6/IRES/NEO.

The three ribozyme expression plasmids utilize the CMV promoter to drive expression of multifunctional messenger RNAs with the ribozyme placed upstream of the open reading frame of the neomycin resistance gene. Stable transfectants from these plasmids are selected using G418.

2. Northern Analysis

Northern analysis of ribozyme/IRES/NEO transcripts in cell lines was performed as described above in Example I using a full-length digoxigenin-labeled antisense probe corresponding to the neomycin resistance gene (control template supplied in Genius 4 Kit, Boehringer Mannheim, Indianapolis, Ind.).

Cell culture and stable transfection of cell lines were performed as described above in Example I.

B. Results

Ribozymes are used to specifically target the downregulation of an endogenous gene product in engineered cell lines. Three ribozymes have been designed with the capacity to anneal to and enzymatically cleave either the hexokinase I and/or hexokinase I message. Enzymatic cleavage is based on the hammerhead ribozyme structure designed into the three constructs (Forster and Symons, 1987).

Efrat et. al. (1994) reported the results of studies in which a ribozyme was designed to target and down regulate glucokinase. The result of glucokinase down regulation was impaired glucose-induced insulin secretion. Higher glucose concentrations than normal were required to elicit insulin secretion. This is the opposite result from that of the present example, where a normal glucose-induced insulin secretion is expected.

The hexokinase ribozyme transgenes are expressed in RIN1046-38 cells as bicistronic messages of approximately 1100 base pairs. The ribozyme is encoded 5' to the internal ribozyme entry site and neomycin resistance gene which ensures that clones resistant to G418 will also express the ribozyme.

Northern analysis using a probe specific for the neomycin resistance gene of RIN 1046-38 cells transfected with pCMV8/HKR I BO1+2/IRES/NEO demonstrates high level expression of the transgene at the expected size in two independent polyclones (EP113/1A and 1B) as compared to parental cells (FIG. 3).

EXAMPLE VII

Hexokinase Inhibition Slows Cell Growth

This example relates to the use of hexokinase inhibition and its effects on cell growth.

A. Materials and Methods

1. Construction of gene replacement vector

Figure 5:
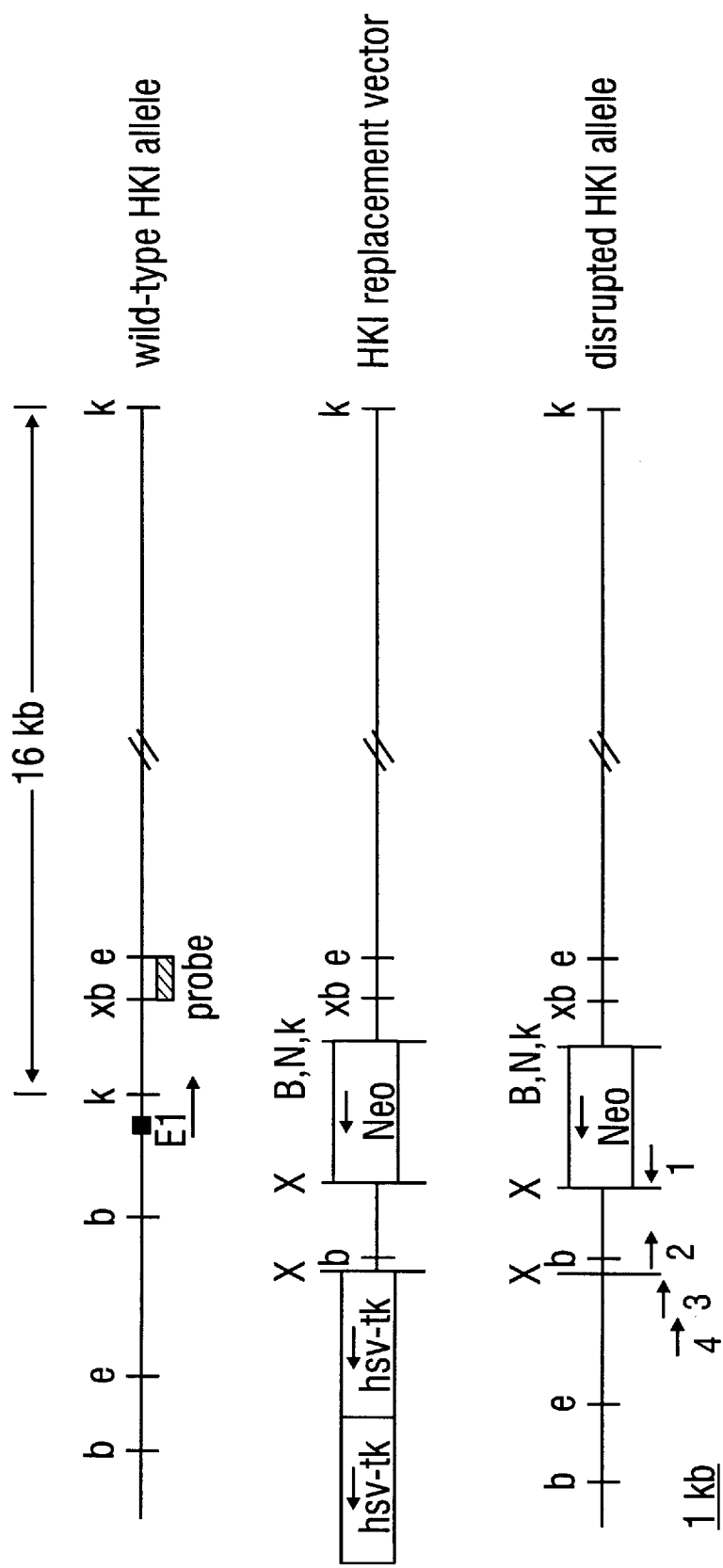
FIG. 5: Map of wild-type HKI allele, vector for replacement, and disrupted HKI allele. Arrows indicate the direction of transcription of hexokinase 1 (E1 for exon 1 shown), neomycin resistance (positive selection gene) and the hsv-tk (negative selection gene). Oligos 1 (SEQ ID NO: 39), 2 (SEQ ID NO: 40), 3 (SEQ ID NO:41) and 4, (SEQ ID NO:42) used in PCR analysis are indicated. Capital bold letters indicate restriction enzyme sites introduced by the knock-out vector and lower case letters indicate sites in the endogenous gene. b, B=BamHI; e=EcoRI; k=KpnI; N=NotI; X=XhoI. The 16 kB KpnI fragment cloned from RIN 1046-38 genomic DNA is indicated as well as the probe used in genomic Southerns (FIG. 6).

A portion of the rat hexokinase I (HKI) gene was subcloned in a lambda Charon 4A (John Wilson, Department of Biochemistry, Michigan State University, East Lansing, Mich.). The 15 kB clone encompassed exon 1, about 0.2 kB of intron 1, and about 14.8 kB of sequence upstream of exon 1. Sequence and maps of this clone aided in the mapping of the HKI gene and in the isolation of homologous isogenic sequences from RIN genomic DNA. The novel 1082 base sequence of the non-transcribed rat HKI genomic DNA as well as the first 170 bases of HKI transcribed DNA (Schwab and Wilson, 1989) is given as SEQ ID NO:43. A plasmid vector providing positive and negative selection was employed as well (Dr. Joachim Herz at the University of Texas Southwestern Medical Center, Department of Molecular Genetics, Dallas, Tex.). pPolIIshort-neobPA-HSV-tk is derived from the pGEM3Zf(+) backbone and contains a neomycin phosphotransferase gene (positive selection) and two tandem copies of herpes simplex virus thymidine kinase gene (HSV-tk) that provide negative selection in the presence of gancyclovir (Ishibashi et al., 1993). pPolIIshort-neobPA-HSV-tk was modified to create pAT9 by creating a unique Not I site five prime of the Neo cassette (FIG. 5). A 873 base pair fragment was amplified from RIN genomic DNA using oligos (TTTCCCCTCGAG CACCGCCCGGAACAGTACC, SEQ ID NO:36 and GTTGCGCCTCGAGCATGCTGACGGTGG GGG, SEQ ID NO:37) to provide a short arm of homology to the HKI gene. The sequence extends 5' from the first methionine of exon 1 and is flanked by engineered XhoI sites.

In addition, a 1121 base fragment was amplified from RIN genomic DNA using oligos (GTTGGACTCGAGAGT CACCTAAGGGCCTATG, SEQ ID NO:38 and GTTGCGCCTCGAGCATGCTGACGGTGGGGG, SEQ ID NO:37), providing a longer short arm to serve as a positive control for screening for homologous recombinants by PCR. The 873 and 1121 base pair PCR fragments were restricted with XhoI and subcloned into pAT9 at a unique XhoI site which is flanked by the Neo cassette and the copies of HSV-tk (FIG. 5), generating pAT21 and pAT22 respectively.

Southern blot analysis in RIN 1046-38 genomic DNA with a probe within exon 1 revealed a 16 kB KpnI fragment. This fragment was enriched by sucrose density ultracentrifugation, modified with adapters to create flanking Not I sites, and subcloned into lambda Dash II (Stratagene, La Jolla, Calif). Recombinant phages containing the fragment were isolated by plaque screening. The 16 kB NotI fragment was cloned into the unique Not I site of pAT22 to provide a long arm of homology to the HKI gene (FIG. 5), generating pAT23, the HK1 replacement vector.

2. Cell culture, electroporation, and drug selection

Various cell lines derived from the rat insulinoma RIN 1046-38 line (Clark et al., 1990) were grown in Medium 199 with Earle's salts, containing 11 mM glucose and 5% fetal bovine serum. Exogenous DNA was introduced into the cells by electroporation. RIN cell lines were grown to 50% to 75% confluence, harvested by trypsinization, washed once with phosphate-buffered saline (PBS), and resuspended in PBS for counting. For each electroporation, $1\times10^7$ cells were pelleted by centrifugation at 1000 rpm for 2 minutes and resuspended in 0.4 ml cold Electroporation Buffer (85.5 mM NaCl, 6.1 mM glucose, 2.5 mM KCl, 350 mM $Na_2HPO4$, 10 mM Hepes, pH 7.0). DNA was added to the cell suspension to achieve a final concentration of 50 micrograms per ml. DNA was electroporated into cells in a 2 mm cuvette at 170 volts and 510 microFaradies using an Electro Cell Manipulator 600 (BTX, Inc., San Diego, Calif.) Cells were plated in non-selective medium and cultured for 2 to 3 days. Medium containing G418 at a final concentration of 500 micrograms per ml was used to select for clones integrated with the neomycin resistance marker. Following positive selection in G418, gancyclovir at a final concentration of 6 μM was used to selectively kill clones expressing HSV-tk. Gancyclovir was applied for 3 days; cells were then maintained in medium containing G418.

3. PCR assay for targeted recombinants

Following positive selection in G418 and negative selection in gancyclovir, clones were grown until visible by the naked eye. Individual colonies were picked, dispersed in trypsin, and divided between duplicate cultures in 96-well plates. Following 10 to 15 days in culture, cells of one duplicate were rinsed in PBS and lysed by incubation at 37° C. for 8 to 12 hours in fifty microliters of Lysis Buffer (16.6 mM ammonium sulfate, 67 mM Tris-HCl, 6.7 mM $MgCl_2$, 5.0 mM 2-mercaptoethanol, 6.7 μM EDTA, 1.7 μM SDS, 50 μg/ml proteinase K, pH 8.8), (Willnow and Herz, 1994). Five microliters of lysate were used as a template in a twenty-five microliter polymerase chain reaction (PCR™) in 16.6 mM ammonium sulfate, 67 mM Tris-HCl, 6.7 mM MgCl2, 5.0 mM 2-mercaptoethanol, 6.7 μM EDTA, 1 mM each dNTP, 80 μg/ml BSA, 0.8 μg/ml of each primer, and 2.5 units Taq DNA polymerase. The amplification program consisted of 92° C., 40 seconds, 57° C. 40 seconds, 75° C., 1 minute (40 cycles) and a final extension for 5 minutes at 75° C. The oligonucleotides used to amplify disrupted HKI included a primer in the 3' end of the Neo cassette (5'GATTGGGAAGACAATAGCAGGCATGC3' SEQ ID NO:39, primer 1, FIG. 5 Ishibashi et al., 1993) and a primer in the HKI gene upstream of the putative recombination site (5'AGTCGCCTCTGCATGTCTGAGTTC3' SEQ ID NO:40, primer 3, FIG. 5). The plasmid pAT22, containing the longer short arm of homology, served as a positive control in this PCR™ reaction. A second control PCR reaction was also included using primer 1 and a primer in the HK1 gene downstream of the recombination site (5'CTTGAGCTCTTACATGGTGTCACG3' SEQ ID NO:41, primer 2, FIG. 5). This control PCR™ reaction should detect both homologous and random integrants of the HK1 replacement vector. Recombinants detected in the first screen were confirmed in a second PCR™ reaction for which no positive control plasmid exists. The absence of such a control negates the possibility of a false positive due to contamination. The primers in this secondary screen were primer 1 (SEQ ID NO:39) and primer 4 (5'TCCCCAGGCGTGGGGTAGAAG3' SEQ ID NO:42), an oligonucleotide upstream of the recombination site in the HKI gene (FIG. 5). PCR™ products analyzed either by gel electrophoresis or a slot blot assay. For electrophoresis, reaction products were fractionated in 1% agarose gels in Tris-borate/EDTA buffer (9 mM Tris-borate, 0.2 mM EDTA). DNA was visualized by staining in ethidium bromide. For slot-blots, reaction products were denatured in 0.5N NaOH, 1.5M NaCl, neutralized in 1.0M Tris-HCl, pH 7.5, 1.5M NaCl, and transfer to a nylon membrane using a 96-well blot apparatus (Scheichller and Schuell, Keene, N. H.). DNA was cross-linked to the membrane and HKI amplified products were detected by hybridization with $^{32}$P-labelled oligonucleotides complementary to HKI and internal to primers used in the amplification reaction. Positive clones were replated in 96-well dishes to obtain densities of one cell per well. These clones were allowed to grow and assayed by PCR™ with the primers described above. This cycle of dilution cloning was repeated until all clones of a plating were positive in the assay.

4. Genomic Southern analysis

RIN clones that were positive by PCR™ for an disrupted allele of HKI were assayed by genomic Southern. Genomic DNA was isolated using reagents and protocols of the QIAamp Blood Kit (catalog number 29104, Qiagen, Inc., Chatsworth Calif.) Five to ten micrograms of DNA were digested with enzymes as indicated and fractionated through 0.8% agarose gels using TEAN buffer (0.04M Tris-HCl, 0.025M sodium acetate, 0.018M NaCl, 25 mM EDTA, pH 8.15). Electrophoresis was conducted for 12 to 16 hours at 25 to 35 volts with recirculation of the buffer from the positive to the negative electrode. DNA was visualized by staining with ethidium bromide. DNA in the gel was denatured for 30 minutes in 0.5N NaOH, 1.5M NaCl. Following neutralization in 1M Tris-HCl, pH 7.5, 1M NaCl for 30 minutes, DNA was transferred to a nylon membrane (Hybond-N+, Amersham) in 10× SSC (1×: 0.15M NaCl, 0.015M sodium citrate) and cross-linked to the membrane by ultraviolet radiation (UV Stratalinker 2400, Stratagene, Inc.). Radiolabelled probes ($^{32}$P) for hybridization to and detection of genomic fragments were synthesized as directed using the rediprime Random Primer Labelling Kit (RPN 1633, Amersham Life Sciences). Membranes were prehybridized and hybridized in Rapid-hyb Buffer (NIF939, Amersham Life Sciences). All incubations and washes were performed in a Micro-4 Hybridisation Oven (Hybaid Limited). Membranes were exposed to X-OMAT, AR5 film (Kodak) for periods of time as indicated.

B. Results

Prior to construction of a gene replacement vector, a comparison was made of the copy number of HKI alleles in rat versus RIN genomic DNA. DNA was digested with XbaI, Southern blotted, and probed with a radiolabelled fragment from intron 1 of the HKI gene. Autoradiography revealed equivalent signals derived from the rat and RIN HKI gene fragments. Presumably, these signals correspond to diploidy of the HKI gene in both the rat and RIN genomes. This conclusion is supported by data that show RIN-derived cell lines to have maintained a diploid state in their chromosomes. Karyotype analysis of RIN 1046-38 showed a distribution 35 to 40 chromosomes with the normal rat compliment being 42 chromosomes.

The HKI replacement vector (FIG. 5) was transfected into RIN cells in three separate electroporations (EP): EP81, EP86, EP95. These electroporations differ from each other in their temporal distributions, the identity of the parental cell line, and the number of clones screened from each (Table 3). EP81 was derived from a low passage RIN 1046-38 cell line. Of the 500 colonies screened, none were positive for disruption of an HKI allele. RIN-52/17, a RIN 1046-38 derived clone, was the parental line in EP86. One positive clone was detected a screen of about 970 colonies. RIN-52/9, a cell line that expresses high levels of rat glucokinase and is resistant to hygromycin, was used as a parental line in EP95. About 3200 clones were screened by PCR for the precense of a disrupted HKI allele. None were positive.

Potentially, the loss of an HKI allele could result in a growth disadvantage and thereby lead to a lower frequency of detecting HKI gene replacement events. To negate a potential metabolic disadvantage conferred by loss of HKI activity, efforts were made to create parental cell lines that overexpress rat glucokinase. Such parental lines could potentially serve two functions—first, to prevent metabolic stress should phosphorylation of glucose became rate-limiting in transformed cell lines with diminished HKI activity; and second, to restore a high $K_m$ glucose-phosphorylating activity to the RIN lines to shift glucose-responsive insulin secretion towards a more physiological range. RIN-52/17, the parental cell line in EP86, had previously been electroporated with a plasmid conferring hygromycin resistance and containing a copy of the rat glucokinase (GK) cDNA. RIN-52/17 was hygromycin resistant and was thought to express moderate levels of glucokinase from the transgene. Subsequent data confirmed resistance to hygromycin, but disproved expression of GK from the transgene (Table 3). About 1000 individual clones were screened from EP86. From this screen one clone, 86/X4, was positive by PCR™. Clone 86/X4 was initially identified by amplification with primer 1 and primer 3. The molecular weight of the amplified product was equal to that derived from the plasmid control. Confirmation of this clone as containing a disrupted HKI allele was obtained by amplification with primer 1 and primer 4. No plasmid control exists for this PCR reaction; therefore, the product is not the result of contamination.

TABLE 3

Electroporation (EP) of RIN Cell Lines with a HK1 Replacement Vector

| EP | Parental line | DrugR, Parental | Transgene | Clones screened | + by PCR ™ |
|----|---------------|-----------------|-----------|-----------------|------------|
| 81 | RIN 1047-38   | (−)             | (−)       | 500             | 0          |
| 86 | RIN 5217      | HygroR          | (−)       | 970             | 1          |
| 95 | RIN 52-9      | HygroR          | rat GK    | 3200            | 0          |

Targeted disruption of HK1 was attempted in various RIN lines, in the absence of presence of high levels of expression of rat glucokinase (GK) from a transgene. Cells expressing the transgene were first selected for resistance to hygromycin (HygroR) and then assayed by Western blotting for expression of exogenous rat GK.

The original positive culture of 86/X4 was passaged several times prior to dilutional plating for assessing the purity of the clonal population. 197 individual colonies were cultured in 96-well plates, allowed to grow to 50–70% confluence, trypsinized, and split into duplicate cultures. Cells from one set of cultures were lysed and screened by PCR using primers 1 and 3 and then reaction products were analyzed by a slot assay. Two clones were confirmed as containing a disrupted allele of HKI. This result suggests two things. First, the original culture that was identified as 86/X4 was a polyclonal rather than a monoclonal population. Second, the clone containing the disrupted allele of HKI seems to have a growth disadvantage compared to other cells in the population. This latter possibility is supported by observations of the growth rates of the purified HKI replacement clone. The pure 86/X4 grows significantly slower (about one-half as fast) than clones randomly integrated with the replacement vector.

Figure 6:
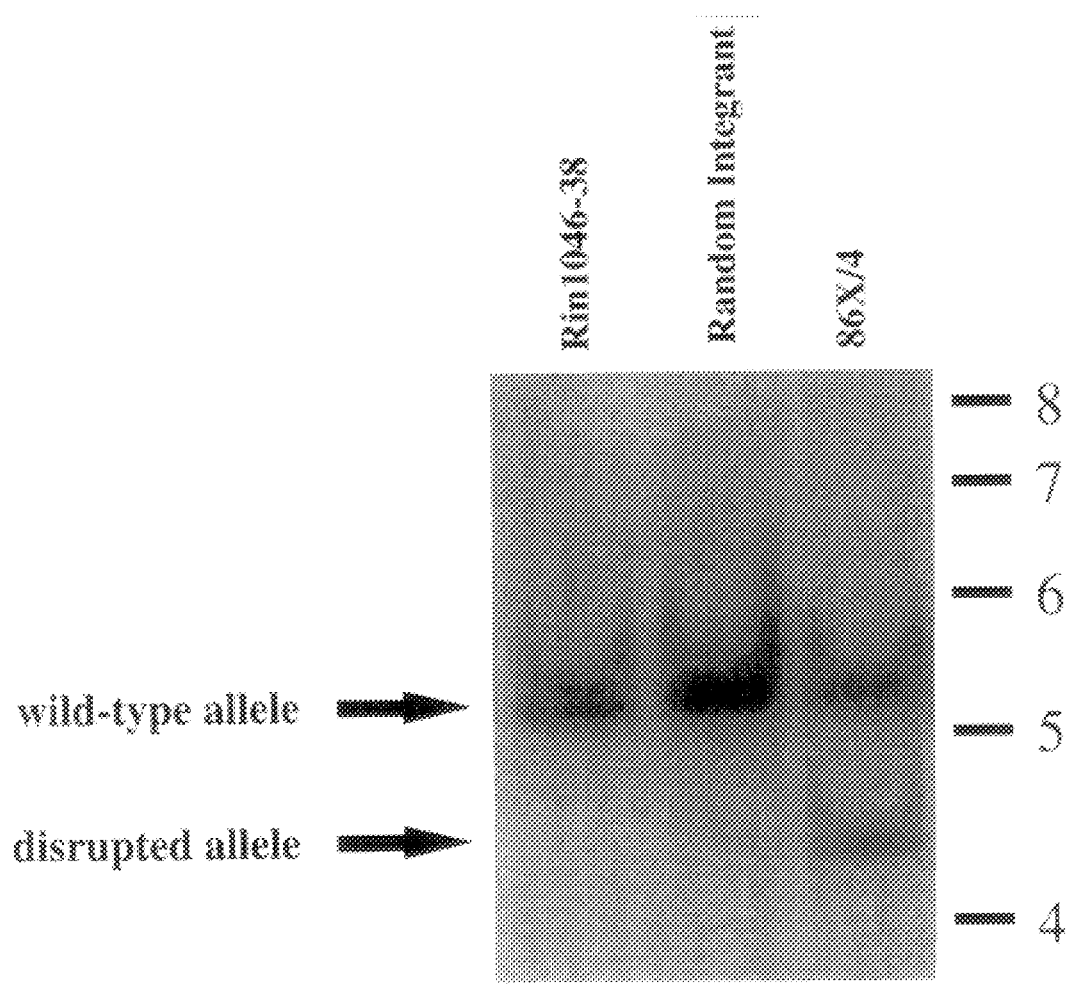
FIG. 6: Genomic Southern confirming hexokinase I gene disruption. The probe (hatched rectangle, FIG. 5) is a 1 kB Pst I fragment upstream of the recombination site. Genomic DNA was digested with NotI and EcoRI. The DNA in each lane is as follows: first lane, RIN 1046-38; second lane, PIN-52/17 containing a randomly integrated HKI replacement vector; and lane 3, RIN-52/17 containing a disrupted allele of the HKI gene (clone 86/X4).

Additional data verifying the identity of clone 86/X4 were derived by analysis of genomic DNA by Southern blotting (FIG. 6). DNA was digested with EcoRI and NotI, blotted, and hybridized with a probe upstream of the recombination site (hatched rectangle, FIG. 5). DNA from RIN 1046-38 cells (lane 1) and from RIN-52/17 randomly integrated with pAT23 (lane 2) produce a predicted signal of about 5.5 kB in the autoradiograph. This signal corresponds to a homozygous, wild-type HKI gene. Clone 86/X4 produces two autoradiographic signals in the genomic Southern (lane 3): a 5.5 kB signal corresponding to a wild-type allele and an additional signal (about 4.6 kB), indicative of a HKI allele that has homologously recombined with the replacement vector.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adams et al., "Porin interaction with hexokinase and glycerol kinase: Metabolic microcompartmentation at the outer mitochondrial membrane," *Bioch. Med. Met. Biol.*, 45:271–291, 1991.

Altman et al., *Diabetes*, 35:625–633, 1986.

Anderson et al., "Cloning, structure, and expression of the mitochondrial cytochrome P-450 sterol 26-hydroxylase, a bile acid biosynthetic enzyme," *J. Biol. Chem.*, 264:8222–8229, 1989.

Arora, et al. *J. B. C.* 268:18259–18266, 1993.

Baijal, et al.,*J. E. Arch. Bioch. Biophys.* 298:271–278, 1992.

Bailey and Davidson, "Methylmercury as a reversible denaturing agent for agarose gel electrophoresis," *Anal. Biochem.*, 70:75–85, 1976.

Becker et al., "Differential effects of overexpressed glucokinase and hexokinase I in isolated islets: Evidence for functional segregation of the high and low $K_m$ enzymes," *J. Biol. Chem.*, 271:390–394, 1996.

Becker et al., "Overexpression of hexokinase I in isolated islets of langerhans via recombinant adenovirus," *J. Biol. Chem.*, 269:21234–21238, 1994a.

Becker et al., "Use of recombinant adenovirus for metabolic engineering of mammalian cells," *Methods in Cell Biology*, 43:161–189, Roth, M., Ed. New York, Academic Press, 1994b.

Bell, et al., "Characterization of the 56-kDa subunit of yeast trehalose-6-phosphate synthase and cloning of its gene reveal its identity with the product of CIF1, a regulator of carbon catabolite inactivation," *Eru. J. Biochem.*, 209:951–959, 1992.

Berzal-Herranz, A. et al., *Genes and Devel.*, 6:129–134, 1992.

Blazquez et al., "Treheolose-6-phosphate, a new regulator of yeast glycolysis that inhibits hexokinases," *FEBS Lett.* 329:51–54, 1993.

Brewer, "Cytomegalovirus plasmid vectors for permanent lines of polarized epithelial cells," In: *Methods in Cell Biology*, 43:233–245, Roth, M., Ed. New York, Academic Press, 1994.

Burch, et al., "Adaptation of glycolytic enzymes. Glucose use and insulin release during fasting and refeeding." *Diabetes* 30:923–928.

Chowrira, B. H. et al., *Biochemistry*, 32, 1088–1095.

Chowrira, B. H. et al., "In vitro and in vivo comparison of hammerhead, hairpin, and hepatitis delta virus self-processing ribozyme cassetyes." *J. B. C.*, 269:25856–25864, 1994.

Clark et al., "Modulation of glucose-induced insulin secretion from a rat clonal beta-cell line," *Endocrinology*, 127:2779–2788, 1990.

Clark et al., "Islet cell culture in defined serum-free medium," *Endocrinology*, 126:1895–1903, 1990.

Cone, et al., *Proc. Natl. Acad. Sci. U.S.A.*, 81:6349–6353, 1984.

Danos, et al., *Proc. Natl. Acad. Sci. U.S.A.*, 85:6460–6464, 1988.

Epstein, et al., "Expression of yeast hexokinase in pancreatic beta-cells of transgenic mice reduces blood glucose, enhances insulin secretion, and decreases diabetes," *Proc. Natl. Acad. Sci. USA*, 89:12038–12042, 1992.

Efrat, et al., "Murine insulinoma cell line with normal glucose-regulated insulin secretion," *Diabetes*, 42:901–907, 1993.

Efrat, et al., "Ribozyme-mediated attenuation of pancreatic Beta-cell glucokinase expression in transgenic mice results in impaired glucose-induced insulin secretion," *Proc. Natl. Acad. Sci. USA*, 91:2051–2055, 1994.

Efrat et al., "Conditional transformation of a pancreatic beta cell line derived from transgenic mice expressing a tetracycline-regulated oncogene," *Proc. Natl. Acac. Sci., USA*, 92: 3576–3580, 1995.

Fanciulli et al., Glycolysis and growth rate in normal and in hexokinase-transfected NIH-3T3 cells," *Oncology Res.*, 6(9): 405–409, 1994.

Felgner and Wilson, *Arch. Bioch. Biophys.*, 182:282–294, 1977.

Ferber et al., "GLUT-2 gene transfer into insulinoma cells confers both low and high affinity glucose-stimulated insulin release," *J. Biol. Chem.*, 269:11523–11529, 1994.

Fiek et al., "Evidence for identity between hexokinase-binding protein and the mitochondrial porin in the outer membrane of rat liver mitochondria," *Biochem. Biophys. Acta*, 688:429–440, 1982.

Forster & Symons, "Self-cleavage of plus and minus RNAs of a virusoid and a structural model for the active sites," *Cell*, 49:211–220, 1987.

Fritschy et al., *Diabetes*, 40:37, 1991.

Frougel et al., "Familial hyperglycemia due to mutations in glucokinase," *N. Engl. J. Med.*, 328:105–112, 1993.

Gazdar et al., "Continuous, clonal, insulin- and somatostatin-secreting cell lines established from a transplantable rat islet cell tumor," *Proc. Natl. Acad. Sci. USA*, 77:3519–3523, 1980.

Gelb et al., "Targeting of hexokinase 1 to liver the hepatoma mitochondria," *Proc. Natl. Acad. Sci. USA*, 89:202–206, January, 1992.

Gerlach et al., "Construction of a plant disease resistance gene from the satellite RNA of tobacco rinspot virus," *Nature (London)*, 328:802–805, 1987.

Gomez-Foix et al., "Adenovirus-mediated transfer of the muscle glycogen phosphorylase gene into hepatocytes confers altered regulation of glycogen metabolism," *J. Biol. Chem.*, 267:25129–25134, 1992.

Gonzalez et al., "Molecular cloning of CIF1, a yeast gene necessary for growth on glucose," *Yeast*, 8:183–192, 1992.

Haseloff, T. and Gerlach, W. L. "Simple RNA enzymes with new and highly specific endoribonuclease activities." *Nature*, 334:585–591, 1988.

Hosokawa, et al., "Upregulated hexokinase activity in isolated islets from diabetic 90% pancreatectomized rats." *Diabetes* 44:1328–1333, 1995.

Hughes et al., "Engineering of Glucose-stimulated Insulin Secretion and Biosynthesis in Non-islet Cells", *Proc. Natl. Acad. Sci. USA*, 89:688–692, 1992.

Hughes et al., "Transfection of AtT-20$_{ins}$ Cells with GLUT-2 but Not GLUT-1 Confers Glucose-stimulated Insulin Secretion", *The Journal of Biological Chemistry*, 268:15205–15212, 1993.

Kabir and Wilson, "Mitochondrial Hexokinase in Brain: Coexistence of Forms Differing in Sensitivity to Solubilization by Glucose-6-Phosphate on the Same Mitochondria," *Arch. Biochem. Biophys.*, 310(2):410–416, 1994.

Kaufman and Sharp, "Construction of a modular dihydrofolate reductase cDNA gene: Analysis of signals utilized for efficient expression," *Mol. Cell. Biology*, 2:1304–1319, 1982.

Knaack et al., "Clonal Insulinoma Cell Line That Stably Maintains Correct Glucose Responsiveness," *Diabetes*, 43:1413–1417, 1994.

Kuwajima et al., "The glucose-phosphorylating capacity of liver as measured by three independent assays," *J. Biol. Chem.*, 261:8849–8853, 1986.

Lacy et al., *Science*, 254:1782–1784, 1991.

Liang, et al. "Glucose regulates glucokinase activity in cultured islets from rat pancreas." *J. Biol. Chem.* 265:16863–16866, 1990.

Lieber, A. and Strauss, M. "Selection of efficient cleavage sites in target RNAs by using a ribozyme expression library." *Mol. Cell. Biol.*, 15: 540–551, 1995.

Linden et al., "Pore protein and the hexokinase-binding protein from the outer membrane of rat liver mitochondria are identical," *FEBS Lett.*, 141:189–192, 1982.

Madsen, et al., *Proc. Natl. Acad. Sci. U.S.A.*, 85:6652–6656, 1988.

Matchinsky, "Glucokinase as a sensor and metabolic signal generator in pancreatic Beta-cells and hepatocytes," *Diabetes*, 39:647–652, 1990.

Mathupala et al., "Glucose catabolism in cancer cells," *J. Biol. Chem.*, 270:16918–16925, 1995.

Meglasson and Matschinsky, "Pancreatic islet glucose metabolism and regulation of insulin secretion," *Diabetes Metab. Rev.*, 2:163–214, 1986.

Newgard and McGarry, "Metabolic coupling factors in pancreatic Beta-cell signal transduction," *Annu. Rev. Biochem.*, 64:689–719, 1995.

Newgard et al., "Glucokinase and glucose transporter expression in liver and islets: implications for control of glucose homeostasis," *Biochem. Soc. Trans.*, 18:851–853, 1990.

O'Shea and Sun, *Diabetes*, 35:943–946, 1986.

Palukaitis, P. et al., "Characterization of a viroid associated with avacado sunblotch disease." *Virology*, 99:145–151, 1979.

Perriman, R. et al., "Extended target-site specificity for a hammerhead ribozyme." *Gene*, 113:157–163, 1992.

Polakis and Wilson, "An intact N-terminal sequence is critical for binding rat brain hexokinase to mitochondria," *Arch. Biochem. Biophys.*, 236:328–337, 1985.

Prody, G. A. et al., "Autolytic processing of dimeric plant virus satellite RNA." *Science*, 231, 1577–1580, 1986.

Radvanyi et al., "Pancreatic beta bells cultured from individual preneoplastic foci in a multistage tumorigenesis pathway: a potentially general technique for isolating physiologically representative cell lines," *Molec. and Cell. Biol.*, 13(7): 4223–4232, 1993.

Sarver, et al, "Ribozymes as potential anti-HIV-1 therapeutic agents," Science, 247:1222–1225, 1990.

Sato et al., *Proc. Natl. Acad. Sci U.S.A.*, 48:1184–1190, 1962.

Schwab and Wilson, "Complete amino acid sequence of rat brain hexokinase, deduced from the cloned cDNA, and proposed structure of a mammalian hexokinase," *Proc. Natl. Acad. Sci. USA*, 86:2563–2567, 1989.

Schwab and Wilson, "Complete amino acid sequence of the Type III isozyme of rat hexokinase, deduced from the cloned cDNA," *Arch. Biochem. Biophys.*, 285:365–370, 1991.

Smith and Wilson, *Arch. Bioch. Biophys.*, 287:359–366, 1991.

Stossel, T., in *The Molecular Basis of Blood Diseases*, Chapter 14, pp. 499–533, W. B. Saunders Co. Philadelphia, Pa., 1987.

Sullivan et al., *Science*, 252:718–721, 1991.

Symons, R. H., "Avacado sunblotch viroid: primary sequence and proposed secondary structure." *N. A. R.*, 9:6527–6537, 1981.

Symons, R. H. "Small catalytic RNAs." *Annu. Rev. Biochem.*, 61:641–671, 1992.

Thelan and Wilson, "Complete amino acid sequence of the Type II isozyme of rat hexokinase, deduced from the cloned cDNA:Comparison with a hexokinase from Novikoff ascites tumor," *Arch. Biochem. Biophys.*, 286:645–651, 1991.

Thompson, J. D. et al., "Ribozymes in gene therapy." *Nature Medicine*, 1:277–278, 1995.

Ting and Lee, "Human gene encoding the 78,000-Dalton glucose-regulated protein and its pseudo gene: Structure, conservation, and regulation," *DNA*, 7:275–286, 1988.

White and Wilson, *Arch. Bioch. Biophys.*, 259:402–411, 1987.

White and Wilson, *Arch. Bioch. Biophys.*, 277:26–34, 1990.

Wilson, "Brain hexokinase: A proposed relation between soluble-particulate distribution and activity in vivo," *J. Biol. Chem.*, 243:3640–3647, 1968.

Wilson, "Ligand induced confirmations of rat brain hexokinase: Effects of glucose-6-phosphate and inorganic phosphate," *Arch. Biochem. Biophys.*, 159:543–549, 1973.

Wilson, "Regulation of mammalian hexokinase activity," *In: Regulation of Carbohydrate Metabolism*, Beitner, R. (Ed.) Vol. 1, CRC, Boca Raton, 45–81, 1985.

Wilson, "Hexokinases," *In: Reviews of Physiology, Biochemistry and Pharmacology*, Pette, D. (Ed.), 126:65–174, 1994.

Xie and Wilson, "Rat brain hexokinase: the hydrophobic N-terminus of the mitochondrially bound enzyme is inserted in the lipid bilayer," *Arch. Biochem. Biophys.*, 267:803–810, 1988.

Yuan, Y. and Altman, S. "Selection of guide sequences that direct efficient cleavage of mRNA by human ribonuclease P." *Science*, 263:1269–1273, 1994.

Yuan, Y. et al., "Targeted cleavage of mRNA by human RNase P." *P. N. A. S.*, 89:8006–8010, 1992.

U.S. Pat. No. 4,892,538
U.S. Pat. No. 5,011,472
U.S. Pat. No. 5,399,346
WO 89/01967
WO 90/02580
WO 90/15637
WO 91/10425
WO 91/10470

What is claimed is:

1. An engineered cell that secretes insulin in response to glucose, the cell comprising a recombinant gene that expresses a competitive inhibitor of a low $K_m$ hexokinase enzyme, wherein the inhibitor lacks low $K_m$ hexokinase activity and comprises a mitochondrial binding region from the N-terminal domain of a low $K_m$ hexokinase, said inhibitor being present in an amount effective to substantially displace native low $K_m$ hexokinase from mitochrondria thereby reducing the low $K_m$ hexokinase activity of said cell.

2. The cell of claim 1, wherein said inhibitor is introduced into said cell by means of a recombinant vector comprising a promoter operatively linked to the recombinant gene that encodes the inhibitor, the promoter expressing said inhibitor in said cell.

3. The cell of claim 1, wherein said inhibitor reduces the hexokinase I activity of said cell.

4. The cell of claim 1, wherein said inhibitor reduces the hexokinase II activity of said cell.

5. The cell of claim 1, wherein said cell has reduced low $K_m$ hexokinase activity relative to a parent cell from which it was prepared.

6. The cell of claim 1, wherein said low $K_m$ hexokinase activity is reduced to an amount effective to allow insulin secretion in response to an extracellular glucose concentration of between about 1 mM and about 20 mM.

7. The cell of claim 1, wherein said inhibitor comprises a mitochondrial binding region from the N-terminal domain of hexokinase I.

8. The cell of claim 1, wherein said inhibitor comprises a mitochondrial binding region from the N-terminal domain of hexokinase II.

9. The cell of claim 1, wherein said inhibitor comprises a mitochondrial binding region that includes a contiguous amino acid sequence from SEQ ID NO:7 or a contiguous amino acid sequence from between about position 1 to about position 455 of SEQ ID NO:16.

10. The cell of claim 9, wherein said recombinant gene includes a contiguous nucleic acid sequence from SEQ ID NO:6 or a contiguous nucleic acid sequence from between about position 1 to about position 1563 of SEQ ID No:15.

11. The cell of claim 1, wherein said inhibitor is a truncated low $K_m$ hexokinase which is the N-terminal domain of a low $K_m$ hexokinase.

12. The cell of claim 11, wherein said inhibitor is a truncated low $K_m$ hexokinase which is the N-terminal domain of hexokinase I.

13. The cell of claim 11, wherein said inhibitor is a truncated low $K_m$ hexokinase which is the N-terminal domain of hexokinase II.

14. The cell of claim 11, wherein said inhibitor is a truncated low $K_m$ hexokinase which is the amino acid sequence of SEQ ID NO:7 or the amino acid sequence from between about position 1 to about position 455 of SEQ ID NO:16.

15. The cell of claim 14, wherein said recombinant gene has the nucleic acid sequence from SEQ ID NO:6 or the nucleic acid sequence from between about position 1 to about position 1563 of SEQ ID NO:15.

16. The cell of claim 1, wherein said inhibitor is a hexokinase-glucokinase chimera that comprises a mitochondrial binding region from the N-terminal domain of a low $K_m$ hexokinase operatively linked to at least the catalytic domain of hexokinase IV.

17. The cell of claim 16, wherein said inhibitor is a hexokinase-glucokinase chimera that comprises a low $K_m$ hexokinase mitochondrial binding region operatively linked to a catalytic hexokinase IV domain that includes a contiguous amino acid sequence from SEQ ID NO:20 or SEQ ID NO:22.

18. The cell of claim 16, wherein said inhibitor is a hexokinase-glucokinase chimera that comprises a mitochondrial binding region from the N-terminal domain of a low $K_m$ hexokinase operatively linked to hexokinase IV.

19. The cell of claim 18, wherein said inhibitor is a hexokinase-glucokinase chimera that comprises a low $K_m$ hexokinase mitochondrial binding region operatively linked to the hexokinase IV amino acid sequence of SEQ ID NO:20 or SEQ ID NO:22.

20. The cell of claim 19, wherein said recombinant gene includes the contiguous nucleic acid sequence of SEQ ID NO:19 or SEQ ID NO:21.

21. The cell of claim 11, wherein said inhibitor is a hexokinase-glucokinase chimera that comprises the amino acid sequence of SEQ ID NO:9 or SEQ ID NO:12.

22. The cell of claim 21, wherein said recombinant gene includes the contiguous nucleic acid sequence of SEQ ID NO:8 or SEQ ID NO:11.

23. The cell of claim 1, wherein said inhibitor is a low $K_m$ hexokinase enzyme that has been mutated to reduce or eliminate its catalytic activity.

24. The cell of claim 23, wherein said inhibitor is a substantially full length low $K_m$ hexokinase enzyme that has been mutated to reduce or eliminate its catalytic activity.

25. The cell of claim 1, wherein, in addition to provision of the recombinant gene that expresses said inhibitor, the low $K_m$ hexokinase activity of said cell is further reduced by interruption of a low $K_m$ hexokinase gene.

26. The cell of claim 1, wherein, in addition to provision of the recombinant gene that expresses said inhibitor, the low $K_m$ hexokinase activity of said cell is further reduced by inserting into said cell an antisense RNA molecule that is complementary to and binds to a low $K_m$ hexokinase gene or RNA transcript.

27. The cell of claim 1, wherein, in addition to provision of the recombinant gene that expresses said inhibitor, the low $K_m$ hexokinase activity of said cell is further reduced by providing to said cell a trehalose-6-phosphate synthase enzyme that stimulates the production of trehalose-6-phosphate in said cell.

28. The cell of claim 1, wherein, in addition to provision of the recombinant gene that expresses said inhibitor, the low $K_m$ hexokinase activity of said cell is further reduced by providing to said cell a ribozyme specific for an RNA transcript of a low $K_m$ hexokinase gene.

29. The cell of claim 1, wherein, in addition to the recombinant gene that expresses said inhibitor, said cell further comprises a recombinant gene that expresses a selected protein.

30. The cell of claim 1, wherein, in addition to the recombinant gene that expresses said inhibitor, said cell further comprises a recombinant hexokinase IV gene, a recombinant insulin gene or a recombinant GLUT-2 gene introduced into the cell by means of a recombinant vector.

31. The cell of claim 30, wherein said cell further comprises two recombinant genes selected from the group consisting of hexokinase IV, insulin and GLUT-2.

32. The cell of claim 30, wherein said cell further comprises a recombinant hexokinase IV gene, a recombinant insulin gene and a recombinant GLUT-2 gene.

33. The cell of claim 30, further comprising a recombinant hexokinase IV gene.

34. The cell of claim 33, wherein said recombinant hexokinase IV gene is an islet isoform hexokinase IV gene.

35. The cell of claim 30, further comprising a recombinant insulin gene.

36. The cell of claim 30, further comprising a recombinant GLUT-2 gene.

37. The cell of claim 36, wherein said recombinant GLUT-2 gene is an islet isoform GLUT-2 gene.

38. The cell of claim 1, further defined as a cell derived from a cell capable of forming secretory granules.

39. The cell of claim 38, further defined as a cell derived from a neuroendocrine cell.

40. The cell of claim 38, further defined as a cell derived from an AtT-20 cell.

41. The cell of claim 38, further defined as a cell derived from a GH-1 cell or a GH-3 cell.

42. The cell of claim 38, further defined as a cell derived from a pancreatic β cell.

43. The cell of claim 42, further defined as a cell derived from a βTC, HIT or RIN cell.

44. The cell of claim 43, further defined as a cell derived from a RIN cell.

45. The cell of claim 1, wherein said cell secretes recombinant insulin.

46. The cell of claim 11, wherein said cell comprises a glutamic acid decarboxylase gene.

47. The cell of claim 46, wherein, in addition to the recombinant gene that expresses said inhibitor, said cell comprises a recombinant glutamic acid decarboxylase gene.

48. The cell of claim 1, wherein said cell is formulated in a pharmaceutically acceptable medium.

49. The cell of claim 1, wherein said cell is encapsulated in a biocompatible coating.

50. An engineered mammalian cell derived from a cell that forms secretory granules, the cell secreting insulin in response to glucose and comprising a first recombinant gene selected from the group consisting of hexokinase IV, insulin and GLUT-2 and a second recombinant gene that expresses a competitive inhibitor of a low $K_m$ hexokinase enzyme, wherein the inhibitor lacks low $K_m$ hexokinase activity and comprises a mitochondrial binding region from the N-terminal domain of a low $K_m$ hexokinase, said inhibitor being present in an amount effective to substantially displace native low $K_m$ hexokinases from mitochondria thereby reducing the low $K_m$ hexokinase activity of said cell.

51. A method for reducing the low $K_m$ hexokinase activity of a cell, comprising contacting said cell with a composition comprising a recombinant gene that expresses a competitive inhibitor of a low $K_m$ hexokinase enzyme; wherein the inhibitor lacks low $K_m$ hexokinase activity and comprises a mitochondrial binding region from the N-terminal domain of a low $K_m$ hexokinase, said gene expression producing an amount of said inhibitor effective to substantially displace native low $K_m$ hexokinases from mitochondria thereby reducing the low $K_m$ hexokinase activity of said cell.

52. The method of claim 51, wherein said inhibitor is a truncated low $K_m$ hexokinase which is the N-terminal domain of a low $K_m$ hexokinase.

53. The method of claim 52, wherein said inhibitor is a truncated low $K_m$ hexokinase which is the amino acid sequence of SEQ ID NO:7 or the amino acid sequence from between about position 1 to about position 455 of SEQ ID NO:16.

54. The method of claim 51, wherein said inhibitor is a hexokinase-glucokinase chimera that comprises a mitochondrial binding region from the N-terminal domain of a low $K_m$ hexokinase operatively linked to at least the catalytic domain of hexokinase IV.

55. The method of claim 54, wherein said inhibitor is a hexokinase-glucokinase chimera that comprises a mitochondrial binding region from the N-terminal domain of a low $K_m$ hexokinase operatively linked to hexokinase IV.

56. The method of claim 54, wherein said inhibitor is a hexokinase-glucokinase chimera that comprises the amino acid sequence of SEQ ID NO:9 or SEQ ID NO:12.

57. The method of claim 56, wherein said recombinant gene includes the contiguous nucleic acid sequence of SEQ ID NO:8 or SEQ ID NO:11.

58. The method of claim 51, wherein said inhibitor is a low $K_m$ hexokinase enzyme that has been mutated to impair or eliminate its catalytic activity.

59. The method of claim 51, wherein, in addition to the provision of the recombinant gene that expresses said inhibitor, the low $K_m$ hexokinase activity of said cell is further reduced by the interruption of a low $K_m$ hexokinase gene.

60. The method of claim 51, wherein, in addition to the provision of the recombinant gene that expresses said inhibitor, the low $K_m$ hexokinase activity of said cell is further reduced by providing to said cell an antisense RNA molecule that is complementary to and binds to a low $K_m$ hexokinase gene or RNA transcript.

61. The method of claim 51, wherein, in addition to the provision of the recombinant gene that expresses said inhibitor, the low $K_m$ hexokinase activity of said cell is further reduced by providing to said cell a trehalose-6-phosphate synthase enzyme that stimulates the production of trehalose-6-phosphate in said cell.

62. The method of claim 51, wherein, in addition to the provision of the recombinant gene that expresses said inhibitor, the low $K_m$ hexokinase activity of said cell is further reduced by providing to said cell a ribozyme specific for an RNA transcript of a low $K_m$ hexokinase gene.

63. The method of claim 51, wherein, in addition to the recombinant gene that expresses said inhibitor, said cell further comprises a recombinant gene that expresses a selected protein.

64. The method of claim 51, wherein said cell secretes insulin in response to glucose.

65. The method of claim 64, wherein, in addition to the recombinant gene that expresses said inhibitor, said cell further comprises a recombinant hexokinase IV gene, a recombinant insulin gene or a recombinant GLUT-2 gene.

66. A method of providing glucose-responsive insulin secreting capability to a mammal, comprising administering to a mammal in need of insulin secreting capability an effective population of engineered cells that secretes insulin in response to glucose, the population comprising cells that have a reduced low $K_m$ hexokinase activity and that comprise a recombinant gene that expresses a competitive inhibitor of a low $K_m$ hexokinase enzyme, wherein the inhibitor lacks low $K_m$ hexokinase activity and comprises a mitochondrial binding region from the N-terminal domain of a low $K_m$ hexokinase, said inhibitor being present in an amount effective to substantially displace native low $K_m$ hexokinases from mitochondria thereby reducing the low $K_m$ hexokinase activity of the cells.

67. The method of claim 66, wherein said population of engineered cells comprises cells that comprise a recombinant hexokinase IV gene, a recombinant insulin gene or a recombinant GLUT-2 gene introduced into the cell by means of a recombinant vector.

68. The method of claim 67, wherein said cells comprise two recombinant genes selected from the group consisting of hexokinase IV, insulin and GLUT-2.

69. The method of claim 68, wherein said cells further comprise a recombinant hexokinase IV gene, a recombinant insulin gene and a recombinant GLUT-2 gene.

70. The method of claim 67, wherein said cells further comprise a recombinant hexokinase IV gene.

71. The method of claim 67, wherein said cells further comprise a recombinant insulin gene.

72. The method of claim 67, wherein said cells further comprise a recombinant GLUT-2 gene.

73. The method of claim 67, wherein said cells are derived from cells capable of forming secretory granules.

74. The method of claim 73, wherein said cells are derived from neuroendocrine cells.

75. The method of claim 73, wherein said cells are derived from AtT-20 cells.

76. The method of claim 73, wherein said cells are derived from pancreatic β cells.

77. The method of claim 76, wherein said cells are derived from βTC, HIT or RIN cells.

78. The method of claim 66, wherein said population of engineered cells are encapsulated in a biocompatible coating.

79. A method for producing insulin comprising the steps of:
(a) culturing an engineered cell that secretes insulin in response to glucose, the cell having a reduced low $K_m$ hexokinase activity and comprising a recombinant gene that expresses a competitive inhibitor of a low $K_m$ hexokinase enzyme, wherein the inhibitor lacks low $K_m$ hexokinase activity and comprises a mitochondrial binding region from the N-terminal domain of a low $K_m$ hexokinase, said inhibitor being present in an amount effective to substantially displace native low $K_m$ hexokinases from mitochondria thereby reducing the low $K_m$ hexokinase activity of said cell; and
(b) obtaining insulin from the cultured cell.

* * * * *

UNITED STATES PATENT AND TRADEMARK OFFICE
CERTIFICATE OF CORRECTION

| | | |
|---|---|---|
| PATENT NO. | : | 5,891,717 |
| DATED | : | April 6, 1999 |
| INVENTOR(S) | : | Christopher B. Newgard; He-Ping Han; Thomas C. Becker; John E. Wilson |

It is certified that error appears in the above-identified patent and that said Letters Patent is hereby corrected as shown below:

On the title page, item [75], line 1, delete "Newgard;" and insert therefor --Newgard, Dallas;--.

On the title page, item [75], line 2, delete "Han, both of Dallas;" and insert therefor -- Han, Arlington;"--.

In claim 46, line 1, delete "11" and insert therefor --1--.

Signed and Sealed this

Thirty-first Day of August, 1999

Attest:

Q. TODD DICKINSON

*Attesting Officer*     *Acting Commissioner of Patents and Trademarks*